(12) United States Patent
Klinman et al.

(10) Patent No.: US 9,919,058 B2
(45) Date of Patent: Mar. 20, 2018

(54) POLYKETAL PARTICLES INCLUDING A CPG OLIGODEOXYNUCLEOTIDE FOR THE TREATMENT OF LUNG CANCER

(71) Applicant: THE UNITED STATES OF AMERICA, as represented by the Secretary of Health and Human Services, Washington, DC (US)

(72) Inventors: Dennis M. Klinman, Potomac, MD (US); Takashi Sato, Yokohama (JP)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/326,387

(22) PCT Filed: Jul. 8, 2015

(86) PCT No.: PCT/US2015/039574
§ 371 (c)(1),
(2) Date: Jan. 13, 2017

(87) PCT Pub. No.: WO2016/010788
PCT Pub. Date: Jan. 21, 2016

(65) Prior Publication Data
US 2017/0202977 A1 Jul. 20, 2017

Related U.S. Application Data

(60) Provisional application No. 62/024,657, filed on Jul. 15, 2014.

(51) Int. Cl.
*C12N 15/117* (2010.01)
*A61K 47/48* (2006.01)
*A61K 31/7088* (2006.01)
*A61K 31/475* (2006.01)

(52) U.S. Cl.
CPC ...... *A61K 47/48907* (2013.01); *A61K 31/475* (2013.01); *A61K 31/7088* (2013.01)

(58) Field of Classification Search
CPC ................ C12N 15/111; C12N 15/117; A61K 2039/55561
See application file for complete search history.

(56) References Cited

U.S. PATENT DOCUMENTS

| | | |
|---|---|---|
| 7,951,898 B2 | 5/2011 | Ppisov |
| 8,629,151 B2 | 1/2014 | Zepp et al. |
| 8,685,416 B2 | 4/2014 | Klinman et al. |
| 2004/0265351 A1 | 12/2004 | Miller et al. |
| 2005/0214355 A1 | 9/2005 | Klinman et al. |
| 2009/0011993 A1 | 1/2009 | Murthy et al. |
| 2013/0028941 A1 | 1/2013 | Altreuter et al. |
| 2014/0030344 A1 | 1/2014 | Zepp et al. |

FOREIGN PATENT DOCUMENTS

| | | |
|---|---|---|
| CA | 2 608 086 | 11/2006 |
| WO | WO 2006/052900 A2 | 5/2006 |
| WO | WO 2006/122223 A2 | 11/2006 |
| WO | WO 2010/138193 A2 | 12/2010 |
| WO | WO 2011/109422 A1 | 9/2011 |
| WO | WO 2011/140644 A1 | 11/2011 |

OTHER PUBLICATIONS

"Adjuvant/deliver systems for subunit vaccines," https://www.bcm.edu/departments/molecular-virology-and-microbiology/?pmid=25141 (printed from the internet on May 13, 2014).
Fiore et al., "Polyketal microparticles for therapeutic delivery to the lung," *Biomaterials* 31(5): 810-817 (Feb. 2010).
Heffernan and Murthy, "Polyketal nanoparticles: A new pH-sensitive biodegradable drug delivery vehicle," *Bioconjugate Chem.* 16: 1340-1342 (2005).
Heffernan et al., "The stimulation of CD8+ T cells by dendritic cells pulsed with polyketal microparticles containing ion-paired protein antigen and poly(inosinic acid)—poly(cytidylic acid)," *Biomaterials* 30(5): 910-918 (Feb. 2009).
Heffernan, "Biodegradable polymeric deliver systems for protein subunit vaccines," *Dissertation, University of Georgia* (2008).
Hubbell et al., "Materials engineering for immunomodulation," *Nature* 462: 449-460 (Nov. 26, 2009).
International Search Report from parent PCT Application No. PCT/US2015/039574, 5 pages (dated Oct. 14, 2015).
Wang et al., "Antigen-specific immune response of microparticle vaccine containing CpG-ODN and protein," *Society for Biomaterials* (2013)(Abstract 236).
Written Opinion from parent PCT Application No. PCT/US2015/039574, 6 pages dated Oct. 14, 2015).
Yang et al., "Polyketal Copolymers: A new acid-sensitive delivery vehicle for treating acute inflammatory diseases," *Bioconjugate Chem.* 19(6): 1164-1169 (Jun. 1, 2008).
Zhao et al.., "Combination therapy targeting toll like receptors," *Journal for Immuno-Therapy of Cancer* 2014, 2(12) 10 pages (May 13, 2014).
Belani et al., "Phase 2 trial of erlotinib with or without PF-3512676 (CPG 7909, a Toll-like receptor 9 agonist) in patients with advanced recurrent EGFR-positive non-small cell lung cancer," *Cancer Biology & Therapy* 14(7): 557-563 (Jul. 2013).

(Continued)

Primary Examiner — Jon E Angell
(74) Attorney, Agent, or Firm — Klarquist Sparkman, LLP

(57) ABSTRACT

Methods are disclosed herein for treating a subject with a lung cancer. The lung cancer can be small cell carcinoma of the lung or non-small cell carcinoma of the lung.

The methods include locally administering to the subject a therapeutically effective amount of the polyketal particle comprising a CpG oligodexoynucleotide. Optionally, the polyketal particle can include an imidazoquinoline compound.

23 Claims, 20 Drawing Sheets

(56) References Cited

OTHER PUBLICATIONS

Readett et al., "PF-3512676 (CPG 7909), a toll-like receptor 9 agonist-status of development for non-small cell lung cancer (NSCLC)," *Journal of Thoracic Oncology* 2(8, Supplement 4): S461 (Aug. 2007).

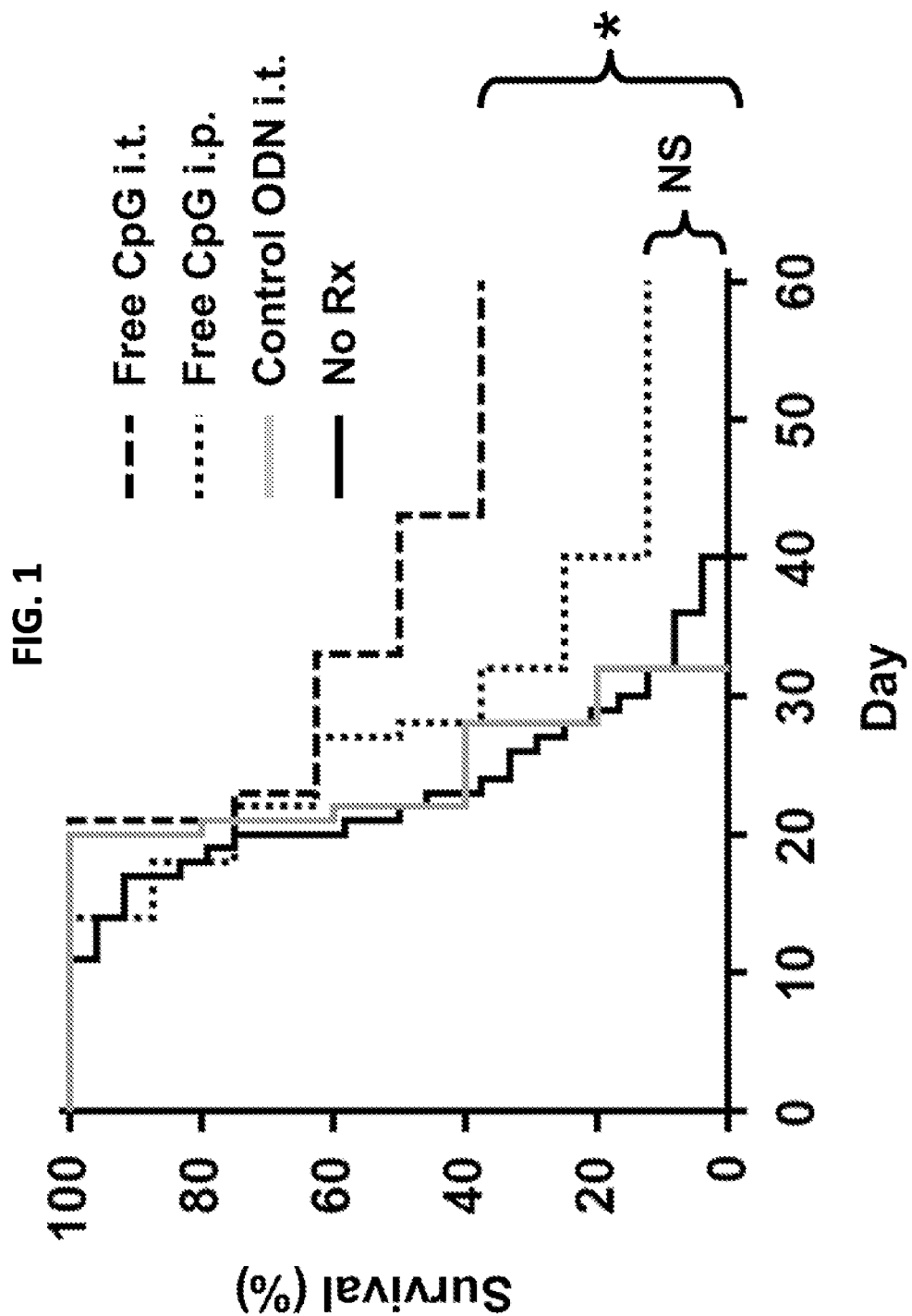

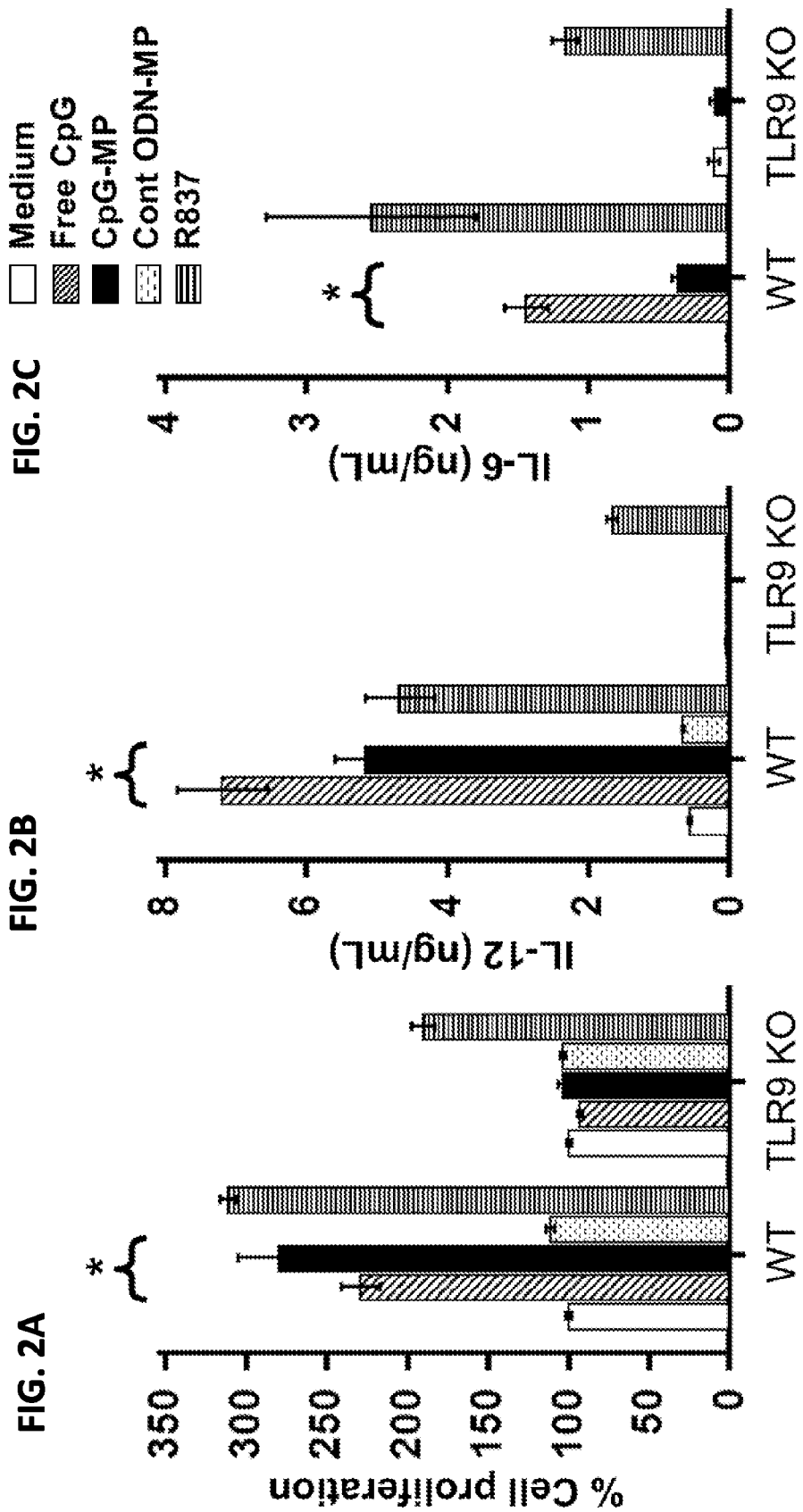

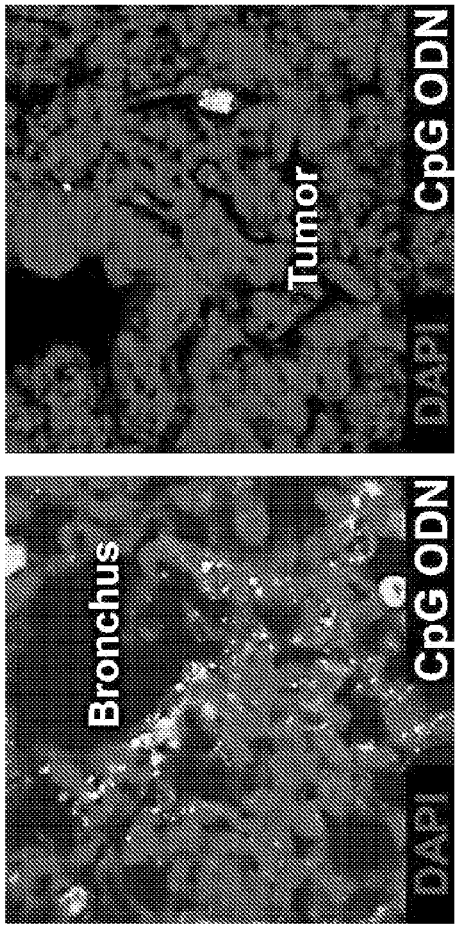
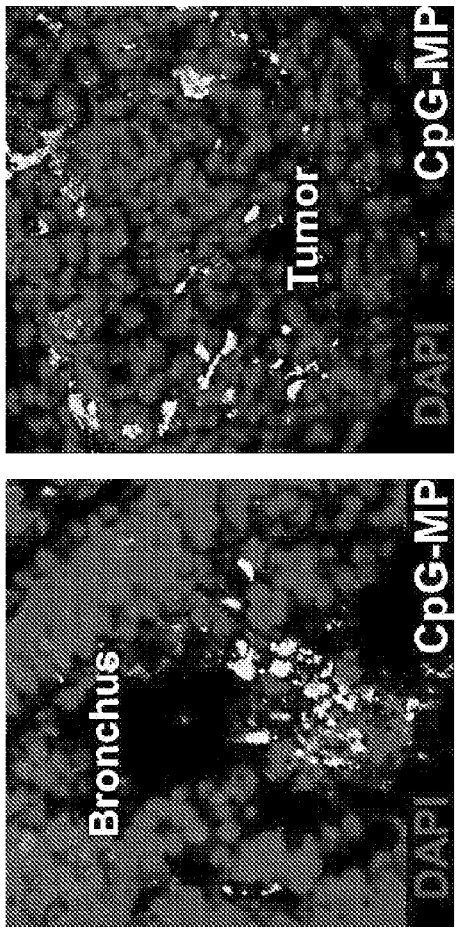
FIG. 3E 48 hr
FIG. 3F
FIG. 3B 48 hr
FIG. 3D
FIG. 3A 6 hr
FIG. 3C

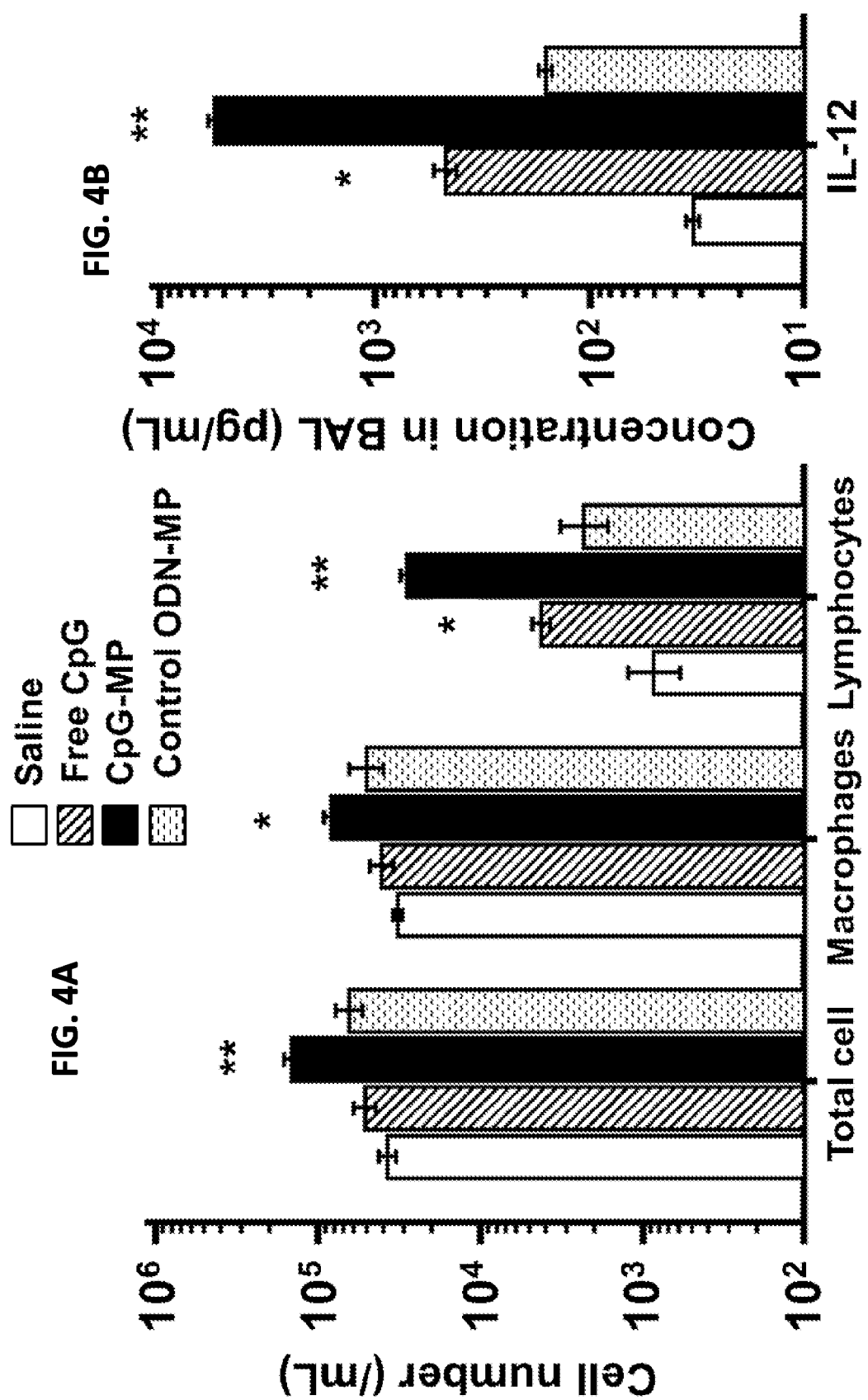

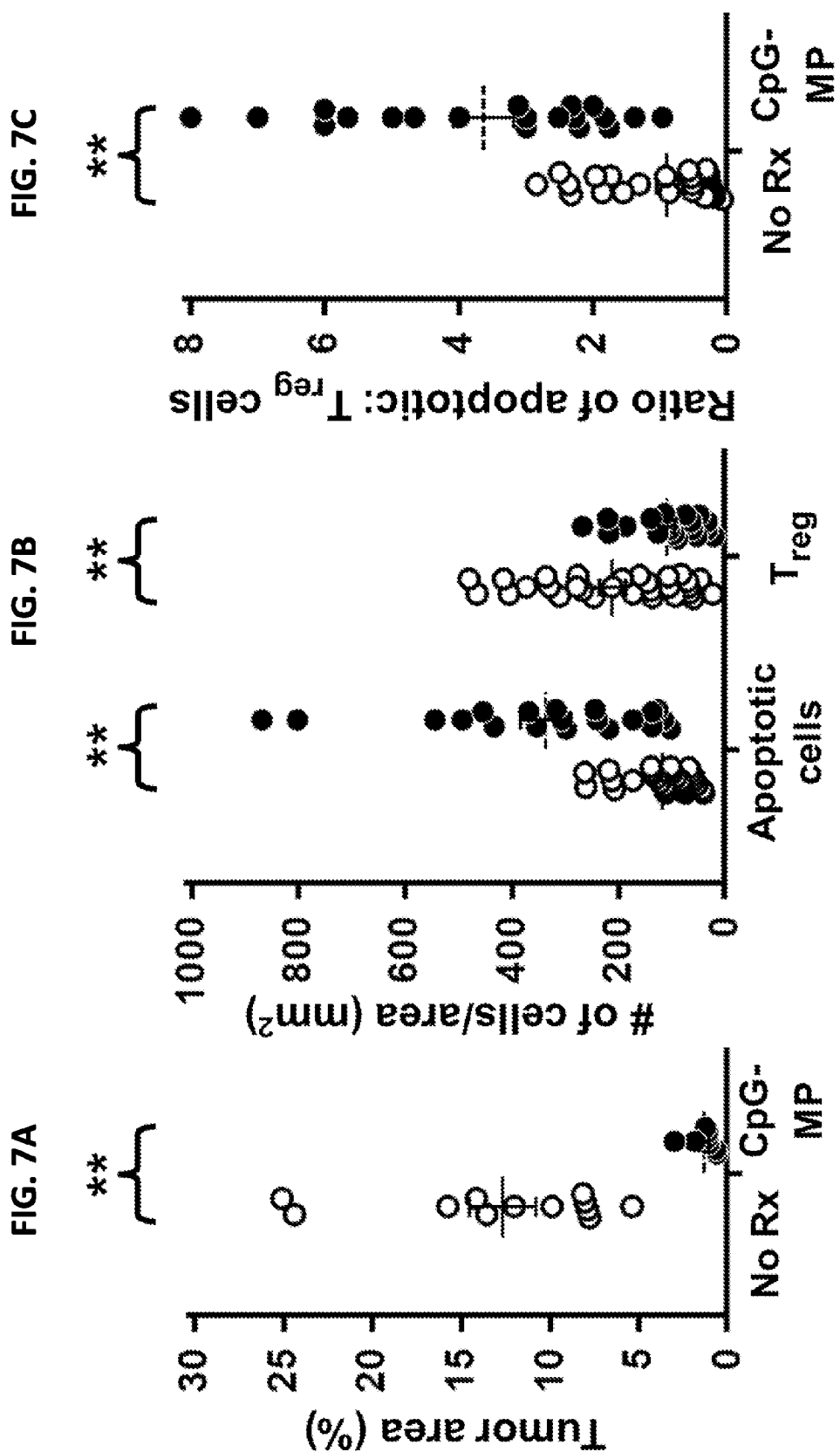

FIG. 10A
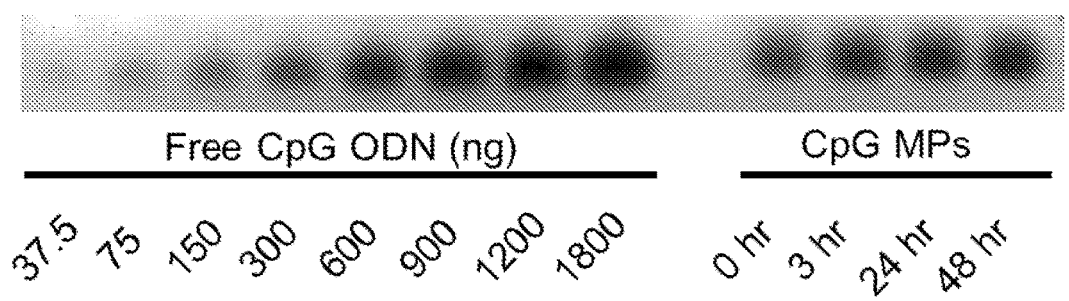
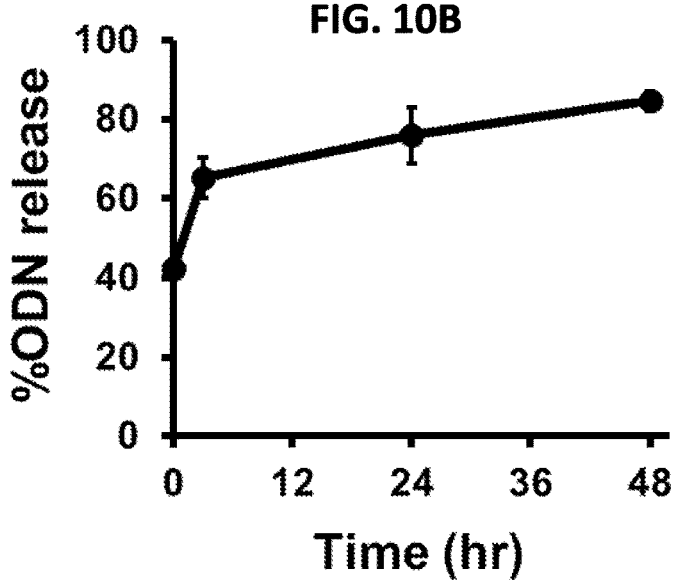
FIG. 10B

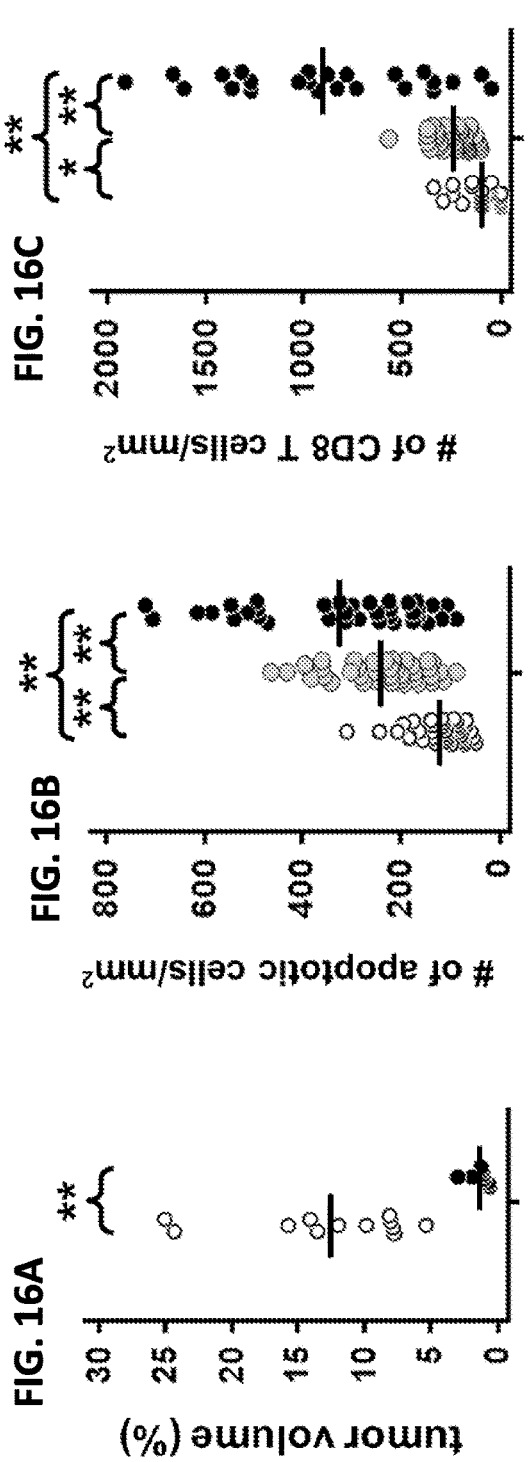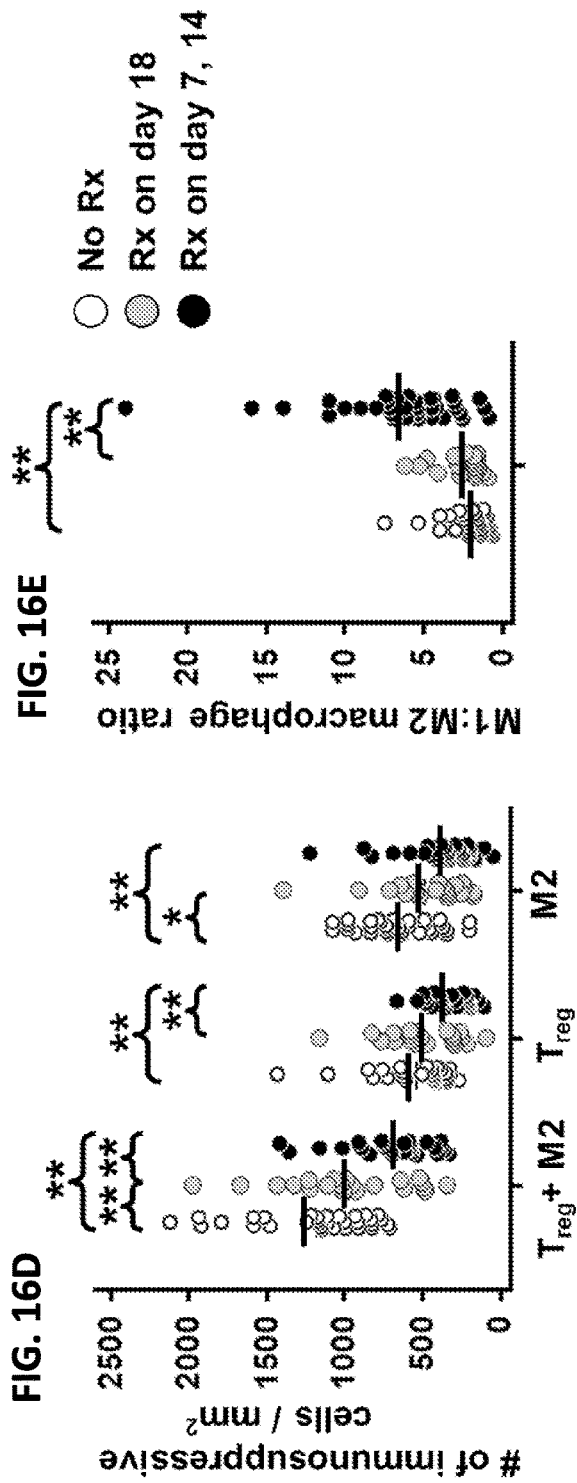

POLYKETAL PARTICLES INCLUDING A CPG OLIGODEOXYNUCLEOTIDE FOR THE TREATMENT OF LUNG CANCER

CROSS REFERENCE TO RELATED APPLICATION

This is a § 371 U.S. national stage of International Application No. PCT/US2015/039574, filed Jul. 8, 2015, which was published in English under PCT Article 21(2), which claims the benefit of U.S. Provisional Application No. 62/024,657, filed Jul. 15, 2014, which is incorporated by reference herein.

FIELD OF THE DISCLOSURE

This relates to the field of cancer, specifically to polyketal particles, such as nanoparticles, that include a CpG oligodeoxynucleotide and their use to treat lung cancer.

BACKGROUND

Lung cancer is the leading cause of cancer-related death in the United States with non-small cell lung cancer (NSCLC) accounting for 85% of these tumors (Siegel et al., *CA Cancer J Clin* 2013; 63:11-30). Despite recent advances in multimodal therapies including targeted and tailored therapies, the 5-year survival rate for NSCLC remains low at about 15%. Accumulating evidence suggests that controlling the primary tumor can enhance survival even in patients with advanced/metastatic disease (Verhoef et al., *Eur J Cancer* 2011; 47 Suppl 3:S61-6, Chang G J., *J Clin Oncol* 2012; 30:3165-3166). Lung tumors tend to be poorly immunogenic and resistant to immune surveillance. Thus, a need remains for compositions that can be used to activate the pulmonary immune system and promote tumor regression (Bradbury et al., *J Thorac Oncol* 2008; 3:164-170, Rakoff-Nahoum et al., *Nat Rev Cancer* 2009; 9:57-63).

SUMMARY OF THE DISCLOSURE

Methods are disclosed herein for treating a subject with a lung cancer. The lung cancer can be small cell carcinoma of the lung or non-small cell carcinoma of the lung. The methods include locally administering to the subject a therapeutically effective amount of the polyketal particle, such as a microparticle or nanoparticle, comprising a CpG oligodexoynucleotide. In some embodiments, the CpG oligodeoxynucleotide is a K-type CpG oligodeoxynucleotide, wherein the K-type CpG oligodeoxynucleotide has a nucleic acid sequence set forth as:

(SEQ ID NO: 2)
5' $N_1N_2N_3D$-CpG-$WN_4N_5N_6$ 3' wherein the central CpG motif is unmethylated, D is T, G or A, W is A or T, and $N_1$, $N_2$, $N_3$, $N_4$, $N_5$, and $N_6$ are any nucleotide, wherein the CpG oligodeoxynucleotide is 10 to 30 nucleotides in length.

In other embodiments the CpG oligodeoxynuclotide is a D-type CpG oligodeoxynucleotide, wherein the D-type CpG oligodeoxynucleotide has a sequence (SEQ ID NO: 1)
5' $X_1X_2X_3$ $Pu_1$ $Py_2$ CpG $Pu_3$ $Py_4$ $X_4X_5X_6(W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10, and wherein the CpG oligodeoxynucleotide is 18 to 50 nucleotides in length.

In some embodiments, the polyketal nanoparticle is about 150-500 nm in diameter, for example 200-400 nm, such as 200-325 nm. In other embodiments, the polyketal nanoparticle also includes an imidazoquinoline compound. In additional embodiments, the nanoparticles are assembled into a microparticle. In some examples, such as formulations for endotracheal administration, self-assembled, freeze dried microparticles having a diameter of 1-5 micrometers are used to enhance efficient delivery to the lungs by inhalation, particularly for reaching the distal alveoli of the lung.

In some embodiments, the particle is a polyketal particle, for example a nanoparticle that degrades by acid catalyzed hydrolysis into substantially non-inflammatory low molecular weight compounds that are subsequently excreted. In some embodiments, the polyketal particle degrades into a dimethoxypropane and either a benzene dimethanol or a cyclohexane dimethanol. In more particular embodiments, the polyketal particle degrades into 2,2-dimethoxypropane and either a 1,4-benzene dimethanol or a 1,4-cyclohexane dimethanol. In other embodiments, the polyketal particle is either PPADK, PCADK, or a PK1, 2, 3, 4, 5 or 6.

The foregoing and other features and advantages of the invention will become more apparent from the following detailed description of several embodiments which proceeds with reference to the accompanying figures.

BRIEF DESCRIPTION OF THE FIGURES

FIG. 1. Effect of CpG ODN on survival. $10^6$ LLC were implanted intra-tracheally into the lungs of syngeneic C57BL/6 mice. Mice were treated with 50 μg of CpG or control ODN locally (i.t.) or systemically (i.p.) weekly for one month, starting on day 7. Survival was analyzed by Kaplan-Meier statistics using the log-rank test. Data from 2-3 independent experiments involving 5-24 mice/group were combined to generate the survival curves. NS; not significant, *, p<0.05 vs No Rx.

FIGS. 2A-2C. In vitro activity of CpG-NP (aggregates provided microprticles "MP'). Spleen cells from WT or TLR9 KO mice were cultured with 1 μM of free or NP adsorbed CpG ODN or 1 μg/mL of R837 (TLR7 ligand). 2A) Cell proliferation after 72 hr. 2B, 2C) IL-12 and IL-6 production after 24 hr. Results show the mean±SE from 2 independent experiments performed in triplicate. *, p<0.05.

FIGS. 3A-3F. Biodistribution of CpG ODN. LLC were implanted as described in FIG. 1. Fluorescein-labeled CpG-NP or free CpG ODN were delivered i.t. 6 or 48 hr before sacrifice on day 20. Tissue samples were stained to identify macrophages (red F4/80+), DC (red CD205+) or CpG (green) and analyzed by confocal microscopy. Note that CpG-NP initially localized to the bronchial mucosa and subsequently accumulated in tumor nests.

FIGS. 4A-4B. Activity of CpG-NP (aggregates provided microprticles "MP') in vivo. 50 μg of CpG ODN (free or adsorbed onto NP) was administered i.t. to normal mice. BAL was collected and analyzed for (4A) cellularity and (4B) IL-12 levels 2 days later. Results show the mean±SE (N=3-4/group). *, p<0.05, **, p<0.01 vs saline control.

FIGS. 7A-7C. Effect of CpG-NP (aggregates provided microprticles "MP") on the tumor microenvironment. LLC were implanted and mice treated with CpG-NP as described in FIG. 1. Lungs were collected on day 20. 7A) Total tumor area as determined by measuring mid-lung sections. 7B) Number of apoptotic (TUNEL$^+$) and 7C) $T_{reg}$ (Foxp3$^+$) cells per $mm^2$ of tumor as determined in serial sections of 30 tumor nodules from 6 untreated mice (○) and 20 nodules from 6 CpG-NP treated mice (●).**, p<0.01 vs tumors in untreated mice.

FIGS. 10A-10B. Release of CpG ODN from CpG-NP. 10A) Desorption of CpG ODN from CpG-NP was monitored by suspending particles in physiological saline (pH 7.4, 37° C.). Supernatants were collected over time, loaded onto a 3% agarose gel, electrophoresed and visualized by staining with SYBR Gold. 10B) The percent of ODN released was calculated by the formula: (measured ODN)/(total ODN used to formulate the CpG-NP)×100%. Results are representative of 3 independent experiments.

FIGS. 16A-16E. Effect of CpG-MP (CpG-NP (nanoparticles) were freeze-dried and formed micropartcles (MP)) on tumor infiltrating immune cells. LLC were implanted as described in FIG. 1 and mice were treated with CpG-NP once on day 18 (gray circles) or twice on days 7 and 14 (black circles). Lungs were collected on day 20. FIG. 16A shows the total tumor volume as determined by measuring mid-lung sections from 8-12 mice per group. FIG. 16B shows the total number of apoptotic (TUNEL$^+$) cells. FIG. 16C shows CD8$^+$ T cells (CD3$^+$, CD8$^+$), and FIG. 16D shows immunosuppressive $T_{reg}$ (Foxp3$^+$) plus M2 macrophages (F4/80$^+$, CD206$^+$). In FIG. 16E, the ratio of M1 (F4/80$^+$ CD206$^-$): M2 macrophages per $mm^2$ of tumor was quantified in 15-39 tumors from three mice per group. *, p<0.05, **, p<0.01 (One way Anova).

SEQUENCE LISTING

Figure 5:
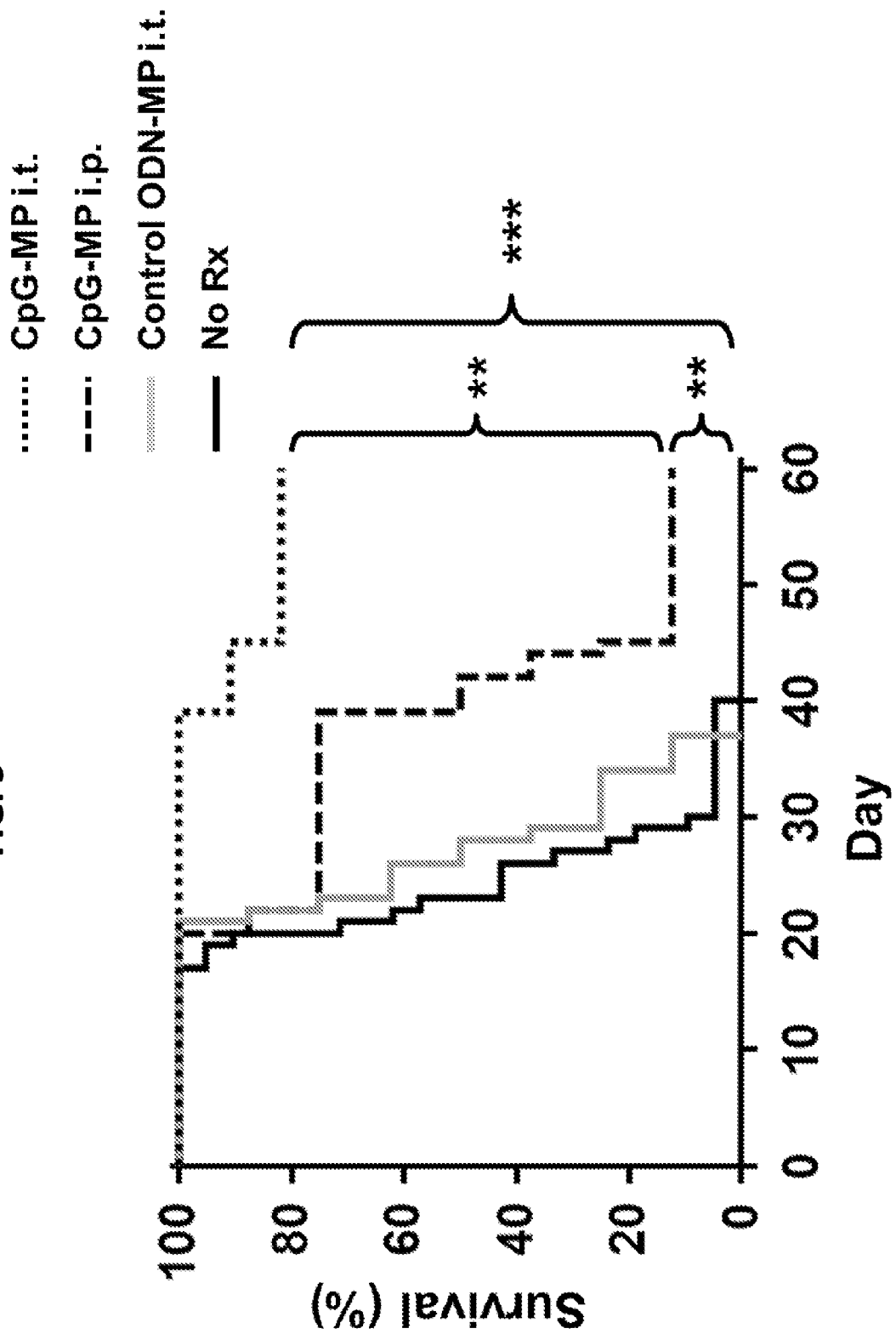
FIG. 5. Effect of CpG-NP (aggregates provided microprticles "MP') on survival in LLC challenged mice. LLC were implanted and mice treated with CpG-NP as described in FIG. 1. Survival curves were generated and analyzed by Kaplan-Meier statistics using the log-rank test. Data from 2-3 independent experiments involving 8-21 mice/group were combined to generate each survival curve. , p<0.01, *, p<0.001 vs No Rx (WT).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-93018-03_Sequence-_Listing.txt, Jan. 11, 2017, 15.8 KB], which is incorporated by reference herein.

In the accompanying sequence listing:
SEQ ID NO: 1 is a D-type CpG oligodeoxynucleotide (ODN).
SEQ ID NOs: 2-34 are K-type CpG ODNs.
SEQ ID NOs: 35-36 are control ODNs.
SEQ ID NOs: 37-63 are D-type CpG ODN.

DETAILED DESCRIPTION OF SEVERAL EMBODIMENTS

Synthetic oligonucleotides (ODN) including CpG motifs (CpG ODN) elicit strong anti-tumor responses by triggering immune cells via Toll-like receptor 9. Optimal anti-tumor activity requires that the CpG ODN reach the tumor site. It is disclosed herein that polyketal particles including a CpG ODN can be delivered locally to treat lung cancer. These particles optionally can include an imidazoquinoline compound.

It is disclosed herein that, in an animal model of lung cancer, polyketal delivery particles including a CpG ODN accumulated and persisted in pulmonary tumor nodules, eliciting a robust Th1 response. This was accompanied by a significant reduction in the frequency of immunosuppressive $T_{reg}$ and M2 macrophages in the tumor microenvironment. Without being bound by theory, the combination of improved anti-tumor immunity and decreased immune suppression can be used to significantly increase apoptotic death of lung cancer cells. Efficacy was documented in models of primary lung cancer and metastatic lung cancer.

Thus, the methods disclosed herein can be used to increase survival of subjects with lung cancer, such as, but not limited to, non-small cell carcinoma of the lung.

Terms

Alkyl: A saturated or unsaturated monovalent hydrocarbon radical having a number of carbon atoms ranging from one to 30 (e.g., $C_{1-30}$ alkyl), which is derived from removing one hydrogen atom from one carbon atom of a parent compound (e.g., alkane, alkene, alkyne). An alkyl group may be branched, straight-chain, or cyclic.

Alkenyl: An unsaturated monovalent hydrocarbon radical having a number of carbon atoms ranging from two to 30 (e.g., $C_{2-30}$ alkenyl), which has at least one carbon-carbon double bond and is derived from removing one hydrogen atom from one carbon atom of a parent alkene. An alkenyl group may be branched, straight-chain, cyclic, cis, or trans.

Alkynyl: A unsaturated monovalent hydrocarbon radical having a number of carbon atoms ranging from two to 30 (e.g., $C_{2-30}$ alkynyl), which has at least one carbon-carbon triple bond and is derived from removing one hydrogen atom from one carbon atom of a parent alkyne. An alkynyl group may be branched, straight-chain, or cyclic.

Animal: Living multi-cellular vertebrate organisms, a category that includes, for example, mammals and birds. The term mammal includes both human and non-human mammals. Similarly, the term "subject" includes both human and veterinary subjects.

Biocompatible: Exerting minimal destructive or host response effects while in contact with body fluids or living cells or tissues. Thus a biocompatible group may contain an aliphatic, alicyclic, heteroaliphatic, heteroalicyclic, aryl or heteroaryl moiety, which falls within the definition of the term biocompatible. The term "biocompatibility" is alternatively taken to mean minimal interactions with recognition proteins, e.g., naturally occurring antibodies, cell proteins, cells and other components of biological systems. However, substances and functional groups specifically intended to cause the above effects, e.g., drugs and prodrugs, are considered to be biocompatible.

"C" class oligodeoxynucleotides (ODNs): ODNs that resemble K ODNs and are composed of only phosphorothioate nucleotides. Typically, C class ODNs have a TCGTCG motif at the 5' end and have a CpG motif imbedded in a palindromic sequence. Backbone modifications like 2'-O-methyl modifications especially in the 5' part of the ODN influence IFN-alpha-producing capacity of these ODN. C class ODNs have combined properties of D- and K-type CpG ODNs. This class of ODNs stimulates B cells to secrete IL-6 and stimulates plasmacytoid dendritic cells to produce interferon-α. C class ODNs also induce IP-10 production and strong NK activation.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer a significant part of the activity to the CpG oligodeoxynucleotide. A CpG oligodeoxynucleotide is an oligodeoxynucleotide that is at least about ten nucleotides in length and includes an unmethylated CpG. CpG oligodeoxynucleotides include both D and K-type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer: A malignant tumor that has undergone characteristic anaplasia with loss of differentiation, increase rate of growth, invasion of surrounding tissue, and is capable of metastasis. For example, thyroid cancer is a malignant tumor that arises in or from thyroid tissue, and breast cancer is a malignant tumor that arises in or from breast tissue (such as a ductal carcinoma). Residual cancer is cancer that remains in a subject after any form of treatment given to the subject to reduce or eradicate the cancer. Metastatic cancer is a tumor at one or more sites in the body other than the site of origin of the original (primary) cancer from which the metastatic cancer is derived. Cancer includes, but is not limited to, solid tumors.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

Cytokine: Proteins made by cells that affect the behavior of other cells, such as lymphocytes. In one embodiment, a cytokine is a chemokine, a molecule that affects cellular trafficking. Specific non-limiting examples of cytokines are interferon (IFN)γ, IL-6, and IL-10.

D-type Oligodeoxynucleotide (D ODN): An oligodeoxynucleotide including an unmethylated CpG motif that has a sequence represented by the formula:

$$5'\ RY\text{-}CpG\text{-}RY\ 3'$$

wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D-type CpG ODN is at least about 16 nucleotides in length and includes a sequence represented by Formula III:

$$5'\text{-}X_1X_2X_3\ Pu_1\ Py_2\ CpG\ Pu_3\ Py_4\ X_4X_5X_6(W)_M\ (G)_N\text{-}3'\quad(\text{SEQ ID NO: 1})$$

wherein the central CpG motif is unmethylated, Pu is a purine nucleotide, Py is a pyrimidine nucleotide, X and W are any nucleotide, M is any integer from 0 to 10, and N is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular response. In some examples D ODNs can be up to 30, 35, 40, 45 or 50 nucleotides in length. For example, D ODNs stimulate natural killer cells and the maturation of dendritic cells.

Heteroalkyl/Heteroalkenyl/Heteroalkynyl: An alkyl, alkenyl, or alkynyl group, respectively, wherein one or more of the carbon atoms are each independently replaced with the one or more heteroatoms selected from oxygen, sulfur, and nitrogen.

Hydrophilic: The term "hydrophilic" as it relates to substituents on the polymer monomeric units denotes organic moieties which contain ionizable, polar, or polarizable atoms, or which otherwise may be solvated by water molecules. Thus a hydrophilic group, as used herein, refers to an aliphatic, alicyclic, heteroaliphatic, heteroalicyclic, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol (CH$_2$OH) or a glycol (for example, CHOH—CH$_2$OH or CH—(CH$_2$OH)$_2$).

As it relates to the polyketal polymers of the nanoparticles, "hydrophilic" denotes polymers comprising hydrophilic functional groups as defined above. In a particular embodiment, a hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

Immune response: A response of a cell of the immune system, such as a B cell or T cell to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFNγ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One, specific, non-limiting example of a statistical test used to assess a substantial increase is the use of a Z test to compare the percent of samples that respond to an imidazoquinoline compound and a K-type CpG ODN as compared to the percent of samples that respond using the another type of ODN, such as a D-type CpG ODN, or as compared to the K-type CpG ODN alone (without the imidazoquinoline compound). A non-parametric ANOVA can be used to compare differences in the magnitude of the response induced by a imidazoquinoline compound a K-type CpG ODN as compared to the percent of samples that respond using the K-type CpG ODN alone or the imidazoquinoline compound alone. In this example, p≤0.05 is significant, and indicates a substantial increase in the parameter. One of skill in the art can readily identify other statistical assays of use.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Ketal: A type of acetal compound that has the following general structural formula:

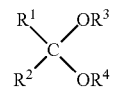

In some examples neither R1 or R2 are hydrogen; for example R1=alkyl or aryl, and R2=alkyl or aryl. A polyketal contains repeating monomers of a ketal; the polyketals degrade into neutral compounds, for example a dimethoxypropane and a diol, or acetone and an alcohol such as a diol.

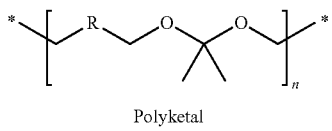

Polyketal

An example of a polyketal is poly (1,4-phenylacetone dimethylene ketal) (PPADK), which forms a microparticle that degrades into its component 2,2-dimethoxypropane and 1,4-benzene dimethanol. Another example of a polyketal is poly (cyclohexane-1,4-diryl acetone dimethylene ketal) (PCADK), an aliphatic polyketal that degrades into 2,2-dimethoxypropane and 1,4-cyclohexanedimethanol. In the PPADK and PCADK embodiments of the polyketal, R in the polyketal structure above is either a cyclohexyl or phenyl.

K-Type Oligodeoxynucleotide (K ODN): An oligodeoxynucleotide including an unmethylated CpG motif that has a sequence represented by the formula:

(SEQ ID NO: 2)
5' $N_1N_2N_3$D-CpG-W$N_4N_5N_6$-3' wherein the central CpG motif is unmethylated, D is T, G or A, W is A or T, and $N_1$, $N_2$, $N_3$, $N_4$, $N_5$, and $N_6$ are any nucleotides. In one embodiment, D is a T. Additional description of K-type CpG ODN sequences and their activities can be found in the description below. Generally K-type CpG ODNs can stimulate a humoral response. For example, K-type CpG ODNs stimulate the production of immunoglobulins, such as IgM and IgG. K-type CpG ODNs can also stimulate proliferation of peripheral blood mononuclear cells and increase expression of IL-6 and/or IL-12, amongst other activities. In some embodiments, a K-type CpG ODN is up to 30, 35, 40, 45, or 50 nucleotides in length.

Lung cancer: The main type of lung cancer is carcinoma of the lung, which includes small cell lung carcinoma and non-small cell lung carcinoma. Non-small cell lung carcinoma (NSCLC) is sometimes treated with surgery, while small cell lung carcinoma (SCLC) usually responds to chemotherapy and radiation. The most common cause of lung cancer is long-term exposure to tobacco smoke.

NSCLC is any type of lung cancer other than SCLC. The NSCLCs are grouped together because their prognosis and management are similar. There are three main sub-types: squamous cell lung carcinoma (SQCC), adenocarcinoma (ADC), and large cell lung carcinoma. Both ADC and large cell carcinoma are classified as non-squamous cell type carcinoma. ADC can be grouped into subclasses, including acinar carcinoma, papillary carcinoma, bronchoalveolar carcinoma (BAC), solid tumor, and mixed subtypes (2004 World Health Organization classification of lung tumors, Beasley et al., Semin. Roentgenol. 40:90-97, 2004). Large cell carcinoma includes the subclasses giant cell tumors, clear cell carcinoma, adenosquamous carcinoma, and undifferentiated carcinoma.

Squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 40% of lung cancers. It usually originates in peripheral lung tissue. Most cases of adenocarcinoma are associated with smoking; however, among people who have never smoked, adenocarcinoma is the most common form of lung cancer.

Small cell lung cancers (SCLC, also called "oat cell carcinoma") are less common. SCLC tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Mammal: This term includes both human and non-human mammals. Similarly, the term "subject" includes both human and veterinary subjects.

Normal cells or tissue: Non-tumor, non-malignant cells and tissue, such as lung tissue.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxynucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: non-ionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligodeoxynucleotide," "immunostimulatory CpG containing oligodeoxynucleotide," "CpG ODN," refers to an oligodeoxynucleotide, which contains a cytosine, guanine dinucleotide sequence and (e.g. has a mitogenic effect or induces cytokine production) vertebrate immune cells. In one embodiment, an immunostimulatory CpG ODN stimulates a parameter of an immune response in a subject. The cytosine, guanine is unmethylated.

An "oligonucleotide delivery complex" is an oligonucleotide associated with (e.g. ionically or covalently bound to or encapsulated within) a targeting agent (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167:3324, 2001).

Particle: A small object that behaves as a whole unit with respect to its transport and properties. A "nanoparticle" has a diameter of 1 nm to 1,000 nm, and in some examples is 1-100 nm. A microparticle has a diameter of over 1 μm, for example 1-100 μm. A microparticle may contain multiple nanoparticle subunits, for example nanoparticles that assemble or associate into microparticles. Hence the term "microparticle" includes embodiments in which the microparticle is made up of component nanoparticles. In such embodiments, a microparticle is comprised of nanoparticles. A particle comprising nanoparticles may be a microparticle. A particle consisting of nanoparticles would exclude particles having a diameter over 1 μm. In some specific examples, a nanoparticle has a diameter of about 100 to about 500 nm, 150 nm to 500 nm, or 200 nm to 400 nm. In this context, "about" indicates within 10 nm of the specified size. A "microparticle" has a diameter of about 1 to about 100 μm. In some embodiments, the microparticle has a diameter of about 1 to about 10 μm. In other examples, a microparticle has a diameter of about 1 to about 3 μm in size. In this context, "about" is within 0.05 μm.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in the methods and compositions disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor.

Purified: The term purified does not require absolute purity; rather, it is intended as a relative term. Thus, for example, a purified peptide preparation is one in which the peptide or protein is more enriched than the peptide or protein is in its natural environment within a cell. Preferably, in a purified preparation, the protein or peptide represents at least 50% of the total peptide or protein content of the preparation. Similarly, in a purified preparation of oligodeoxynucleotides, the oligodeoxynucleotide represents at least 50% of the total nucleic acid content of the preparation.

Self-complementary nucleic acid sequence: A nucleic acid sequence that can form Watson-Crick base pairs. The four bases characteristic of deoxyribonucleic acid unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Smoker: The U.S. National Health Interview Survey (NHIS) current smoking definition is based on two questions with the present wording in use since 1992 (Centers for Disease Control and Prevention, Morbidity and Mortality Weekly Report 43: 342-346, 1994). The first question, asked of all respondents, is "have you smoked at least 100 cigarettes in your entire life?" Respondents who answer "yes" are classified as ever smokers, and those who answer "no" are classified as never smokers ("non-smokers") and excluded from subsequent cigarette use questions. Ever smokers are then asked a second question: "do you now smoke cigarettes every day, some days or not at all?" Respondents who answer "every day" or "some days" are classified as "current smokers." Respondents who answer "not at all" are classified as "ex-smokers."

Specific binding: Binding which occurs between such paired species as enzyme/substrate, receptor/agonist, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two that produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. A TLR-9 agonist binds to TLR-9 and not to other TLRs, such as TLR-7 or TLR-8. Similarly, a TLR-7 agonist binds to TLR-7 and not to other TLRs, such as TLR-9.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as an aryl group, a cyclic group, a heteroaryl group or a heterocyclic group.

Therapeutically effective dose: A dose sufficient to prevent advancement, or to cause regression of a disease, or which is capable of relieving symptoms caused by a disease, such as pain.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A tumor may be hematologic (such as chronic or acute leukemia) or solid (such as melanoma, lung cancer, lymphoma breast cancer or colon cancer).

An "established" or "existing" tumor is an existing tumor that can be discerned by diagnostic tests. In some embodiments, and established tumor can be palpated or visualized. In some embodiments, an "established tumor" is at least 500 mm³, such as at least 600 mm³, at least 700 mm³, or at least 800 mm³ in size. In other embodiments, the tumor is at least 1 cm long. With regard to a solid tumor, an established tumor generally has a robust blood supply, and has induced Tregs and myeloid derviced suppressor cells (MDSC).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. The term "comprises" means "includes." Therefore, comprising "A" or "B" refers to including A, including B, or including both A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

CpG Oligodeoxynucleotides (ODNs)

Several types of CpG ODN are known in the art and can be used in the methods disclosed herein. These include K-type CpG ODN, D-type CpG ODN, and C ODN. In some embodiments, the ODN is at most 50, at most 45, at most 40, at most 35, at most 30, at most 25 or at most 20 nucleotides in length.

Combinations of ODNs can also be used, including multiple K-type CpG ODN, multiple D-type CpG ODN, and multiple C-type ODN. In some examples, more than one K-type CpG ODN are administered to the subject. In other examples, more than one D-type CpG ODN are administered to the subject. In yet other examples, more than one C-type ODN are administered to the subject. In further examples, at least one K-type CpG ODN and at least one C-type ODNs are administered to the subject. In some embodiments, a K-type CpG ODN is not administered in combination with a D-type CpG ODN.

A. K-Type CpG ODN

In several embodiments, a K-type CpG ODN or a mixture of K-type CpG ODNs is utilized in the methods disclosed herein. Briefly, the K-type CpG ODN nucleic acid sequences useful in the methods disclosed herein are represented by the formula:

wherein at least one nucleotide separates consecutive CpGs; D is adenine, guanine, or thymidine; Y is cytosine or thymine, N is any nucleotide and $N_1+N_2$ is from about 0-26 bases. In one embodiment, $N_1$ and $N_2$ do not contain a CCGG quadmer or more than one CGG trimer; and the nucleic acid sequence is from about 8-30 bases in length, such as about 10 to 30 nucleotides in length. However, nucleic acids of any size (even many kb long) can be used in the methods disclosed herein if CpGs are present. In one embodiment, synthetic oligonucleotides of use do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs).

In another embodiment, the methods include the use of an ODN which contains a CpG motif represented by the formula:

wherein at least one nucleotide separates consecutive CpGs; RD is selected from the group consisting of GpT, GpG, GpA, ApT and ApA; YT is selected from the group consisting of TpT or CpT; N is any nucleotide and $N_1+N_2$ is from about 0-26 bases, such that the ODN is about 8 to 30 nucleotides in length.

In several embodiments, the methods disclosed herein include the use of an effective amount of at least one K-type CpG ODN, wherein the K-type CpG ODNs include an unmethylated CpG motif that has a sequence represented by the formula:

(SEQ ID NO: 2)
5' N₁N₂N₃D-CpG-WN₄N₅N₆ 3' wherein the central CpG motif is unmethylated, D is T, G or A, W is A or T, and $N_1$, $N_2$, $N_3$, $N_4$, $N_5$, and $N_6$ are any nucleotides. In one embodiment, D is a T. The K ODN(s) can be 10 to 30 nucleotides in length. A K ODN can include multiple CpG motifs. In some embodiments, at least one nucleotide separates consecutive CpGs; $N_3D$ is selected from the group consisting of GpT, GpG, GpA, ApT and ApA; $WN_4$ is selected from the group consisting of TpT or CpT; N is any nucleotide and $N_1+N_2$ is from about 0-26 bases In one embodiment, $N_1$, and $N_2$ do not contain a CCGG quadmer or more than one CCG or CGG trimer. CpG ODN are also in the range of 8 to 50 bases in length, such as 8 to 30 bases in length, but may be of any size (even many kb long) if sufficient motifs are present. In several examples, the K-type CpG ODN is 10 to 20 nucleotides in length, such as 12 to 18 nucleotides in length. In one embodiment, synthetic ODNs of this formula do not include a CCGG quadmer or more than one CCG or CGG trimer at or near the 5' and/or 3' terminals and/or the consensus CpG motif is not a palindrome. Other CpG ODNs can be assayed for efficacy using methods described herein. It should be noted that exemplary K-type CpG ODNs are known in the art, and have been fully described, for example in PCT Publication No. WO 98/18810A1, and WO 01/22972, which are incorporated herein by reference. The K type OD can be stabilized.

Exemplary K ODN are listed below:

```
KX                                      (SEQ ID NO: 3)
ATAATCGACGTTCAAGCAAG

K22                                     (SEQ ID NO: 4)
CTCGAGCGTTCTC

K21                                     (SEQ ID NO: 5)
TCTCGAGCGTTCTC

K82                                     (SEQ ID NO: 6)
ACTCTGGAGCGTTCTC

K30                                     (SEQ ID NO: 7)
TGCAGCGTTCTC k31                                     (SEQ ID NO: 8)
TCGAGGCTTCTC

K39                                     (SEQ ID NO: 9)
GTCGGCGTTGAC

K16                                     (SEQ ID NO: 10)
TCGACTCTCGAGCGTTCTC

K3                                      (SEQ ID NO: 11)
ATCGACTCTCGAGCGTTCTC k23                                     (SEQ ID NO: 12)
TCGAGCGTTCTC

K40                                     (SEQ ID NO: 13)
GTCGGCGTCGAC

K34                                     (SEQ ID NO: 14)
GTCGACGTTGAC

K83                                     (SEQ ID NO: 15)
ACTCTCGAGGGTTCTC

K19                                     (SEQ ID NO: 16)
ACTCTCGAGCGTTCTC

K73                                     (SEQ ID NO: 17)
GTCGTCGATGAC

K46                                     (SEQ ID NO: 18)
GTCGACGCTGAC

K47                                     (SEQ ID NO: 19)
GTCGACGTCGAC

K72                                     (SEQ ID NO: 20)
GTCATCGATGCA

K37                                     (SEQ ID NO: 21)
GTCAGCGTCGAC k25                                     (SEQ ID NO: 22)
TCGAGCGTTCT

K82                                     (SEQ ID NO: 23)
ACTCTGGAGCGTTCTC

K83                                     (SEQ ID NO: 24)
ACTCTCGAGGGTTCTC

K84                                     (SEQ ID NO: 25)
ACTCTCGAGCGTTCTA

K85                                     (SEQ ID NO: 26)
CATCTCGAGCGTTCTC

K89                                     (SEQ ID NO: 27)
ACTCTTTCGTTCTC

K109                                    (SEQ ID NO: 28)
TCGAGCGTTCT

K123                                    (SEQ ID NO: 29)
TCGTTCGTTCTC

K1555                                   (SEQ ID NO: 30)
GCTAGACGTTAGCGT

K110                                    (SEQ ID NO: 31)
TCGAGGCTTCTC

CpG10103                                (SEQ ID NO: 32)
TCGTCGTTTTACGGCGCCGTGCCG
```

-continued

CpG7909 (SEQ ID NO: 33)
TCGTCGTTTTGTCGTTTTGTCGTT

K1826 (SEQ ID NO: 34)
TCCATGACGTTCCTGACGTT

CONTROL (not immunostimulatory, used for comparisons)
K1612 (SEQ ID NO: 35)
TAGAGCTTAGCTTGC

K1745 (SEQ ID NO: 36)
TCCATGAGCTTCCTGAGTCT

A single K-type CpG ODN can be used in the methods disclosed herein. In some embodiments, the K-type CpG ODN comprises or consists of the nucleic acid sequence set forth as one of SEQ ID NO: 3-34. The K-type CpG ODN can be any ODN listed above, including but not limited to K1555 or K3. However, it is also possible to use mixtures of K-type CpG ODNs having more than one K-type CpG ODN and an imidazoquinoline compound. Exemplary combinations that can be used include 1) K3, K19, K110; 2) K19, K23, K123; K3, 3) K110, K123; 4) K3, K23, K123; 5) K3, K19, K123; and 6) K19, K110, K123. Additional exemplary combinations include at least two different K-type CpG ODNs, wherein one of the K-type CpG ODNs is K1555, and/or wherein one of the K-type CpG ODNs is K3.

B. D-Type CpG ODN

D-type CpG ODNs also can be used in the method disclosed herein. D-type CpG ODNs (also known as "A" class ODNs) differ both in structure and activity from K-type CpG ODNs (also known as "B" class ODNs) and a third type of ODNs, known as "C" class ODNs. For example, as disclosed herein, D-type CpG ODNs stimulate the release of cytokines from cells of the immune system, and induce the maturation of dendritic cells. In specific, non-limiting examples D-type CpG ODNs stimulate the release or production of interferon inducible protein (IP)-10 and IFN-α by monocytes and/or plasmacytoid dendritic cells.

With regard to structure, in one embodiment, a CpG motif in a D-type CpG ODN has been described by the formula:

$$5' \text{ RY-CpG-RY } 3'$$

wherein the central CpG motif is unmethylated, R is A or G (a purine), and Y is C or T (a pyrimidine). D-type oligonucleotides include an unmethylated CpG dinucleotide. Inversion, replacement or methylation of the CpG reduces or abrogates the activity of the D oligonucleotide.

In one embodiment, a D-type CpG ODN is at least about 16 nucleotides in length and includes a sequence represented by the formula:

(SEQ ID NO: 1)
$$5' \text{ } X_1X_2X_3 \text{ Pu}_1 \text{ Py}_2 \text{ CpG Pu}_3 \text{ Py}_4 \text{ } X_4X_5X_6(W)_m \text{ (G)}_N \text{ } 3'$$

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1 Py_2 CpG Pu_3 Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN, these nucleotides are termed the 5' far-flanking region. Nucleotides 3' of $X_4X_5X_6$ in the D ODN are termed the 3' far-flanking region.

In one specific, non-limiting example, $Py_2$ is a cytosine. In another specific, non-limiting example, $Pu_3$ is a guanidine. In yet another specific, non-limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific, non-limiting example, N is from about 4 to about 8. In another specific, non-limiting example, N is about 6.

In several embodiments, the D-type CpG ODN is at least about 16 nucleotides in length. For example, the D-type CpG ODNs can be from about 16 to about 50 nucleotides in length, or from about 18 to about 50 nucleotides in length, or from about 18 to about 40 nucleotides in length, or from about 18 to about 30 nucleotides in length. Exemplary D-type CpG ODNs are disclosed below. D-type CpG ODNs can include modified nucleotides and/or can be stabilized. For example, modified nucleotides can be included to increase the stability of a D-type CpG ODN.

Without being bound by theory, because phosphothioate-modified nucleotides confer resistance to exonuclease digestion, CpG ODNs are "stabilized" by incorporating phosphothioate-modified nucleotides. In one embodiment, the CpG dinucleotide motif and its immediate flanking regions include phosphodiester rather than phosphothioate nucleotides. In one specific, non-limiting example, the sequence $Pu_1 Py_2 CpG Pu_3 Py_4$ includes phosphodiester bases. In another specific, non-limiting example, all of the bases in the sequence $Pu_1 Py_2 CpG Pu_3 Py_4$ are phosphodiester bases. In yet another specific, non-limiting example, $X_1X_2X_3$ and $X_4X_5X_6(W)_M (G)_N$ include phosphodiester bases. In yet another specific, non-limiting example, $X_1X_2X_3 Pu_1 Py_2 CpG Pu_3 Py_4X_4X_5X_6(W)_M (G)_N$ (SEQ ID NO: 1) include phosphodiester bases. In further non-limiting examples the sequence $X_1X_2X_3$ includes at most one or at most two phosphothioate bases and/or the sequence $X_4X_5X_6$ includes at most one or at most two phosphothioate bases. In additional non-limiting examples, $X_4X_5X_6(W)_M(G)_N$ includes at least 1, at least 2, at least 3, at least 4, or at least 5 phosphothioate bases. Thus, a D ODN can be a phosphothioate/phosphodiester chimera.

As disclosed herein, any suitable modification can be used to render a CpG ODN resistant to degradation in vivo (for example, via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The CpG ODNs can also be modified to contain a secondary structure (e.g., stem-loop structure). Without being bound by theory, it is believed that incorporation of a stem-loop structure renders an oligodeoxynucleotide more effective.

In a further embodiment, $Pu_1$ $Py_2$ and $Pu_3$ $Py_4$ are self-complementary. In another embodiment, $X_1X_2X_3$ and $X_4X_5X_6$ are self-complementary. In yet another embodiment $X_1X_2X_3$ $Pu_1$ $Py_2$ and $Pu_3$ $Py_4$ $X_4X_5X_6$ are self-complementary. Specific non-limiting examples of a D-type CpG ODN wherein $Pu_1$ $Py_2$ and $Pu_3$ $Py_4$ are self-complementary include, but are not limited to, AT<u>CG</u>AT, AC<u>CG</u>GT, AT<u>CG</u>AC, AC<u>CG</u>AT, GT<u>CG</u>AC, or GC<u>CG</u>GC (wherein the CpG is underlined). Thus, in one non-limiting example, the D-type CpG ODN includes the motif $X_1X_2X_3$ AC<u>CG</u>GT $X_4X_5X_6$ (SEQ ID NO: 37), wherein $X_1X_2X_3$ AT and AT $X_4X_5X_6$ are self-complementary. In another non-liming example, the D-type CpG ODN includes the motif $X_1X_2X_3$ AT<u>CG</u>AT $X_4X_5X_6$ (SEQ ID NO: 38), wherein $X_1X_2X_3$ AT and AT $X_4X_5X_6$ are self-complementary.

Without being bound by theory, the self-complementary base sequences can help to form a stem-loop structure with the CpG dinucleotide at the apex to facilitate immunostimulatory functions. Thus, in one specific, non-limiting example, D-type CpG ODNs wherein $Pu_1$ $Py_2$ and $Pu_3$ $Py_4$ are self-complementary induce higher levels of IFN-γ production from a cell of the immune system. The self-complementarity need not be limited to $Pu_1$ $Py_2$ and $Pu_3$ $Py_4$. Thus, in another embodiment, additional bases on each side of the three bases on each side of the CpG-containing hexamer form a self-complementary sequence (see above).

One specific, non-limiting example of a sequence wherein $Pu_1$ $Py_2$ and $Pu_3$ $Py_4$ are self-complementary but wherein the far-flanking sequences are not self-complementary is

GGTGCATCGATACAGGGGGG (DV113, SEQ ID NO: 39, see the Table below)

This oligodeoxynucleotide has a far-flanking region that is not self-complementary and induces high levels of IFN-γ and IFN-α.

Another specific, non-limiting example of a D-type CpG ODN is:

GGTGCGTCGATGCAGGGGGG, (DV28, SEQ ID NO: 40 see the Table below)

This D-type CpG ODN is of use for inducing production and/or release of cytokines from immune cells, although it lacks a self-complementary motif.

In one embodiment, the D-type CpG ODNs are at least about 16 nucleotides in length. In a second embodiment, a D-type CpG ODN is at least about 18 nucleotides in length. In another embodiment, a D-type CpG ODN is from about 16 nucleotides in length to about 100 nucleotides in length. In yet another embodiment, a D-type CpG ODN is from about 16 nucleotides in length to about 50 nucleotides in length. In a further embodiment, a D-type CpG ODN is from about 18 nucleotides in length to about 30 nucleotides in length.

In another embodiment, the D-type CpG ODN is at least 16 nucleotides in length, and at least two G's are included at the 5' end of the molecule, such that the oligodeoxynucleotide includes a sequence represented by the formula:

(SEQ ID NO: 45)
5' $GGX_1X_2X_3$ $Pu_1$ $Py_2$ CpG $Pu_3$ $Py_4$ $X_4X_5X_6(W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10.

The D-type CpG ODN can include additional G's at the 5' end of the oligodeoxynucleotide. In one specific example, about 1 or about 2 G's are included at the 5' end of an oligodeoxynucleotide including a sequence as set forth as the above formula.

Examples of a D-type CpG ODN include, but are not limited to the sequence shown in the following Table 1:

| ODN | SEQUENCE | SEQUENCE IDENTIFIER |
|---|---|---|
| DV113 | GG<u>TGCATCGATA</u>CAGGGGGG | (SEQ ID NO: 39) |
| DV28 | GG<u>TGCGTCGATGCA</u>GGGGGG | (SEQ ID NO: 40) |
| DV104 | GG<u>TGCATCGATGCA</u>GGGGGG | (SEQ ID NO: 41) |
| DV19 | GG<u>TGCATCGATGCA</u>GGGGGG | (SEQ ID NO: 41) |
| DV35 | GG<u>TGCATCGATGCA</u>GGGGGG | (SEQ ID NO: 41) |
| DV29 | GG<u>TGCACCGGTGCA</u>GGGGGG | (SEQ ID NO: 42) |
| DV106 | GG<u>TGTGTCGATGCA</u>GGGGGG | (SEQ ID NO: 43) |
| DV116 | TG<u>CATCGATGCA</u>GGGGGG | (SEQ ID NO: 44) |
| DV34 | GG<u>TGCATCGATGCA</u>GGGGGG | (SEQ ID NO: 41) |
| DV102 | GG<u>TGCATCGTTGCA</u>GGGGGG | (SEQ ID NO: 46) |
| DV32 | GG<u>TGCGTCGACGCA</u>GGGGGG | (SEQ ID NO: 47) |
| DV117 | GG<u>TCGATCGATGCA</u>CGGGGG | (SEQ ID NO: 48) |
| DV37 | GGTGCATCGATGCAGGGGGG | (SEQ ID NO: 49) |
| DV25 | GG<u>TGCATCGATGCAGGGGGG</u> | (SEQ ID NO: 49) |
| DV30 | GG<u>TGCATCGACGCA</u>GGGGGG | (SEQ ID NO: 50) |
| dv120 | GG<u>TGCATCGATAGGC</u>GGGGG | (SEQ ID NO: 51) |
| DV27 | GG<u>TGCACCGATGCA</u>GGGGGG | (SEQ ID NO: 52) |
| dv119 | CC<u>TGCATCGATGCA</u>GGGGGG | (SEQ ID NO: 53) |
| D142 | GG<u>TATATCGATATA</u>GGGGGG | (SEQ ID NO: 54) |
| d143 | GG<u>TGGATCGAT</u>CCAGGGGGG | (SEQ ID NO: 55) |

Underlined bases are phosphodiester. Bold indicates self-complementary sequences. The corresponding sequence identifier is noted. Note that "DV" can also be abbreviated as "D."

Examples of a D-type CpG ODN also include, but are not limited to those in the following Table 2:

(SEQ ID NO: 56)
5'NNTGCATCGATGCAGGGGGG 3'

(SEQ ID NO: 57)
5'NNTGCACCGGTGCAGGGGGG3', (SEQ ID NO: 58)
5'NNTGCGTCGACGCAGGGGGG3', (SEQ ID NO: 59)
5'NNTGCGTCGATGCAGGGGGG3', (SEQ ID NO: 60)
5'NNTGCGCCGGCGCAGGGGGG3',

-continued

5'NNTGCGCCGATGCAGGGGGG3', (SEQ ID NO: 61)

5'NNTGCATCGACGCAGGGGGG3', (SEQ ID NO: 62)

5'NNTGCGTCGGTGCAGGGGGG3', (SEQ ID NO: 63)

wherein N is any base, or is no base at all. In one specific, non-limiting example, N is a G. Additional exemplary D ODN sequences can be found in U.S. Pat. No. 6,977,245 and in Verthelyi et al., *J. Immunol.* 166:2372-2377, 2001, which are both herein incorporated by reference in their entireties. Thus, in some embodiments, the D-type CpG ODN includes, or consists of, the nucleic acid sequence set forth as one of SEQ ID NO: 39-63. The D-type CpG ODN can be any ODN listed above, including but not limited to DV35, DV19, DV28 or DV29.

D-type CpG ODN can be used in combination. Thus, multiple D-type CpG ODNs can be utilized in the methods disclosed herein. For example, two, three, four, five or more D-type CpG ODNs can be utilized to induce an immune response. In addition, a single ODN can be generated that includes the two or more D-type CpG motifs disclosed herein. Thus, DV35, DV19, DV28, DV29 or DV113, or two, three, four or five of these ODNs can be used in combination. In another example, DV35, DV29 and DV19 can be used in combination. Additional exemplary combinations include at least two different D-type CpG ODNs, wherein one of the D-type CpG ODNs is DV35, and/or wherein one of the D-type CpG ODNs is DV28. D-type and K-type CpG ODNs can also be used in combination.

C. C-type CpG ODN and Modifications

C-type ODNs also can be utilized in the methods disclosed herein. Typically, C class ODNs have a TCGTCG motif at the 5' end and have a CpG motif imbedded in a palindromic sequence. M362 is an exemplary C-type CpG ODN that contains a 5'-end 'TCGTCG-motif' and a 'GTCGTT-motif'. C-type ODNs resemble K-type as they are composed entirely of phosphorothioate nucleotides, but resemble D-type in containing palindromic CpG motifs. This class of ODNs stimulates B cells to secrete IL-6 and pDCs to produce IFN-α (see Hartmann et al., Eur. J. Immunol. 33: 1633-41, 2003, incorporated herein by reference). A palindromic sequence of at least 8 nucleotides increases activity, for example a palindrome of at least 12, such as 14, 16, 18 or 20 nucleotides, increases activity. In some embodiments, the CpG-C ODNs include one to two TCG trinucleotides at or close to the 5' end of the ODN and a palindromic region of at least 10-12 bases, which contains at least two additional CG dinucleotides preferably spaced zero to three bases apart. The CG dinucleotides in the palindrome are preferably spaced 1, 2, or 3 nucleotides apart, although sequences with four nucleotide spacings retained low levels of IFN-α-inducing activity (see Marshall et al., J. Leukocyte Biol. 73: 781-792, 2003, incorporated herein by reference). C-type ODNs are present in both early and late endosomes, and thus express properties in common with both K- and D-type CpG ODNs. C-type CpG ODNs include ODN2216, ODN M362, ODN 1668, and ODN2395, which are available from Invivogen and C274, see also Marshall et al., supra.

As noted above, any of the classes of CpG ODN (K, D and C-type ODNs) can be stabilized. In one embodiment, the stabilized oligodeoxyonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

CpG ODN can be synthesized de novo using any of a number of procedures well known in the art. For example, the oligodeoxynucleotides can be synthesized as set forth in U.S. Pat. No. 6,194,388, which is herein incorporated by reference in its entirety.

ODNs can be synthesized using any methods known to those of skill in the art. Automated synthesis of ODNs is routine. An ODN can be synthesized using, for example, the B-cyanoethyl phosphoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

Imidazoquinoline Compounds

Imidazoquinolines are of use in the methods disclosed herein. Imidazoquinolines are synthetic immunomodulatory drugs that act by binding toll-like receptors 7 and 8 (TLR7/TLR8) on dendritic cells, structurally mimicking these receptors' natural ligand, viral single-stranded RNA. Imidazoquinolines are heterocyclic compounds comprising a fused quinoline-imidazole skeleton. Derivatives, salts (including hydrates, solvates, and N-oxides), and prodrugs thereof also are contemplated by the present disclosure. Particular imidazoquinoline compounds are known in the art, see for example, U.S. Pat. No. 6,518,265; and U.S. Pat. No. 4,689,338. In some embodiments, the imidazoquinoline compound is not imiquimod and/or is not resiquimod. In additional embodiments, the imidazoquinoline compound is a lipophilic imidazoquinoline compound.

Certain embodiments of the compound may have a formula as illustrated below:

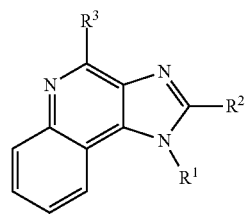

(Formula I)
With reference to Formula I, $R^1$ may be selected from hydrogen, $C_{12-24}$ alkyl, $C_{11-24}$ heteroalkyl, substituted $C_{1-10}$ heteroalkyl, carboxyl, and hydroxyl; $R^2$ may be selected from hydrogen, $C_{1-10}$ alkyl, $C_{1-10}$ heteroalkyl, and substituted $C_{1-10}$ alkyl; and $R^3$ may be selected from hydrogen, amino, aminoacyl, hydroxyl, and $C_{1-10}$ alkoxy.

In particular disclosed embodiments, $R^1$ may be $C_{11-24}$ heteroalkyl, such as $C_{11-24}$ alkoxy (e.g., —$OC_{11-24}$ alkyl), $C_{11-24}$ thioalkyl (e.g., —$SC_{11-24}$ alkyl), and $C_{11-24}$ aminoalkyl (e.g., —$NR^5C_{11-24}$ alkyl, wherein $R^5$ is selected from hydrogen, alkyl, cycloalkyl, aryl, and the like). In other disclosed embodiments, $R^1$ may be $C_{1-10}$ heteroalkyl substituted with one or more substituents selected from amino (e.g., $N(R^5)_2$, wherein each $R^5$ independently is selected from hydrogen, alkyl, cycloalkyl, aryl, and the like), aminoacyl (e.g., —$NC(O)C_{1-30}$ alkyl, —$NC(O)C_{1-23}$ alkyl; such as —$NC(O)C_{11-23}$ alkyl; —$NC(O)C_{15-23}$ alkyl; —$NC(O)C_{15-19}$ alkyl, and —$NC(O)C_{17}$ alkyl), aminocarbonylamino (e.g., —$NC(O)NR^5C_{1-30}$ alkyl, —$NC(O)NR^5C_{1-23}$ alkyl, such as —$NC(O)NR^5C_{11-23}$ alkyl, —$NC(O)NR^5C_{15-23}$ alkyl, —$NC(O)NR^5C_{15-19}$ alkyl, and —$NC(O)NR^5C_{17}$ alkyl), aminocarbonyloxy (e.g., —$NC(O)OC_{1-30}$ alkyl, —$NC(O)OC_{1-23}$ alkyl, such as —$NC(O)OC_{11-23}$ alkyl, —$NC(O)OC_{15-23}$ alkyl, —$NC(O)OC_{15-19}$ alkyl, and —$NC(O)OC_{17}$ alkyl), ether (e.g., —$OC_{1-30}$ alkyl, —$OC_{1-23}$ alkyl, —$OC_{11-23}$ alkyl, —$OC_{15-23}$ alkyl, —$OC_{15-19}$ alkyl, and —$OC_{17}$ alkyl), ester (e.g., —$OC(O)C_{1-30}$ alkyl, —$OC(O)C_{1-23}$ alkyl, such as —$OC(O)C_{11-23}$ alkyl, —$OC(O)C_{15-23}$ alkyl, —$OC(O)C_{15-19}$ alkyl, and —$OC(O)C_{17}$ alkyl), aldehyde (e.g., —$OC(O)H$), carboxyl (e.g., —$OC(O)H$), thioether (e.g., —$SC_{1-30}$ alkyl, —$SC_{1-23}$ alkyl, such as —$SC_{11-23}$ alkyl, —$SC_{15-23}$ alkyl, —$SC_{15-19}$ alkyl, and —$SC_{17}$ alkyl), and thioester (e.g., —$SC(O)C_{1-30}$ alkyl, —$SC(O)C_{1-23}$ alkyl, —$SC(O)C_{11-23}$ alkyl, —$SC(O)C_{15-23}$ alkyl, —$SC(O)C_{15-19}$ alkyl, and —$SC(O)C_{17}$ alkyl).

In particular disclosed embodiments, $R^1$ is —X—Y—Z—$R^6$ wherein X is selected from the group consisting of a bond, —O—, and —NH—; Y is selected from the group consisting of $C_{1-10}$alkyl and $C_{1-5}$alkyl$OC_{1-5}$alkyl; Z is selected from the group consisting of —NHC(O)—, —NHS(O)$_2$—, —NHC(O)NH—; and $R^6$ is —$C_{11-23}$alkyl. In particular disclosed embodiments, Y is $C_{2-10}$ alkyl or Y is $C_{2-4}$ alkyl$OC_{2-4}$ alkyl, with certain embodiments being $C_{2-5}$alkyl. X is selected from a group consisting of a bond and —O— in certain embodiments, with particular disclosed embodiments having X as —O—. In certain embodiments, Z is —NHC(O)—. Particular disclosed compounds may have an $R^6$ substituent that is $C_{15-23}$alkyl, more typically $R^6$ is $C_{15}$-$C_{19}$alkyl.

In particular disclosed embodiments, $R^1$ is selected from the group consisting of —$CH_2CH_2CH_2CH_2CH_2NHC(O)C_{11-23}$ alkyl, —$OCH_2CH_2CH_2CH_2NHC(O)C_{11-23}$ alkyl, —$NHCH_2CH_2CH_2CH_2NHC(O)C_{11-23}$ alkyl, —$CH_2CH_2OCH_2CH_2NHC(O)C_{11-23}$alkyl. More typically, $R^1$ is selected from the group consisting of
—$CH_2CH_2CH_2CH_2CH_2NHC(O)C_{15-23}$alkyl,
—$OCH_2CH_2CH_2CH_2NHC(O)C_{15-23}$alkyl,
—$NHCH_2CH_2CH_2CH_2NHC(O)C_{15-23}$alkyl,
—$CH_2CH_2OCH_2CH_2NHC(O)C_{15-23}$alkyl.

In another disclosed embodiment, the imidazoquinoline compound has the formula:

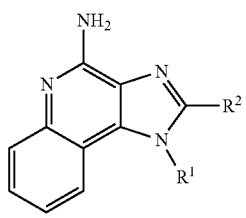

wherein, $R^1$ is selected from —$C_{12-24}$alkyl, —$OC_{11-24}$alkyl, —$NHC_{11-24}$alkyl, and —X—Y—Z—$R^6$, wherein X is selected from the group consisting of a bond, —O—, and —NH—;

Y is selected from the group consisting of $C_{1-10}$alkyl and $C_{1-5}$ alkyl$OC_{1-5}$alkyl Z is selected from the group consisting of:
—NHC(O)—,
—NHS(O)$_2$—,
—NHC(O)NH—; and $R^6$ is —$C_{11-23}$alkyl;

$R^2$ is selected from the group consisting of hydrogen, alkyl, alkylaminoalkyl, alkoxyalkyl, and hydroxyalkyl.

In particular disclosed embodiments, $R^2$ may be $C_{1-10}$ alkyl, such as methyl, ethyl, propyl, butyl, pentyl, hexyl, heptyl, octyl, and the like. In other disclosed embodiments, $R^2$ may be $C_{1-10}$ alkyl substituted with one or more substituents selected from halogen (e.g., chloro, iodo, bromo, fluoro), trihaloalkyl (e.g., trifluoromethyl), aryl (e.g., $C_{6-14}$ aryl), heteroaryl (e.g., $C_{6-14}$ aryl wherein one or more carbon atoms is replaced with a heteroatom selected from oxygen, sulfur, and nitrogen), amino (e.g., —$N(R^5)_2$, wherein each $R^5$ independently is selected from hydrogen, alkyl, cycloalkyl, aryl, and the like), aminoacyl (e.g., —$NC(O)C_{1-10}$ alkyl), aminocarbonylamino (e.g., —$NC(O)NR^5C_{1-10}$ alkyl), aminocarbonyloxy (e.g., —$NC(O)OC_{1-10}$ alkyl), ether (e.g., —$OC_{1-10}$ alkyl), ester (e.g., —$OC(O)C_{1-10}$ alkyl), hydroxyl (—OH), aldehyde (e.g., —$OC(O)H$), carboxyl (e.g., —$OC(O)H$), thioether (e.g., —$SC_{1-10}$ alkyl), and thioester (e.g., —$SC(O)C_{1-10}$ alkyl).

In particular embodiments, $R^2$ is selected from the group consisting of hydrogen, alkyl, alkylaminoalkyl, alkoxyalkyl, and hydroxyalkyl. For example, $R^2$ may be selected from hydrogen, methyl, ethyl, propyl, butyl, ethoxymethyl, methoxymethyl, 2-methoxyethyl, hydroxymethyl, and 2-hydroxyethyl. In certain embodiments, $R^2$ is selected from the group consisting of ethyl, propyl, butyl, methoxyethyl, and ethoxymethyl. In exemplary embodiments, $R^2$ is selected from the group consisting of butyl and ethoxymethyl.

In particular disclosed embodiments, $R^3$ may be amine (—$NH_2$), amino (e.g., —$N(R^5)_2$, wherein each $R^5$ independently is selected from hydrogen, alkyl, cycloalkyl, aryl, heterocyclyl, heteroaryl, and the like), or aminoacyl (e.g., —$NC(O)R^6$ wherein $R^6$ is selected from $C_{1-10}$ alkyl, $C_{1-10}$ haloalkyl, hydrogen, $C_{6-14}$ aryl, and the like).

In other embodiments, the imidazoquinoline compound has a formula:

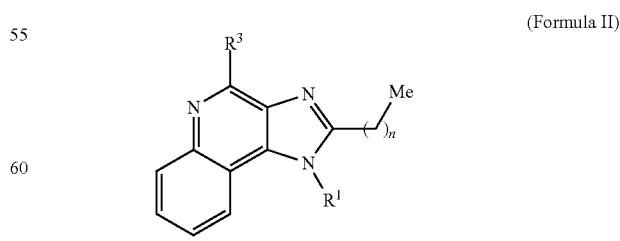

(Formula II)

wherein n ranges from zero to 10; and $R^1$ and $R^3$ may be selected from any of the particular groups recited above for Formula I.

In further embodiments, the imidazoquinoline compound has a formula:

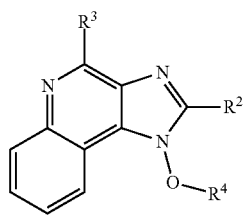

(Formula III)

wherein $R^2$ and $R^3$ may be selected from any of the particular groups recited above for Formula I, and $R^4$ may be selected from $C_{1-10}$ alkyl substituted with one or more of the substituents provided for substituted heteroalkyl, such as those provided for $R^1$ in Formula I, above.

In further embodiments the imidazoquinoline compound is:

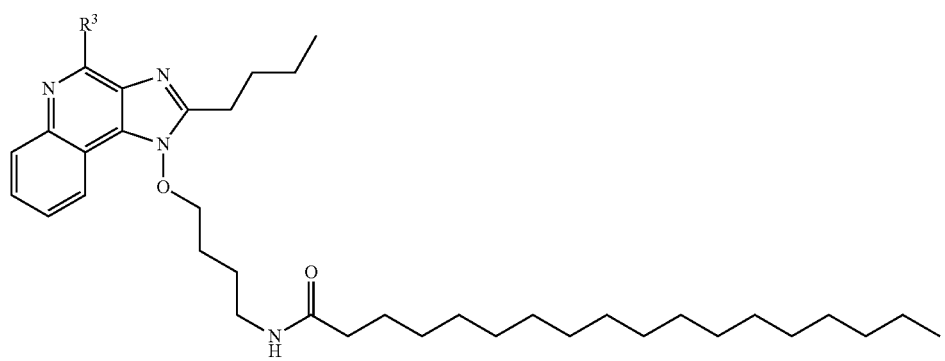

(Formula IV)

(i.e., N-(4-{[4-amino-2-butyl-1H-imidazo[4,5-c]quinolin-1-yl]oxy}butyl) octadecanamide, also known as 3M-052).

Other exemplary imidazoquinoline compounds include the following:

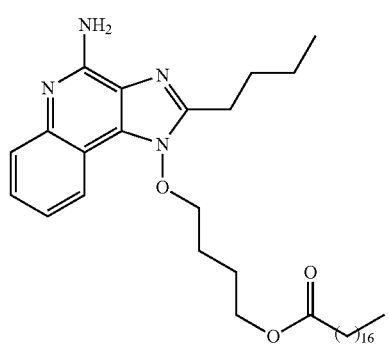

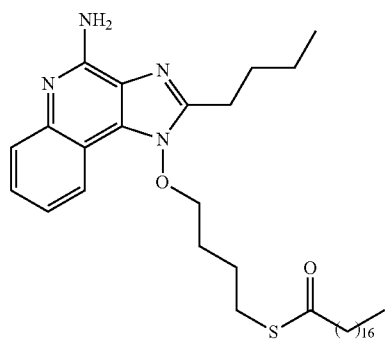

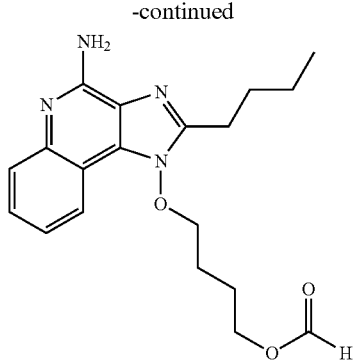

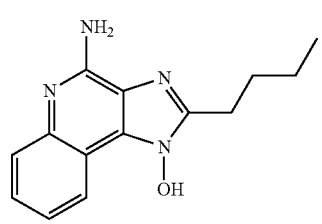

-continued
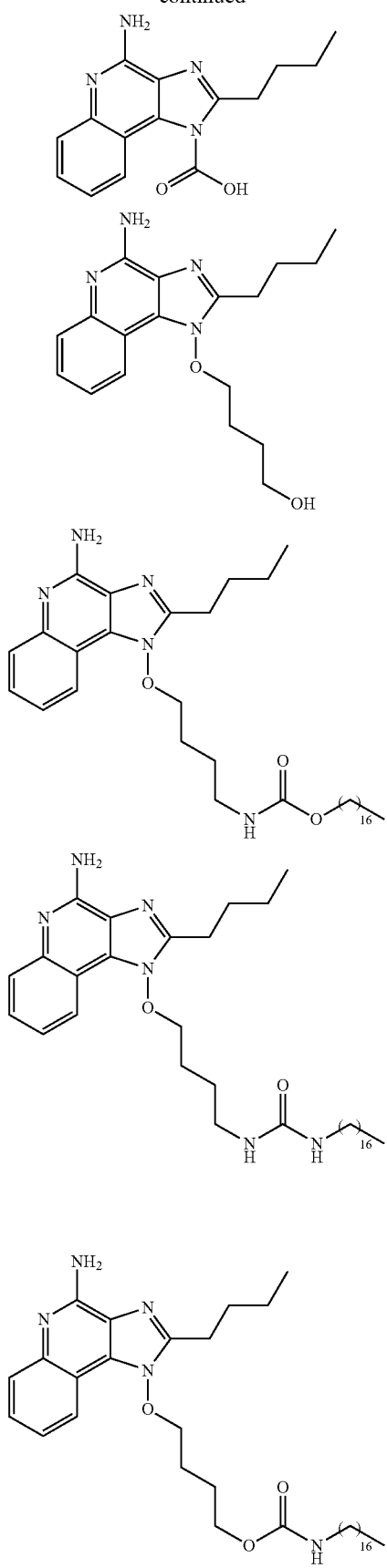
-continued
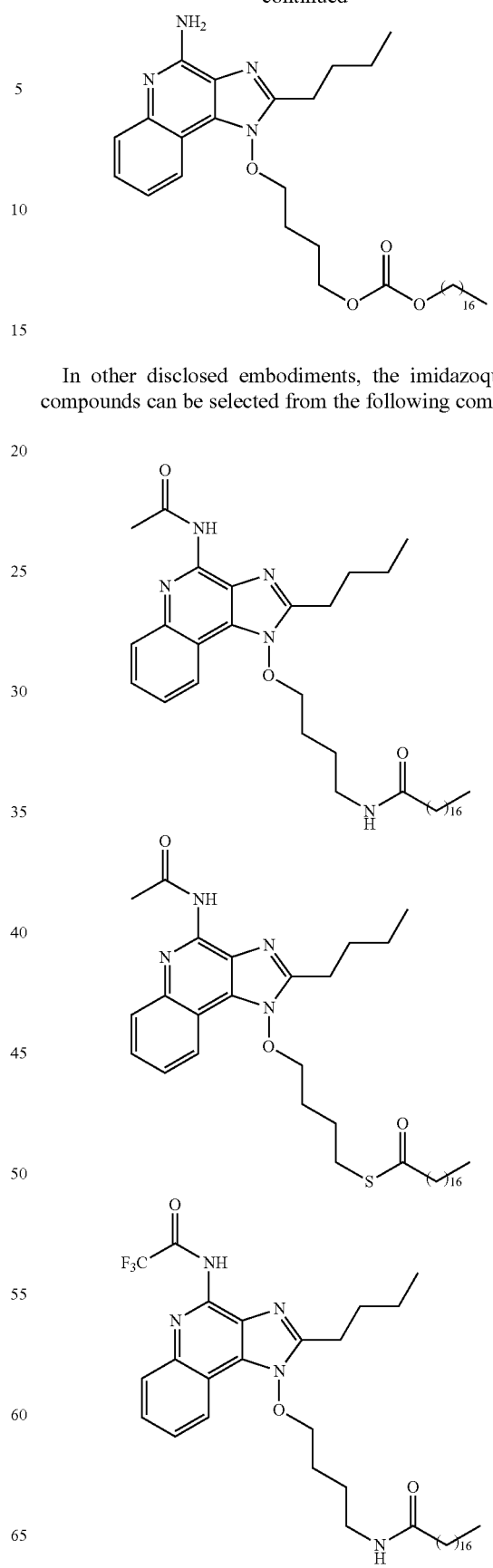
In other disclosed embodiments, the imidazoquinoline compounds can be selected from the following compounds:

-continued

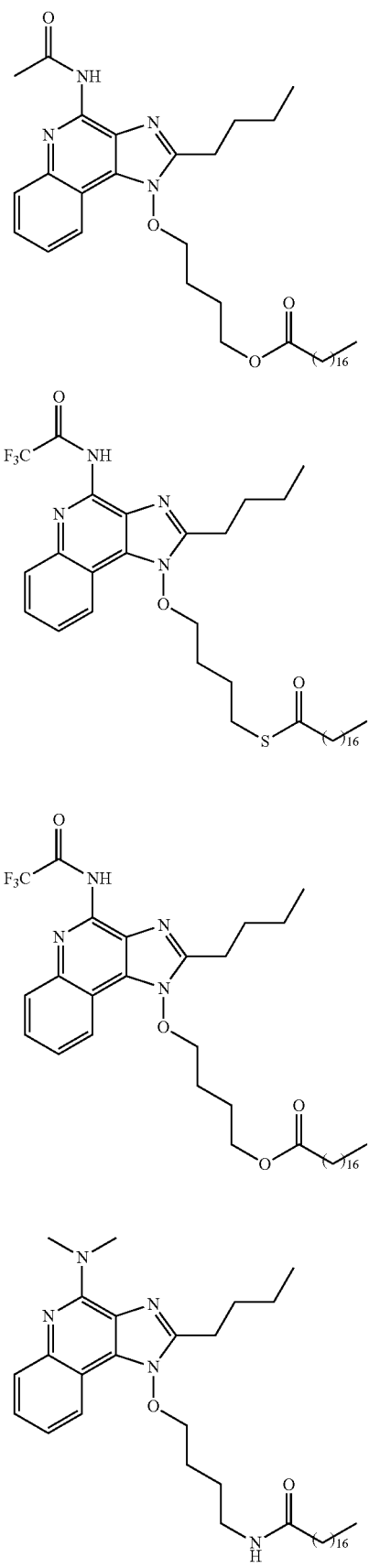

-continued

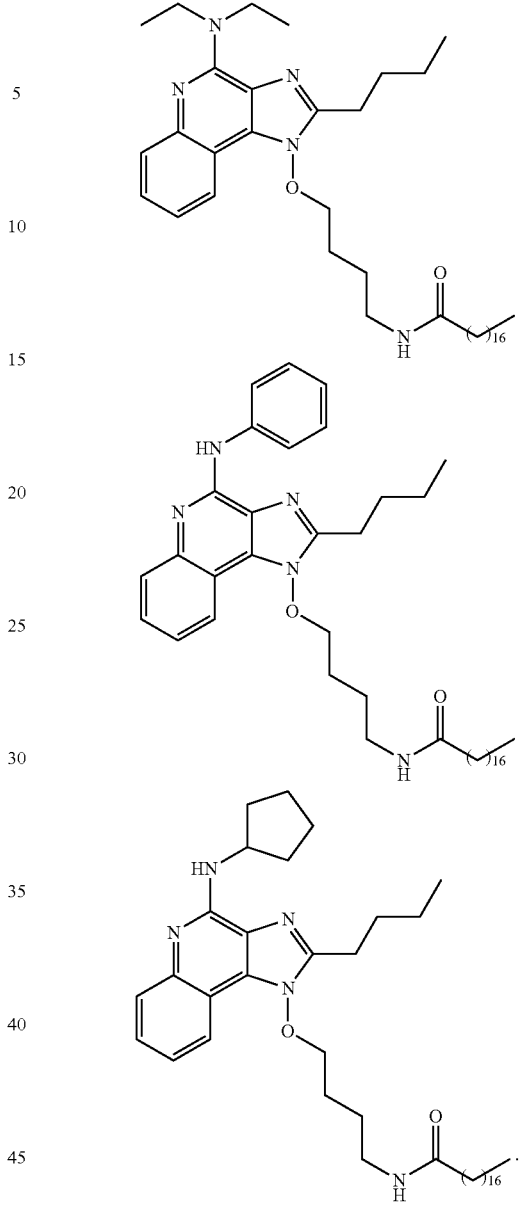

This imidazoquinoline compound can be used in any of its pharmaceutically acceptable forms including solid, semi-solid, solvate (e.g., hydrate), wholly or partially dissolved (such as in a pharmaceutical composition), a prodrug, or dispersed in a pharmaceutically acceptable carrier. Any pharmaceutically acceptable salt of the imidazoquinoline compound can also be used, see PCT Publication No. WO 2012/024284, which is incorporated herein by reference. Additional compounds are disclosed for example, in U.S. Pat. No. 7,799,800, which is incorporated herein by reference.

In particular disclosed embodiments, the pharmaceutically acceptable salt may be selected from any suitable salt known in the art, such as (but not limited to) salts of organic and inorganic counter ions and salts of organic or inorganic acids. In particular disclosed embodiments, the pharmaceutically acceptable salt may be a hydrochloride, hydrobromide, hydroiodide, nitrate, sulfate, bisulfate, phosphate, acetate, lactate, salicylate, citrate, tartrate, bitartrate, ascorbate, succinate, ammonium, potassium, sodium, calcium, magnesium, maleate, fumarate, gluconate, glucaronate, saccharate, formate, benzoate, glutamate, mesylate, tosylate, or besylate salt. One or more of the functional groups provided in any one of Formulas I-III may be manipulated to provide the desired pharmaceutically acceptable salt. Methods of forming pharmaceutically acceptable salts are readily recognized by a person of ordinary skill in the art.

Also disclosed herein are prodrugs of the disclosed compounds. Exemplary prodrug moieties that may be used to functionalize one or more of the functional groups provided in any one of Formulas I-III include, but are not limited to, carbonates, esters, amides, carbamates, oximes, imines, phosphates, and ethers. Methods of forming prodrugs are readily recognized by a person of ordinary skill in the art.

Polyketal Nanoparticles

The compositions disclosed herein use nanoparticle polyketal delivery vehicles for effective targeted delivery of the CPGs to the site of lung tumors. In contrast to PLGA, polyketals degrade into neutral compounds that do not elicit the inflammation associated with polyester based materials. One particular embodiment of the polyketal nanoparticle is a PPADK, PCADK, or a PK nanoparticle such as PK1, 2, 3, 4, 5, or 6, but many different types of polyketal nanoparticles may also be used. The nanoparticles are capable of adsorbing or encapsulating the CPGs and releasing them in the lung at a rate that provides the desired anti-tumor effect.

PPADK has been described in Heffernan and Murthy, *Bioconjugate Chem.* 16:1340-1342 (2005), which is incorporated by reference. PPADK is poly (1,4-phenyleneacetone dimethylene ketal). This polymer has ketal linkages in its backbone and degrades via acid-catalyzed hydrolysis into low molecular weight compounds that can be easily excreted. PPADK form micro- and nano-particles, via an emulsion procedure, and can be used for the delivery of active agents. The PPADK particles degrade without generating acidic degradation products. They degrade on a time scale that is effective for the delivery of the active agents disclosed in the foregoing examples.

The PPADK polymer can be synthesized from 2,2-dimethoxypropane and 1,4-benzene dimethanol. PCADK polyketal polymers are poly (1,4-cyclohexane-acetone dimethylene ketal), which can be synthesized from 2,2-dimethoxypropane and 1,4-cyclohexane dimethanol.

In some embodiments, polyketal polymers are poly (cyclohexane-1,4-diyl acetone dimethylene ketal) (PCADK). PCADK is made from and degrades in an acid sensitive manner into cyclohexane dimethanol and 2,2-dimethoxypropane. Ketal linkages in PCADK typically hydrolyze on the order of weeks under physiologic pH conditions. At the phagosomal pH of 4.5, ketal linkages of PCADK are typically approximately 30% hydrolyzed after 10 days.

Embodiments of polyketal nanoparticles have also been described in U.S. Pat. No. 8,252,846 and WO 2013/163176. In some embodiments described therein, ketal groups include, but are not limited to, the 2,2-dioxypropyl group, 2,2-dioxybutyl group, 1, 1-dioxycyclohexyl group or dioxyacetophenyl group. In some embodiments, ketal polymers include, but are not limited to, aliphatic, cycloaliphatic and/or aromatic ketals containing one or more hetero-atom, such as nitrogen, sulfur, oxygen and/or halides. In other embodiments, the nanoparticles further comprise a compound comprising alkyl, aryl, and/or cycloalkyl groups. In some embodiments, the compound may be directly attached to the ketal group.

In some embodiments, suitable alkyl groups include, but are not limited to, methyl, ethyl and/or butyl groups. In some embodiments, suitable aryl groups include, but are not limited to, substituted and/or unsubstituted benzyl, phenyl and/or naphtyl groups, such as, for example, a 1,4-dimethylbenzene. In some embodiments, suitable cycloalkyl groups include, but are not limited to, substituted or unsubstituted cyclohexyl, cyclopropyl, or cyclopentyl groups, such as, for example, 1,4-dimethylcyclohexyl group.

In some embodiments, hydrolysis kinetics of PCADK derived aliphatic polyketals can be accelerated by increasing their hydrophilic/hydrophobic balance. Examples of such polyketal polymers include, but are not limited to, any one or more of PK1, PK2, PK3, PK4, PK5 and PK6 copolymers. In some embodiments, these six polyketal copolymers exhibit varied hydrolysis kinetics at different pH levels. For example at pH 4.5, PK4 is generally the fastest out of the six copolymers to hydrolyze with PK3 generally having the second fastest hydrolysis rate. In turn, PK3 generally has faster hydrolysis kinetics than PK2 or PK5, while PK2 and PK5 generally have faster hydrolysis kinetics than PK1 or PK6. However, at pH 7.4, PK3 is generally hydrolyzed faster than PK4. Thus, in some embodiments, by altering the copolymer percentage of polyketals, hydrolysis kinetics for controllable release of an active agent can be selectively altered. Methods of making these polyketal polymers are disclosed in Yang et al., *Bioconjug. Chem.* 19:1164-1169, 2008. They were synthesized by copolymerizing 1,4-cyclohexanedimethanol with either 1,4-butanediol, 1,5-pentanediol, 1,6-hexanediol, or 1,8-octanediol. The synthesis was accomplished using the acetal exchange reaction. The PK products were all solids.

TABLE 3

Exemplary Compositions and Molecular Weights of Polyketal Copolymers

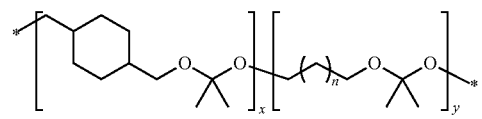

n = 2: PK4
n = 3: PK1, PK2, and PK3
n = 4: PK5
n = 6: PK6

| Polymer ID | Polymer composition | | $M_n$ | PDI* |
|---|---|---|---|---|
| | Monomer diol A (x) | Monomer diol 2 (y) | | |
| PK1 | 1,4-cyclohexanedimethanol (98.03%) | 1,5-pentanediol (1.93%) | 2149 | 1.742 |
| PK2 | 1,4-cyclohexanedimethanol (92.46%) | 1,5-pentanediol (7.56%) | 2530 | 1.629 |
| PK3 | 1,4-cyclohexanedimethanol (86.70%) | 1,5-pentanediol (13.30%) | 2596 | 1.432 |
| PK4 | 1,4-cyclohexanedimethanol (96.75%) | 1,4-butanediol (3.25%) | 2637 | 1.553 |
| PK5 | 1,4-cyclohexanedimethanol (85.32%) | 1,6-hexanediol (14.68%) | 2122 | 1.538 |
| PK6 | 1,4-cyclohexanedimethanol (87.31%) | 1,8-octanediol (12.69%) | 2181 | 1.786 |

*PDI: polydispersity index.

In some embodiments, PK1 has a structure as shown in Table 3 and is made up of at least 2 different monomers. In other embodiments, one type of monomer is 1,4-cyclohexanedimethoxy with an x value (i.e. percent component of the first monomer incorporated into the polymer) of about 98%, and the second type of monomer is 1,5-pentanedioxy with a y value (i.e. percent component of the second monomer incorporated into the polymer) of about 2%. The n value may be 3. In some embodiments, PK1 is synthesized from two types of starting compounds, namely, 1,4-cyclohexanedimethanol and 1,5-pentanediol. An IUPAC designation for PK1 is poly (cyclohexane-1,4-diyl acetone dimethylene ketal-co-1,5-pentane-acetone dimethylene ketal).

In some embodiments, PK2 has a structure as shown in Table 3 and is made up of at least 2 different monomers. In some embodiments, the monomer is 1,4,-cyclohexanedimethoxy with an x value (i.e. percent component of the first monomer incorporated into the polymer) of about 92%, and the second type of monomer is 1,5-pentanedioxy with a y value (i.e. percent component of the second monomer incorporated into the polymer) of about 8%. The n value may be 3. In some embodiments, PK2 is synthesized from two types of starting compounds, namely, 1,4-cyclohexanedimethanol and 1,5-pentanediol. An IUPAC designation for PK2 is poly (cyclohexane-1,4-diyl acetone dimethylene ketal-co-1,5-pentane-acetone dimethylene ketal.

PK3 has been described in Yang et al., *Bioconjug Chem* 2008; 19(6):1164-69. PK3 is a copolymer of 1,4-cyclohexanedimethanol and 1,5-pentanediol that degrades into neutral byproducts of diols and acetone. Specifically, PK3 degrades into its component diols (1,4-cyclohexanedimethanol: LD50=3,200 mg/kg (Rat-oral); 1,5-pentanediol: LD50=10,000 mg/kg (Rat-oral)) and acetone (LD50=5,800 mg/kg (Rat-oral)) which have extremely low toxicity profiles. Furthermore, PK3 undergoes acid-catalyzed hydrolysis, exhibiting a half-life of 1.8 days at a pH of 4.5 versus 39 days at pH=7.4.

In some embodiments, PK3 has a structure as shown in Table 3 and is made up of at least 2 different monomers. In some embodiments, the monomer is 1,4,-cyclohexanedimethoxy with an x value (i.e. percent component of the first monomer incorporated into the polymer) of about 87%, and the second type of monomer is 1,5-pentanedioxy with a y value (i.e. percent component of the second monomer incorporated into the polymer) of about 13%. The n value may be 3. In some embodiments, PK3 is synthesized from two types of starting compounds, namely, 1,4-cyclohexanedimethanol and 1,5-pentanediol. An IUPAC designation for PK3 is poly (cyclohexane-1,4-diyl acetone dimethylene ketal-co-1,5-pentane-acetone dimethylene ketal).

In some embodiments, PK4 has a structure as shown in Table 3 and is made up of at least 2 different monomers. In some embodiments, the monomer is 1,4,-cyclohexanedimethoxy with an x value (i.e. percent component of the first monomer incorporated into the polymer) of about 97%, and the second type of monomer is 1,4-butanedioxy with a y value (i.e. percent component of the second monomer incorporated into the polymer) of about 3%, The n value may be 2. In some embodiments, PK4 is synthesized from two types of starting compounds, namely, 1,4-cyclohexanedimethanol and 1,4-butanediol. An IUPAC designation for PK4 is poly (cyclohexane-1,4-diyl acetone dimethylene ketal-co-1,4-butane-acetone dimethylene ketal).

In some embodiments, PK5 has a structure as shown in Table 3 and is made up of at least 2 different monomers. In some embodiments, the monomer is 1,4,-cyclohexanedimethoxy with an x value (i.e. percent component of the first monomer incorporated into the polymer) of about 85%, and the second type of monomer is 1,6-hexanedioxy with a y value (i.e. percent component of the second monomer incorporated into the polymer) of about 15%. The n value may be 4. In some embodiments, PK5 is synthesized from two types of starting compounds, namely, 1,4-cyclohexanedimethanol and 1,6-hexanediol. An IUPAC designation for PK5 is poly (cyclohexane-1,4-diyl acetone dimethylene ketal-co-1,6-hexane-acetone dimethylene ketal).

In some embodiments, PK6 has a structure as shown in Table 3 and is made up of at least 2 different monomers. In one example of PK6, the monomer is 1,4,-cyclohexanedimethoxy with an x value (i.e. percent component of the first monomer incorporated into the polymer) of about 87%, and the second type of monomer is 1,8-octanedioxy with a y value (i.e. percent component of the second monomer incorporated into the polymer) of about 13%. The n value may be 6. In some embodiments, PK6 is synthesized from two types of starting compounds, namely, 1,4-cyclohexanedimethanol and 1,8-octanediol. An IUPAC designation for PK6 is poly (cyclohexane-1,4-diyl acetone dimethylene ketal-co-1,8-octane-acetone dimethylene ketal).

One or more PK1-PK6 copolymers may be synthesized using the acetal exchange reaction by copolymerizing 1,4-cyclohexanedimethanol with either butanediol, pentanedial, hexanediol or octanediol. As shown in Table 3, a PK1 was synthesized with monomer A (1,4-cyclohexanedimethanol) plus monomer B (1,5-pentanediol); a PK2 was synthesized with monomer A (1,4-cyclohexanedimethanol) plus monomer B (1,5-pentanediol); a PK3 was synthesized with monomer A (1,4-cyclohexanedimethanol) plus monomer B (1,5-pentanediol); a PK4 was synthesized with monomer A (1,4-cyclohexanedimethanol) plus monomer B (1,4-butanediol); PK5 was synthesized with monomer A (1,4-cyclohexanedimethanol) plus monomer B (1,6-hexanediol); a PK6 was synthesized with monomer A (1,4-cyclohexanedimethanol) plus monomer B (1,8-octanediol), In some embodiments, PK1, PK2, PK3, PK4, PK5 and/or PK6 copolymers can be intermingled to change or fine tune the release rate profile for attached active agents. For example, a polyketal with fast hydrolysis kinetics (e.g., PK4 or PK3) can be mixed with a polyketal with slower hydrolysis kinetics (e.g., PK1 or PK6) and co-administered to a subject. In general, an active agent joined to PK4 or PK3 will be released in a subject quickly to provide the subject with an immediate release (IR) dose of active agent, while an active agent joined to PK1 or PK6 will be released at a slower rate allowing a gradual or extended release (ER) of the active agent in the subject.

In some embodiments, biodegradable hydrophobic polyketal polymers comprise (1) multiple ketal groups, each ketal group having two oxygen atoms within the polymer backbone and (1) a linker. Ketal groups may comprise a 2,2-dioxypropyl group.

In other embodiments, the polyketal is one such as those disclosed in U.S. Pat. No. 7,951,898 comprising repeat structural units, wherein substantially all the structural units comprise (i) at least one ketal group wherein at least one ketal oxygen atom is within the polymer main chain; and (ii) at least one hydrophilic group or pharmaceutically useful group. In another aspect of the invention, at least a subset of the repeat structural units have the following chemical structure:

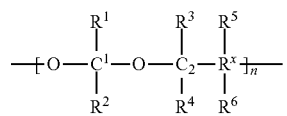

wherein n refers to the number of ketal moieties in the molecule, wherein n is an integer larger than 1, and each occurrence of $R^1$ and $R^2$ is a biocompatible group and includes a carbon atom covalently attached to $C^1$; RX includes a carbon atom covalently attached to $C^2$; n is an integer; each occurrence of $R^3$, $R^4$, $R^5$ and $R^6$ is a biocompatible group and is independently hydrogen or an organic moiety; and for each occurrence of the bracketed structure n, at least one of $R^1$, $R^2$, $R^3$, $R^4$, $R^5$ and $R^6$ is either hydrophilic or pharmaceutically useful.

In yet another aspect, the biodegradable biocompatible polyketals of the invention comprise repeat structural units having the following chemical structure:

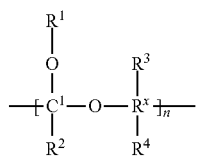

wherein n refers to the number of ketal moieties in the molecule, wherein n is an integer larger than 1, and each occurrence of $R^2$ is a biocompatible group and includes a carbon atom covalently attached to $C^1$; RX includes a carbon atom covalently attached to C'; n is an integer; each occurrence of $R^1$, $R^3$ and $R^4$ is a biocompatible group and is independently hydrogen or an organic moiety; and for each occurrence of the bracketed structure n, at least one of $R^1$, $R^2$, $R^3$ and $R^4$ is either hydrophilic or pharmaceutically useful.

There is generally no requirement that all such ketal moieties be connected to each other directly, or that the molecule be strictly regular and consist only of the repeat structures depicted above. For example, the bracketed structures may not necessarily be positioned in a head-to-tail fashion throughout the polymeric chain. Irregularities may exist in the polymer backbone, whereby, for example, a number of monomeric units differ from the general structures depicted above. In addition, where the polyketals of the invention are prepared from co-polymerization of at least two monomers or from a polysaccharide comprising more than one type of saccharide moiety, the group of substituents ($R^1$-$R^5$) in each structural unit of the polymeric chain may not be identical throughout the polymer and they may vary from one structural unit to the next. For the purpose of the invention, it is to be understood that the substitutents $R^1$-$R^5$ as used herein may be the same or different throughout the polymer structure. In addition, the structures of the polyketals of the invention are not limited to that depicted herein. The invention broadly encompasses polyketals structures wherein at least one ketal oxygen belongs to the main chain, and wherein substantially all monomeric units comprise at least one hydrophilic group or a pharmaceutically useful group.

In other embodiments, the polyketal nanoparticle is biodegradable hydrophobic polyketal polymers comprising multiple ketal groups, each ketal group having two oxygen atoms within the polymer backbone. In some embodiments, provided nanoparticle compositions comprise biodegradable hydrophobic polyketal polymers that are in the form of a solid molecule.

In some embodiments, polyketal polymer particles can further comprise one or more active agents. In some embodiments, a polyketal polymer particle can further comprise one or more linkers which can bind an active agent. Multiple linkers of the same or different types can be attached to a polymer particle. In some embodiments, linkers are attached to particle surfaces. In some embodiments, linkers are exposed to solvent or aqueous solution surrounding the particles. In other embodiments, the active agent is encapsulated by the nanoparticle or adsorbed to the surface of the nanoparticle.

In further embodiments, the polyketal nanoparticles are freeze dried. In some embodiments, freeze drying results in aggregation of polyketal nanoparticles, such that a microparticle aggregate is formed. These microparticles, formed of polyketal nanoparticles, can be used in any of the methods disclosed herein.

Pharmaceutical Compositions and Methods of Use

Methods are disclosed herein for producing an immune response to a lung cancer in a subject. Methods are also provided for treating a lung cancer in a subject. In some embodiments, the methods include treating an existing lung cancer in a subject. In additional embodiments, methods are disclosed herein are used for preventing metastasis in a subject. The subject can be a smoker, such as current smoker or an ex-smoker, or the subject can be a non-smoker.

In some embodiments, the methods reduce a symptom of the lung cancer in the subject. In additional examples, the lung cancer is SCLC or NSCLC. The non-small cell lung cancer can be squamous cell lung carcinoma (SQCC), adenocarcinoma (ADC), and large cell lung carcinoma. Generally, the methods include selecting a subject having a lung cancer, such as a NSCLC or a SCLC, and administering to the subject a therapeutically effective amount of a polyketal nanoparticle include (1) a CpG ODN, such as K-type CpG ODN, D-type CpG ODN, C-type CpG ODN, or a combination thereof; and optionally (2) an imidazoquinoline compound. In any of the embodiments disclosed herein, the imidazoquinoline compound can be a lipophilic imidazoquinoline compound, such as 3M-052. In any of the embodiments disclosed below, the CpG ODN can be one of SEQ ID NOs: 3-34 or 39-65; combinations thereof can also be used. Exemplary methods are disclosed below.

The methods are of use for treating the lung cancer and/or reducing metastasis and/or preventing metastasis. The administration can be local, such as by regulating the size of the particle (such as a nanoparticle) that delivers the drug, and/or administering the particle by inhalation. In some examples, more than one CpG ODN is included in the polyketal particle, such as two, three, four or five CpG ODN. These ODNs can be of the same type or can be different types. Optionally, one or more imidazoquinoline compounds are also included in the polyketal particle, such as a polyketal nanoparticle or polyketal microparticle (for example, aggregated polyketal nanoparticles).

Additional agents can also be administered to the subject of interest, such as, but not limited to, chemotherapeutic agents. Additional treatments can also be administered to the subject, such as, but not limited to, surgical resection of the lung cancer.

Treatment of the lung cancer, such as NSCLC, is generally initiated after the diagnosis of the lung cancer. The subject can have stage 0, IA (one-A), IB, IIA, IIB, IIIA, or any of stages IIIB to IV. The assessment can be made using TMN classification to identify stage T1a, T1b, T2a, T2b, T3 size, T3 inv, T3 centr, T4 inv, T4 ipis, N1 or N2. TMN is the staging system used by the American Joint Committee on Cancer and International Union against Cancers that uses the size of the primary tumor and whether it has invaded normal tissue (T), involvement of lymph nodes (N) and metastasis (M). A subject with any stage of lung cancer can be treated using the method disclosed herein.

The presence of lung cancer, such as NCSLC, can be determined by methods known in the art, such as a CT scan, a PET scan, endoscopic ultrasound and/or endobronchial ultrasound. Pulmonary function tests can also be used. The lung cancer can also be diagnosed by obtaining one or more biopsies and evaluating the cells in the biopsy.

Treatment can result in decreasing the severity of the symptoms of the lung cancer, or completely removing the symptoms, or reducing metastasis, tumor volume or number of tumors. In some embodiments, the tumor becomes undetectable following treatment. Symptoms include respiratory symptoms, such as coughing, coughing up blood, wheezing and/or shortness of breath, systemic symptoms such as weight loss, fever, or fatigue, or symptoms due to local compression, such as chest pain, bone pain, or difficulty swallowing. There can also be a reduction in parapneoplastic phemonena such as Lambert-Eaton myasthenic syndrome, hyercalcemia, syndrome of inappropriate antidiuretic hormone (SIADH), or Horner's symdrome.

Treatment can also include increasing the immune response to the lung cancer, such as by increasing the humoral response, or cytokines, NK cells, activated CTLs, such as CD8$^+$ T cells, or MDSCs, such as mMDSCs. Treatment can also reduce the number of regulatory T cells.

In one non-limiting example, the formation of tumors, such as metastasis, is delayed, prevented or decreased. In another non-limiting example, the size of the primary tumor is decreased. In yet another non-limiting example, a symptom of the tumor is decreased. In yet another non-limiting example, tumor volume is decreased. In a further non-limiting example, the lung cancer is NSCLC.

In some embodiments, a therapeutically effective amount of a polyketal particle, such as a polyketal nanoparticle including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound, for example, 3M-052, and is administered to the subject. Exemplary K-type CpG ODN, D-type CpG ODN and C-type ODN are listed above, see for example, SEQ ID NOs: 3-34 and 39-63. In additional embodiments, an immune response can be measured, tumor volume can be measured, the number of metastatic lesions can be measured, or a symptom can be measured. A therapeutically effective dose can increase the immune response, decrease tumor volume, decrease the number and/or size of metastases, and/or decrease one or more symptoms of the lung cancer. A microparticle comprised of polyketal nanoparticles can be utilized.

Pharmaceutical compositions of use include a polyketal particle, such as a nanoparticle, including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound, for example, 3M-052. These compositions can also include an additional agent, such as an additional chemotherapeutic agent. In some embodiments, the composition includes 3M-052. The pharmaceutical compositions can include a polyketal nanoparticle of a particular size, such as about 150 to about 500 nm in size, such as about 175 nm to about 450 nm in size, such as about 200 to about 400 nm in size. In some embodiments, the pharmaceutical compositions can include a polyketal nanoparticle of a particular size, such as 150 to 500 nm in size, such as 175 nm to 450 nm in size, such as 200 to 400 nm in size. The pharmaceutical composition can include microparticles that include or consist of the nanoparticle. The microparticles can be, for example, about 0.5 to about 30 μm in diameter, about 0.75 μm to about 20 μm in diameter, about 1 μm to about 10 μm in diameter, about 1 μm to about 5 μm in diameter, or about 1 μm to about 3 μm in diameter, for example about 1 μm to about 2 μm in diameter. In some embodiments, the microparticles can be, for example, 0.5 to 30 μm in diameter, 0.75 μm to 20 μm in diameter, 1 μm to 10 μm in diameter, 1 μm to 5 μm in diameter, or 1 μm to 3 μm in diameter, for example 1 μm to 2 μm in diameter. Thus, in some embodiments, the disclosed nanoparticles, or microparticles including or consisting of these nanoparticles, are used for the treatment of lung cancer in a subject. In certain examples, the microparticles comprised of the nanoparticles are used for intratracheal administration.

For administration by inhalation, polyketal nanoparticles or microparticles can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, a polyketal nanoparticle or microparticle can be administered by inhalation. For example, the polyketal nanoparticle or microparticle can be administered in an aerosolized form, such as using a nebulizer or a metered dose inhaler. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMIST®), and ultrasonic nebulizers (such as the DeVilbiss ULTRA-NEB®).

The polyketal nanoparticle or microparticle can be dissolved in a carrier, such as saline, and atomized using the devices above. The associated aerosols can be collected using a NEXT GENERATION IMPACTOR® (NGI) (MSP Corp., Shoreview, Minn.), which uses a series of aerodynamic stages to separate and collect the aerosol into separate fractions based on droplet size. Since droplet size is the primary determinant of deposition location in the lungs, this device allows us to specifically isolate the portion of the liquid aerosol that will deposit in the small airways and alveoli.

Aerosol particle size is often expressed in terms of mass median aerodynamic diameter (MMAD), a parameter that is based on particle size, shape, and density. For a spherical particle, MMAD is equal to MMD ($p^{1/2}$), in which MMD is mass median diameter and r is the bulk density. For a non-spherical particle, MMAD is equal to MMD $(p/x)^{1/2}$, in which X is the shape factor. Thus, particles with larger than unit density will have actual diameters smaller than their MMAD.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

While the disclosed methods and compositions will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

The compositions or pharmaceutical compositions can include a polyketal nanoparticle including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound, for example, 3M-052, which can be administered locally, such as by pulmonary inhalation or intra-tracheal delivery. When polyketal nanoparticles are provided, or microparticles including or consisting of these polyketal nanoparticles are provided, e.g. for inhalation or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

The pharmaceutically acceptable carriers and excipients useful in the disclosed methods are conventional. For instance, formulations usually comprise fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The formulations can be prepared by combining a polyketal nanoparticle including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound, for example, 3M-052 uniformly and intimately with liquid carriers or finely divided solid carriers or both. The formulations can also be prepared by combining microparticles including or consisting of the polyketal nanoparticles uniformly and intimately with liquid carriers or finely divided solid carriers or both.

The pharmaceutical compositions that comprise a polyketal particle, such as microparticles or nanoparticles, including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound such as 3M-052, can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. As disclosed in particular embodiments, therapeutically effective amounts of a polyketal nanoparticle including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound such as 3M-052, and/or a therapeutically effect amounts of microparticles including these nanoparticles, are of use for inducing an immune response to the lung cancer cells, treating a tumor, and/or preventing conversion of a benign to a malignant lesion, or preventing metastasis. Administration may begin whenever appropriate as determined by the treating physician.

The therapeutically effective amount will be dependent on the CpG ODN(s) utilized, the subject being treated, the severity and type of the affliction, and the manner of administration. The exact dose is readily determined by one of skill in the art based on the potency of the specific compound (such as the ODN utilized and the imidazoquinoline compound), the age, weight, sex and physiological condition of the subject. For example in a mouse model, 2 to 100 μg CpG ODN/body weight was used, and an acceptable dose of 50 μg CpG ODN/body weight was selected (=2 μg/g=2 mg/kg). As an example in humans, a CpG dose of 1-1000 μg would be administered intratracheally or delivered to the lungs in each intratracheal dosage. The dosage could be repeated, for example on multiple different days, such as daily weekly or monthly, for a desired duration of treatment.

In other examples, suitable concentrations of the CpG would include, but are not limited to, about 1 to about 100 μg/gm K-type CpG ODN, such as about 2 5 to about 50 μg/gm, such as about 10 μg/gm CpG ODN. Additional suitable concentrations include 1 to 100 mg/kg, such as about 5 to about 50 mg/kg, such as about 10 mg/kg. Suitable doses also include about 0.1 to about 2 mg/kg in humans.

Doses of the CpG oligonucleotide may be repeated as needed to achieve therapeutic doses at the target tissue, such as the lungs, for example in the terminal bronchi or distal alveoli.

In other embodiments about 0.1 to about 10 mg/kg of the imidazoquinoline compound is administered, such as about 0.1 to about 1 mg/kg. In specific non-limiting examples, about 0.5 to about 5 mg/kg, about 1 to about 5 mg/kg, about 0.5 to 2 mg/kg, or about 1 mg/kg, about 2 mg/kg, about 3 mg/kg, about 4 mg/kg, or 5 mg/kg of the imidazoquinoline compound is administered. In certain embodiments, the dose of the imidazoquinoline compound is 2-250 μg administered intratracheally or delivered to the lungs. This dose could be repeated as necessary to achieve desired concentrations. As with the CpG, the dosage could be repeated, for example on multiple different days, such as daily weekly or monthly, for a desired duration of treatment.

The polyketal nanoparticle can provide a fixed dose formulation of the CpG oligonucleotide and the imidazoquinoline. In some examples, the dose of the CpG in the formulation is about 2-4 time greater than the dose of the imidazoquinoline. For example, the dose ratio of CpG to the imidazoquinoline is in the range of 2:1 to 4:1, for example 1000 µg of the CpG and 250 µg of the imidazoquinoline. In other embodiments the CpG oligonucleotide and imidazoquinoline are administered separately but concurrently (at substantially the same time) on different particles.

Thus, pharmaceutical compositions are provided that include a therapeutically effective amount of a polyketal nanoparticle including (1) one or more CpG ODN, such as K-type CpG ODN, D-type CpG ODN, C-type CpG ODN, or a combination thereof, and optionally (2) an imidazoquinoline compound, such as a lipophilic imidazoquinoline compound, for example, 3M-052, and/or microparticles including these nanoparticles. The polyketal nanoparticles can be of a specific size, as discussed above. Microparticles, such as microparticles including these nanoparticles, also can be of a specific size as discussed above.

Additional agents can be administered to the subject, such as a cytokine, a chemokine, or a chemotherapeutic agent. These can be included in the disclosed pharmaceutical compositions. A cytokine can be administered, such as interleukin-2 (IL-2), granulocyte macrophage colony stimulating factor (GM-CSF), or interferon, such as interferon (IFN) β. In one example, for the prevention and treatment of cancer, surgical treatment can be administered to the subject. In one example, this administration is sequential. In other examples, this administration is simultaneous.

Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

In some embodiments, the subject has NSCLC, and the subject is administered single agent or a combination of ALIMTA® (Pemetrexed Disodium), AVASTIN® (Bevacizumab), Gefitinib, GILOTRIF® (Afatinib Dimaleate), GEMZAR® (Gemcitabine Hydrochloride), IRESSA® (Gefitinib), Methotrexate, TAXOL® (PaclitaxelABRAXANE® (Paclitaxel Albumin-stabilized Nanoparticle Formulation), PARAPLAT® (Carboplatin), PARAPLATIN® (Carboplatin), Pemetrexed Disodium, PLATINOL® (Cisplatin), PLATINOL-AQ® (Cisplatin), TARCEVA® (Erlotinib Hydrochloride), TAXOTERE® (Docetaxel), XALKORI® (Crizotinib), and ZYKADIA® (Ceritinib In other embodiments, the subject has small cell lung cancer and is administered one or more of ABITREXATE® (Methotrexate), ETOPOPHOS (Etoposide Phosphate), Etoposide, Etoposide Phosphate, FOLEX® (Methotrexate). FOLEX PFS® (Methotrexate), HYCAMTIN® (Topotecan Hydrochloride), Methotrexate, METHOTREXATE LPF® (Methotrexate), MEXATE (Methotrexate), MEXATE-AQ® (Methotrexate), TOPOSAR® (Etoposide), Topotecan Hydrochloride, and VEPESID® (Etoposide).

The subject can be administered an immunotherapy. In some embodiments, the subject is administered a PD-1 antagonist, such as antibody that specifically binds PD-1 or PD-L1, such as MPDL3280A. In other embodiments, the subject is administered ERBITUX® (cetuximab).

This disclosure is illustrated by the following non-limiting examples:

EXAMPLES

One strategy to trigger the innate immune system involves activating cells that express Toll-like receptors (TLRs). Synthetic oligonucleotides expressing unmethylated CpG motifs (CpG ODN) provided substantial anti-tumor activity and activation of cells bearing TLR9 (Krieg A M. *J Clin Invest* 2007; 117:1184-1194). In a murine model of Lewis lung cancer, administering CpG ODN in combination with chemotherapy significantly prolonged survival (Weeratna et al., *J Clin Oncol* 2004; 22 (Suppl): 699. Abstract 7346). Based on considerable preclinical data, clinical trials assessing the safety and efficacy of systemically administered CpG ODN were conducted in patients with advanced NSCLC (Manegold et al., *J Clin Oncol* 2008; 26:3979-3986, Yamada et al., *Cancer Sci* 2010; 101:188-195). While favorable results were observed in the phase 2 studies, no survival benefit was observed in the definitive phase 3 trials of CpG ODN in patients with NSCLC (Hirsh et al., *J Clin Oncol* 2011; 29:2667-2674, Manegold et al., *Ann Oncol* 2012; 23:72-77). When assessing the data from those studies, it is noteworthy that the objective response rate of patients who received CpG ODN exceeded that of patients receiving chemotherapy alone (28-30% vs 19-23%).

As disclosed below, it is possible that systemically administered CpG ODN has only limited time to reach pulmonary tumors and trigger an innate immune response, because CpG ODN were rapidly cleared from the body (median $t_{max}$ of 2 h and mean $t_{1/2} \approx 12$ h) (Yamada et al., *Cancer Sci* 2010; 101:188-195). It was determined whether intrapulmonary delivery would increase the effectiveness of CpG ODN.

To improve tumor targeting and pulmonary retention, the CpG ODN were adsorbed onto polymer-based polyketal nanoparticles (NP). Polyketal NP are biodegradable and can be formulated into microparticles of optimal size for delivery to distal bronchi (Heffernan et al., *Bioconjug Chem* 2005; 16:1340-2, Fiore et al., *Biomaterials* 2010; 31:810-7).

When CpG ODN adsorbed onto NP were delivered intratracheally to mice with Lewis lung cancer (a model of human NSCLC), they accumulated and persisted in the tumor microenvironment. This treatment promoted the development of an inflammatory reaction and reduced the frequency of immunosuppressive $T_{reg}$, culminating in a significant reduction in tumor burden and long-term survival. These results presented below show that local therapy using CpG-NP can be used to treat lung cancer.

Example 1

Materials and Methods

Preparation of Polyketal Nanoparticle (NP): The poly-(1, 4-phenyleneacetone dimethylene ketal) matrix of the nanoparticles was synthesized by Celagix Res Ltd. (Yokohama, Japan). Polyvinylalcohol (PVA, Sigma, St. Louis, Mo.) was used as a dispersing agent. Polyketal NP were produced via an acetal exchange reaction as previously described (Heffernan M J. *Bioconjugate Chem* 2005; 16:1340, Heffernan M J. *Biomaterials* 2009; 30:910). Briefly, 1,4-benzenedimethanol (10 g, 36 mmol) and 1,5-pentanediol (1.8 g, 8.67 mmol) were dissolved in ethyl acetate and added to the 100 mL of methylbenzene. Recrystallized p-toluenesulfonic acid (520 mg, 2.93 mmol) in 1.0 mL of ethyl acetate was then added followed by 2,2-dimethylpropane (9 mL, 37 mmol) to initiate the reaction. Additional 2,2-dimethylpropane (9 mL, 37 mmol) and methylbenzene were added to the reaction every 30 min for 2 h. After 12 h, the polymer was isolated by precipitation in ice cold hexane (−20° C.) followed by vacuum filtration.

Preparation of CpG ODN Adsorbed Polyketal NP: The phosphorothioate ODN used in this study were CpG 1555 (GCTAGACGTTAGCGT, SEQ ID NO: 30) and control ODN 1612 (GCTAGAGCTTAGCGT, SEQ ID NO: 35). These were synthesized by IDT Technologies (Coralville, Iowa). ODN were adsorbed onto polyketal NP using the water-in-oil-in-water double emulsion solvent evaporation method (Tahara K. *Int J Pharmacol* 2008; 354:210). ODN dissolved in water was added to DOTAP solution (Avanti, Alabaster, Ala.) at a 1:1 (w/w) ratio with stirring. The ODN/DOTAP complexes were added to a 0.5% w/v PVA solution in 10 mM sodium bicarbonate and then mixed with a solution of polyketal (500 mg) dissolved in 5 mL of dichloromethane. The mixture was emulsified by sonication (Sonifier 250, Branson, USA, Duty cycle 80%, Output 5) for 3 min. The resulting emulsion was added to 125 mL of a 1% PVA solution and agitated with stirring at 500 rpm for 6 h to remove dichloromethane. The ODN-loaded polyketal NP were collected by centrifugation at 4,500 rpm for 10 min, washed with 10 mM sodium bicarbonate and then freeze-dried. All materials in this study were endotoxin free as determined by *Limulus* amebocyte cell lysate assay (Cambrex Bioscience, Walkersville, Md.; sinsitivity 0.1 U endotoxin/mg).

The release of CpG ODN from CpG-NP was determined by dissolving in physiological saline (pH 7.4, 37° C.). Supernatants were collected over time, centrifuged at 4500 rpm for 10 min and loaded onto a 3% agarose gel. Gel electrophoresis was performed at a constant 100 V for 0.5 h and ODN was visualized by SYBR staining (Invitrogen) in comparison to serial dilutions of free ODN. Loading efficiency (%) was calculated by the formula: (maximal release of ODN from poyketal NP)/(weight of ODN used in synthetic process)×100%.

Analysis of CpG-NP Size: CpG-NP samples were suspended in physiological saline, transferred onto carbon tape, and dried. They were then coated with a 30 nm layer of osmium using an osmium plasma coater (NL-OPC80NS, Nippon Laser & Electronics Laboratory, Japan), and visualized by scanning electron microscopy (JSM-6340F) at an acceleration voltage of 5.0 kV.

CpG-NP samples were suspended in 70% ethanol, absorbed onto a 400 mesh formvar film-coated grid and then visualized by transmission electron microscopy (JEM-1200EX; JEOL Ltd., Japan) at an acceleration voltage of 80 kV. Digital images were taken with a CCD camera (VELETA, Olympus Soft Imaging Solutions GmbH).

Treatment Protocols and Tumor Cell Implantation: C57BL/6, TLR9 KO and Rag1 KO mice were obtained from the National Cancer Institute (Frederick, Md.) and studied at 5-6 wk of age. Lewis lung carcinoma (LLC1) cells were obtained from American Type Culture Collection (Manassas, Va.) and maintained in RPMI-1640 medium supplemented with 2% fetal bovine serum, penicillin (100 U/ml), streptomycin (0.1 mg/ml), 2 mM glutamate and 1% NEAA. On the day of inoculation, cultured cells were trypsinized, washed and suspended in 0.9% saline. Their viability exceeded 95%.

Tumor challenge studies were performed by instilling $10^6$ LLC1 cells in 50 µl of saline via orotracheal intubation to anesthetized mice as previously described (Savai et al., *Am J Pathol* 2005; 167:937-946, Savai et al., *Neoplasia* 2009; 11:48-56). One week later, free ODN or ODN-NP were administered either systemically (i.p.) or locally (i.t.). Instillation was achieved via orotracheal intubation using a 20 gauge 1" catheter (TERUMO, Somerset, N.J.) under anesthesia. Survival curves were generated from 4-6 mice per group and all results derived by combining data from 2-4 independent experiments. All animals were monitored 3×/wk and moribund mice euthanized as per Institutional Animal Care and Use Committee protocol.

Tissue Collection and Evaluation of Tumor Development: Bronchoalveolar lavage (BAL) fluid was obtained by tracheal cannulation of anesthetized mice. Cell differentials were performed on cytocentrifuged BAL preparations after fixation and staining with Diff-Quick (Dade Behring, Newark, Del.).

IL-12 levels in BAL and serum were determined by ELISA. Lungs were inflated and fixed by instilling 1 mL of 10% neutral-buffered formalin or periodate lysine paraformaldehyde (PLP) fixative (Wako Chemicals USA, Inc. Richmond, Va.) at 20 cm $H_2O$. Fixed tissue was embedded in paraffin, sectioned, and stained with hematoxylin and eosin for histopathological assessment. Tumor area was evaluated in mid-line sections and quantified using Image J software ver.1.48 (National Institute of Health, Bethesda, Md.).

In Vitro Cell Proliferation Assay: Single spleen cell suspensions were prepared. $5 \times 10^4$ cells/well were cultured in 96-well flat bottomed microtiter plates in complete RPMI 1640 medium supplemented with 10% fetal calf serum, 100 U/mL penicillin, 100 mg/mL streptomycin, 25 nmol/L HEPES, 1.0 mmol/L sodium pyruvate, NEAA, and 0.0035% 2-ME. The cells were stimulated free ODN, ODN-NP, or R837 (TLR7 agonist) for 72 hr. Cell proliferation was assessed using the CCK-8 assay as per manufacturer's recommendation (Dojindo molecular technologies, Inc. Rockville, Md.).

Immunohistochemistry and Immunofluorescent Analysis: Tissue sections were deparaffinized with xylene and rehydrated with graded ethanol. Endogenous peroxidase activity was blocked by incubation with 0.3% $H_2O_2$ in methanol for 30 min followed by Protein Block (Dako, Carpinteria, Calif.). They were then stained with the following primary antibodies: rat anti-Foxp3 (eBioscience, San Diego, Calif.; clone FKJ-16s, dilution 1:200), rat anti-F4/80 (AbD serotec, Raleigh, N.C.; clone Cl:A3-1, dilution 1:300), rabbit anti-CD3 (LSBio, Seattle, Wash.; clone EPR4517, dilution 1:100), hamster anti-CD11c (Abcam, Cambridge, Mass.; clone N418, dilution 1:100), rat anti-CD45R/B220 (BD Pharmingen, San Jose, Calif.; clone RA3-6B2, dilution 1:20), rabbit anti-CD205 (Abcam; clone EPR5233, dilution 1:500), rabbit anti-CD206 (Abcam; dilution 1:2000). Isotype matched negative controls were included to insure specificity.

For immunohistochemistry, stained sections were incubated with HRP-conjugated anti-rat or rabbit IgG (simple stain mouse Max Po; Nichirei, Tokyo, Japan) plus 3-amino-9-ethyl carbazole (AEC) substrate for color development (Nichirei). The sections were counterstained with Mayer's hematoxylin (Dako) and images were obtained using an IX50 inverted microscope equipped with digital imaging system (Olympus, Center Valley, Pa.). For immunofluorescent analysis, stained sections were incubated with secondary goat anti-rat Ab coupled to Texas Red (Vector Laboratories Inc., Burlingame, Calif.), rabbit anti-hamster coupled to DyLight 647 (Abcam), goat anti-rabbit coupled to DyLight 549 (Vector). Cell nuclei were visualized with DAPI (Vector). Slides were mounted with VECTASHIELD (Vector). Fluorescent images were acquired with a laser-scanning confocal microscope (LSM 510; Zeiss, Thronwood, N.Y.), equipped with a 63x/1.4NA oil objective.

Apoptosis Analysis: Formalin-fixed paraffin-embedded sections were deparaffinized and processed using the ApopTag Peroxidase In Situ Apoptosis Detection Kit (EMD Millipore Corporation, Billerica, Mass.). DNA fragments were labeled with digoxigenin-nucleotide followed by incubation with a peroxidase-conjugated anti-digoxigenin antibody. Positive signals were visualized by AEC (Nichirei).

ELISA: Cytokine levels in BAL, serum, and culture supernatants were measured by ELISA as previously described (Klinman et al., PNAS 1996; 93:2879-2883). Briefly, paired IL-6 and IL-12-specific mAbs were purchased from BD Pharmingen. Ninety-six-well Immulon H2B plates (Thermo LabSystems, Beverly, Mass.) were coated with capture cytokine-specific Abs and then blocked with PBS/1% BSA. Samples were added and bound cytokine detected by the addition of biotin-labeled secondary Ab, followed by phosphatase-conjugated avidin and a phosphatase-specific colorimetric substrate. Standard curves were generated using recombinant cytokines purchased from R&D Systems (Minneapolis, Minn.).

Statistical Analysis: Statistical analyses were performed using MedCalc, version 13.0 (MedCalc Software, Mariakerke, Belgium). Differences in survival were determined using the log rank test of Kaplan-Meier. Differences between groups were assessed using a one-way ANOVA followed by Student-Newman-Keuls post-hoc test. All tests were two-sided; probability values<0.05 were considered significant. All values are expressed as mean±SE.

Example 2

Effect of CpG ODN on the Growth of Pulmonary Tumors

Figure 9:
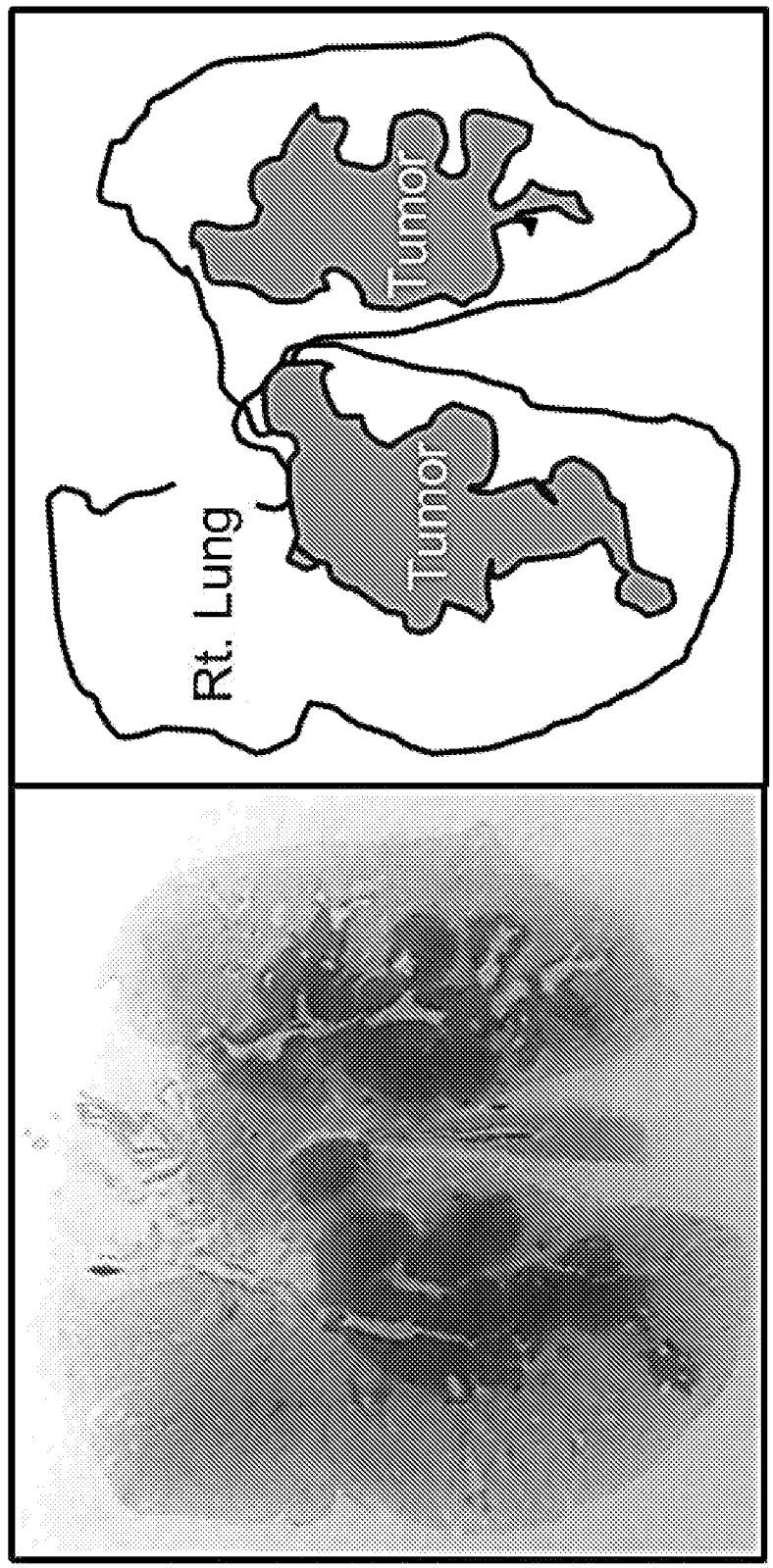
FIG. 9. Murine lung cancer model. LLC were implanted as described in FIG. 1. Representative histology showing the distribution of tumor nodules on Day 24.

A murine model of NSCLC was used to evaluate the anti-tumor activity of locally vs systemically administered CpG ODN. $10^6$ Lewis lung cancer (LLC) cells were instilled into the lungs of syngeneic C57BL/6 mice. As expected from previous studies, these cells proliferated and formed peri-bronchial tumors resembling those found in patients with primary lung cancer (FIG. 9).

Mice challenged with LLC had a median survival time of 22 days (FIG. 1). Systemic (i.p.) delivery of CpG ODN conferred a modest but statistically insignificant survival benefit (HR: 0.55; 95% CI, 0.24-1.26; p=0.11). In contrast, median survival time improved to 38 days (HR: 0.28; 95% CI, 0.13-0.59; p=0.01) when 50 µg of CpG ODN was delivered via the intra-tracheal (i.t.) route directly into the lungs (FIG. 1). This effect was sequence specific, as control ODN had no effect.

Figure 11B:
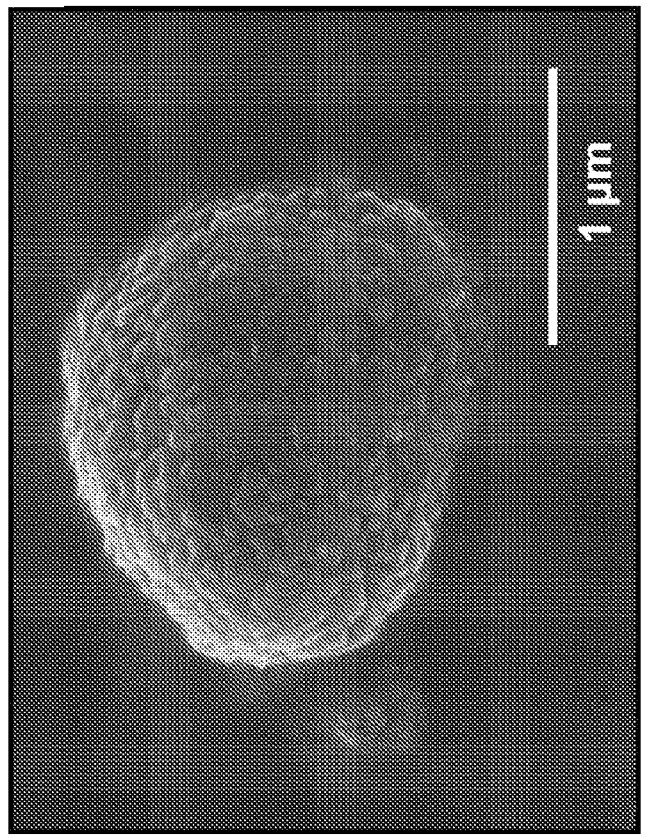
FIGS. 11A-11B. Microscopic characterization of CpG-NP. 11A) Transmission electron microscopy showing original nanoparticles after CpG ODN adsorption. CpG-NP were suspended in ethanol, absorbed onto formvar film and visualized by transmission electron microscopy. Bar=200 nm. 11B) Scanning electron photomicrograph showing a micropartcle assembled after freeze-drying. CpG-NP were suspended in saline just before scanning. Bar=1 um.
Figure 11A:
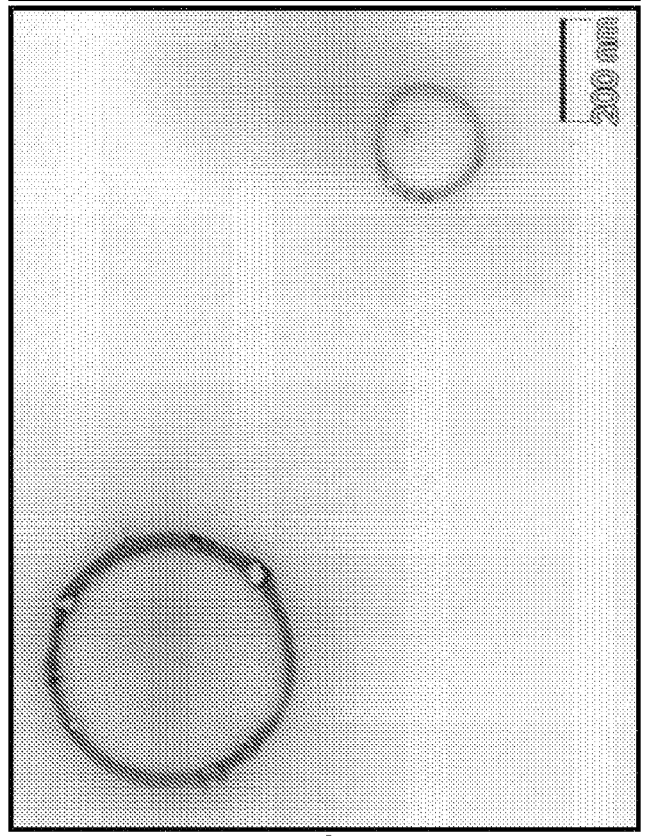

While local delivery of CpG ODN was superior to systemic administration, most mice in both treatment groups still succumbed to their tumors. As free CpG ODN rapidly diffuse from the lungs into the blood stream, it was postulated that their duration of action in the lungs might be prolonged if they were adsorbed onto polyketal nanoparticles (NP). Polyketal NP have an excellent in vivo safety profile and can form microparticles suitable for intratracheal delivery (Lee et al., *Bioconjugate Chem* 2007; 18:4-7, Fiore et al., *Biomaterials* 2010; 31:810-7). Preliminary studies showed that each mg of NP adsorbed 30 µg of ODN (CpG-NP) and that 80% of the ODN was released from the CpG-NP over 48 hr under physiologic conditions (FIG. 10). Those studies further showed that ODN-NP ranged in size from 200-400 nm when first synthesized but assembled into microparticles≈1-5 um in diameter after freeze drying (FIG. 11). This approximates the optimal size for particles designed to reach the distal bronchi via inhalation (Langer R. *Nature* 1998; 392(Suppl 6679): 5-10).

To determine whether CpG ODN retained the ability to stimulate cells after being adsorbed onto NP, the response of splenocytes from WT and TLR9 KO mice was compared. Both free and CpG-NP induced WT cells to secrete IL-6 and IL-12 over 24 hr of culture and to proliferate over 3 days (p<0.05, FIG. 2A). Free CpG was more effective at the earlier time point while CpG-NP was more effective after 3 days of culture, consistent with the release characteristics of ODN from NP. As seen in FIG. 10, less than half of the adsorbed ODN is available at the start of culture, with more being released over time. Cells from TLR9 KO mice failed to respond to free or NP-adsorbed CpG ODN, and control (non-CpG) ODN adsorbed to NP had no effect on cells from WT or TLR9 KO mice (FIG. 2).

The uptake and persistence of fluorescein-conjugated CpG ODN by the lungs was then evaluated. Six hr after intra-tracheal delivery, free ODN was detected throughout the mucosal surface of the bronchial tree (FIG. 3A). By 48 hr, little of this material remained in the bronchi or could be detected in the tumor (FIG. 3B). CpG-NP was distributed primarily in the bronchial and alveolar spaces at 6 hr (FIG. 3C). Of interest, this material persisted through 48 hr by which time it had accumulated in tumor nests (FIG. 3D). To identify the cells interacting with the CpG-NP, sections were counterstained with phenotype specific Abs. Results showed that fluorescein-labeled CpG-NP associated primarily with cells expressing F4/80 (macrophages) and CD205 (dendritic cells) within the tumors at 48 hr (FIG. 3 E/F).

Example 3

CpG-NP Activates Immune Cells In Vivo

CpG-NP was delivered into the lungs of normal mice via intra-tracheal catheter. BAL fluid was collected 2 days later. The BAL of mice treated with saline contained on average $4 \times 10^4$ cells/ml. In animals treated with free CpG ODN cellularity rose by$\approx$25% (p<0.05 vs saline, FIG. 4A). By comparison, the BAL of mice treated with CpG-NP contained$\approx 15 \times 10^4$ cells/ml (p<0.01, FIG. 4A). This increased cellular infiltrate consisted primarily of macrophages and lymphocytes. Consistent with previous studies, CpG ODN alone triggered a significant increase in pulmonary IL-12 levels, an effect magnified nearly 12-fold by CpG-NP (FIG. 4B). None of these changes was observed in mice treated with control ODN-NP.

Example 4

CpG-NP Improves the Survival of Mice with Lung Cancer

Figure 12:
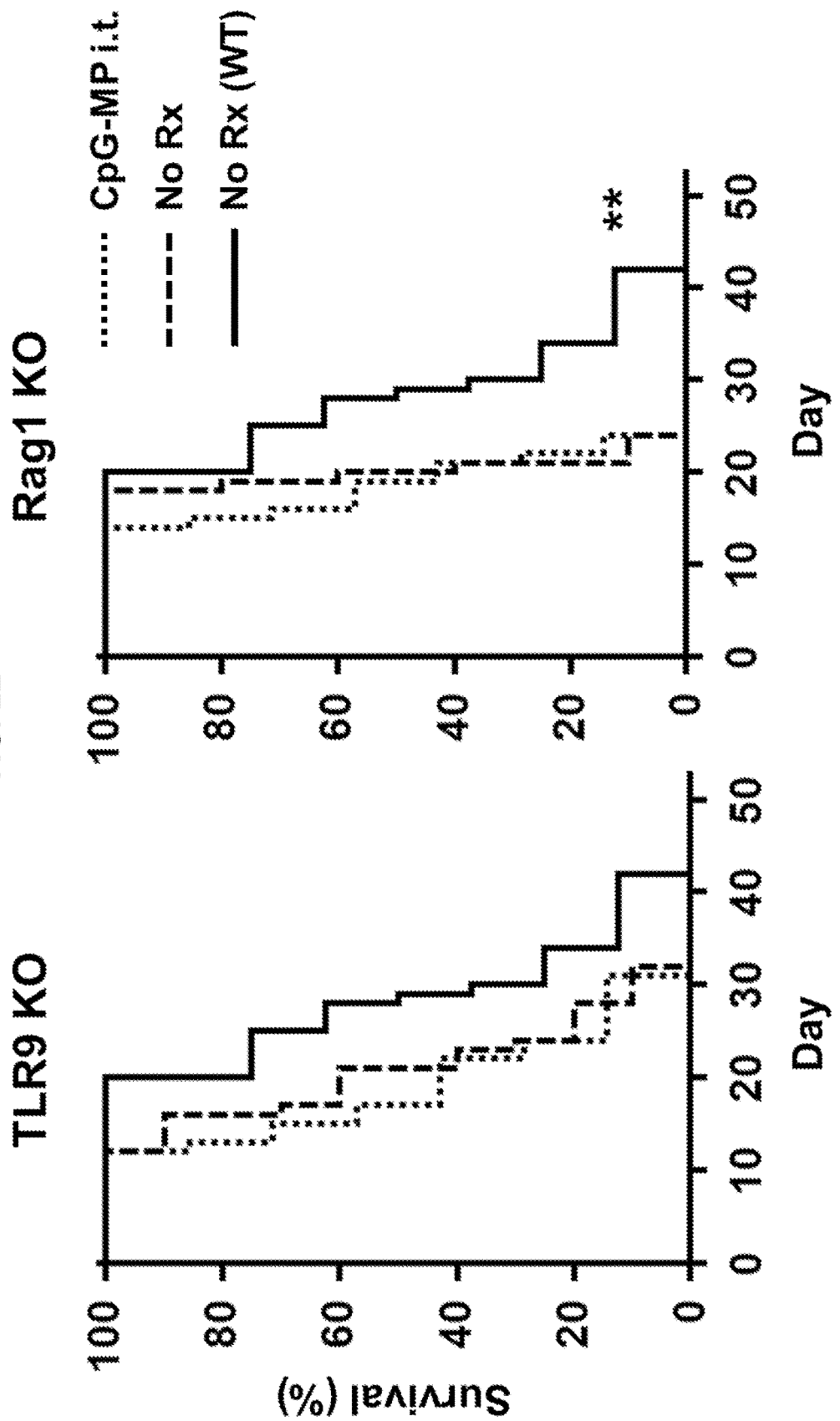
FIG. 12. Effect of CpG-NP on survival in LLC challenged mice. LLC were implanted and mice treated with CpG-NP as described in FIG. 1. Survival curves were generated for TLR9 KO and Rag1 KO mice and analyzed by Kaplan-Meier statistics using the log-rank test. Data from 2-3 independent experiments involving 7-10 mice/group were combined to generate each survival curve. **, p<0.01 vs No Rx (WT).

Mice were challenged with $10^6$ LLC i.t. as described above and then treated weekly for one month with CpG-NP starting on day 7. When delivered systemically (the route by which free CpG ODN was ineffective), CpG-NP prolonged median survival to 40 days (HR: 0.37; 95% CI, 0.14-0.95; p=0.007, FIG. 5). Even better results were achieved when the CpG-NP were instilled directly into the lungs, where 82% of mice survived indefinitely (some animals were followed for up to 1 year) (HR: 0.054; 95% CI, 0.024-0.12; p<0.0001 vs untreated controls). Control ODN adsorbed onto NP and delivered i.t. had no significant effect on survival (FIG. 5). The beneficial effect of CpG-NP was not observed in TLR9 KO or Rag1 KO mice challenged with LLC (FIG. 12), consistent with CpG-NP acting through host immune cells that express TLR9.

Example 5

Effect of CpG-NP on Tumor Immunity in the Lungs

The lungs of tumor bearing mice were analyzed histologically. As in humans with NSCLC, there were peribronchial tumor nodules present in mice (outlined in green, FIG. 6A) associated with tumor-induced bronchus-associated lymphoid tissue (referred to as Ti-BALT). In patients, the size, location, and type of cell present in Ti-BALT reflects the nature and magnitude of the host's anti-tumor response (Dieu-Nosjean M C, Cadranel J, J Clin Oncol 2008; 26:4410). Thus, a more detailed examination of Ti-BALT in mice with Lewis lung cancers was undertaken.

Figure 6A:
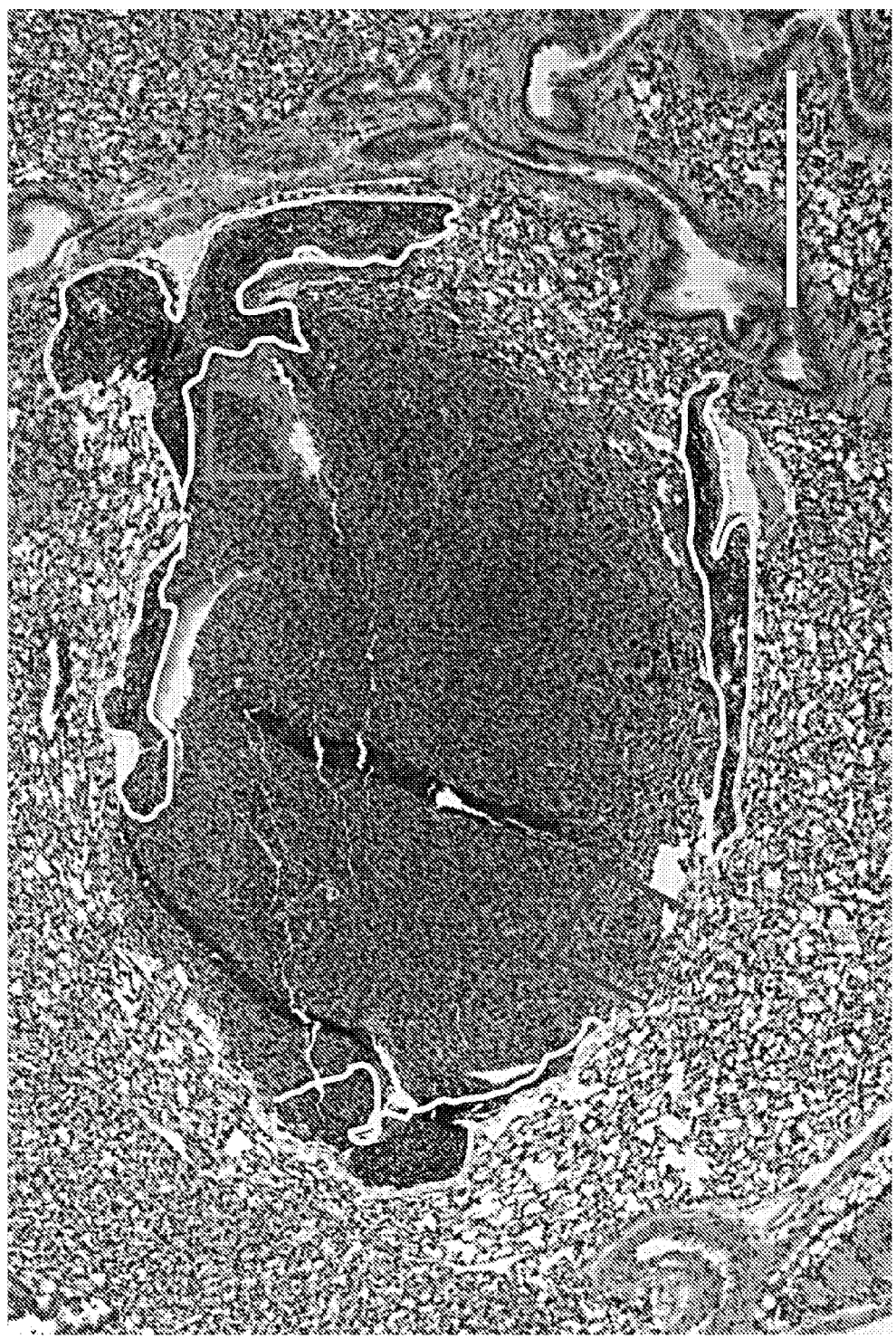
FIGS. 6A-6C. Histology of LLC tumors. LLC were implanted as described in FIG. 1 and lungs collected on day 20. 6A) Representative H&E stained photomicrograph showing a tumor nodule (outlined in green) plus Ti-BALT (yellow dotted area) (original magnification: ×40, Bar=500 um). 6B) Serial sections of tumor areas adjacent to Ti-BALT (red rectangles) or distant from Ti-BALT (blue rectangles) were stained with Foxp3 to identify $T_{reg}$ or were TdT-mediated dUTP nick end labeled (TUNEL) to identify apoptotic cells. 6C). The number of $T_{reg}$ and apoptotic cells per $mm^2$ was determined in 20 tumor nodules from 6 mice. **, p<0.01.
Figure 6C:
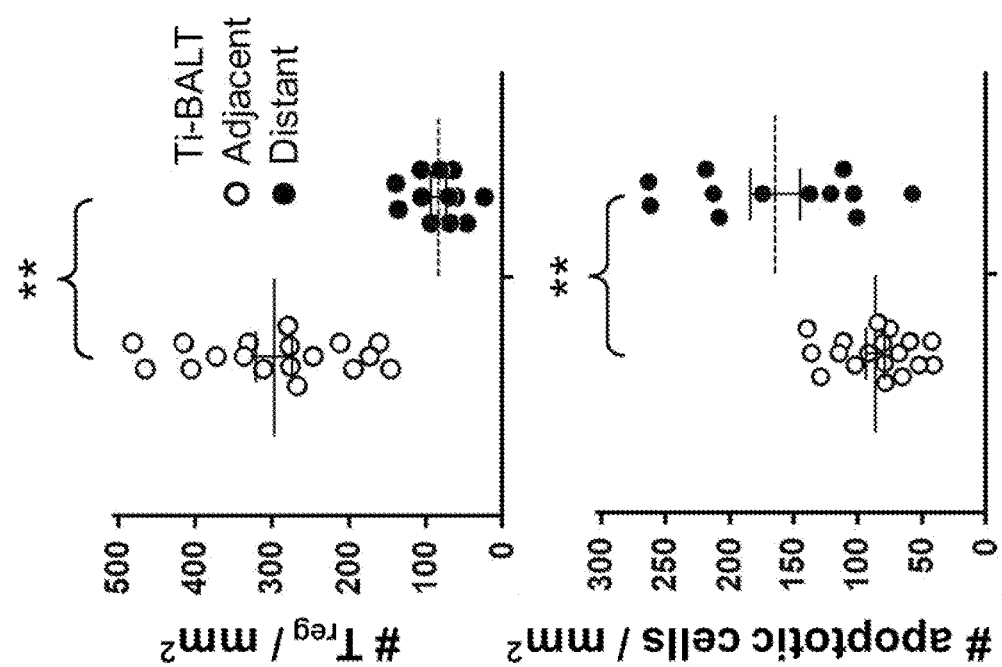
Figure 6B:
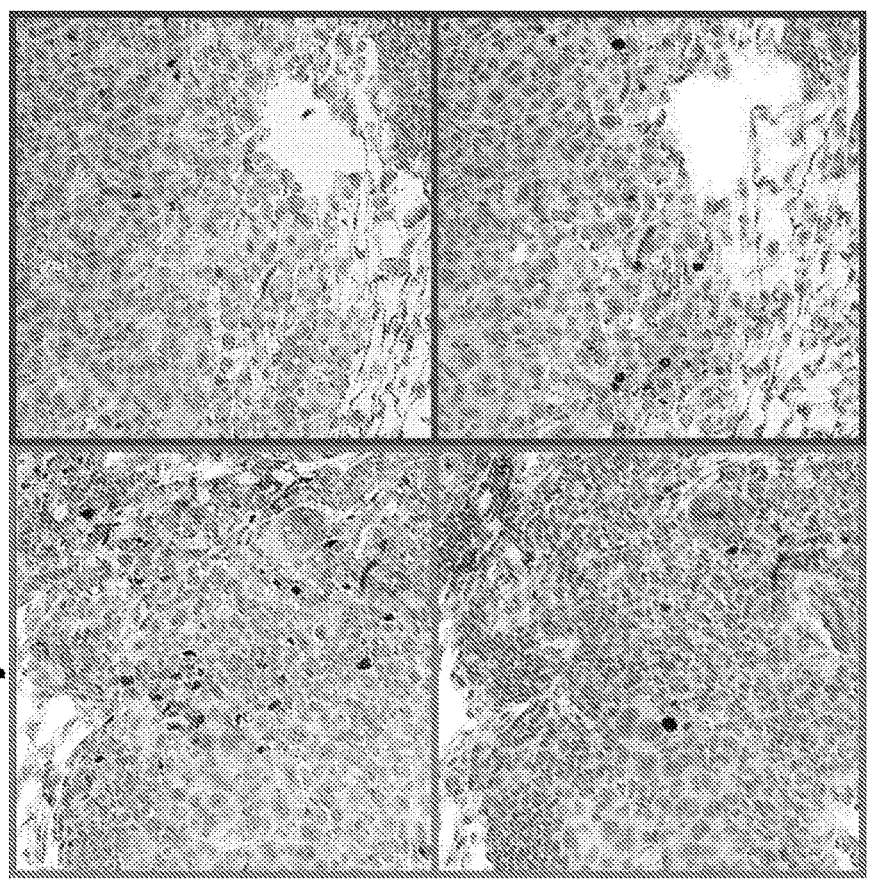

Ti-BALT surrounded $\approx$95% of the tumor nodules in untreated mice by day 20 (outlined in yellow, FIG. 6A). Areas of tumor that were adjacent to Ti-BALT (red rectangle) differed from tumor areas distant from Ti-BALT (blue rectangle) in containing more Foxp3$^+$ T$_{reg}$ and fewer apoptotic (TUNEL$^+$) cells (FIG. 6B). This effect was quantified by analyzing serial sections from 20 tumor nodules in 6 different mice (FIG. 6C). The frequency of T$_{reg}$ correlated inversely with the number of apoptotic cells in these sections (r=−0.47, p=0.008).

The effect of treating LLC mice with CpG-NP on the frequency of T$_{reg}$ and apoptotic cells was then assessed. CpG-NP was instilled into the lungs on days 7 and 14 and the lungs of recipient mice examined on day 20. Consistent with the survival data obtained in FIG. 5, mice treated with CpG-NP had significantly fewer tumor nodules and the nodules were significantly smaller than in control animals. Overall tumor burden was reduced by >90% (FIG. 7A/B). Ti-BALT could still be detected in CpG-NP treated animals as a rim surrounding $\approx$80% of the residual tumors. Of interest, the frequency of apoptotic cells was significantly higher whereas the frequency of Foxp3$^+$ T$_{reg}$ infiltrating these tumors was significantly lower than in control mice (p<0.01 for both parameters, FIG. 7C). Consequently, the ratio of apoptotic: T$_{reg}$ cells rose by 4-fold after CpG-NP treatment (FIG. 7D).

Figure 13A:
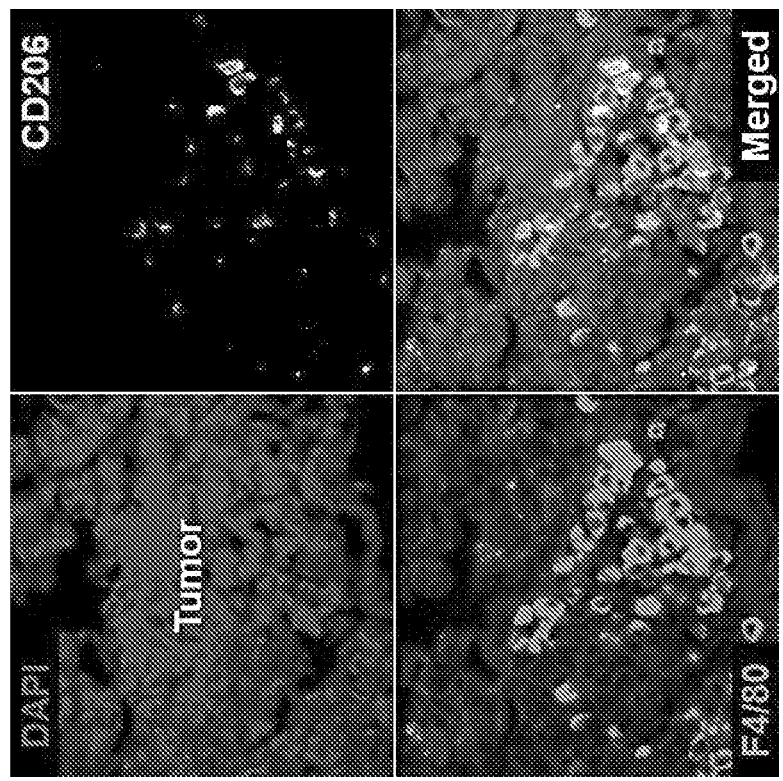
FIGS. 13A-13B. Macrophage phenotype in LLC tumor. LLC were implanted and mice treated with CpG-NP as described in FIG. 1. Lungs were collected on day 20. Representative photomicrograph of tumors from FIG. 13A) untreated and FIG. 13B) CpG-NP treated mice were stained with antibodies against F4/80 (red) and CD206 (green) analyzed by confocal microscopy.
Figure 13B:
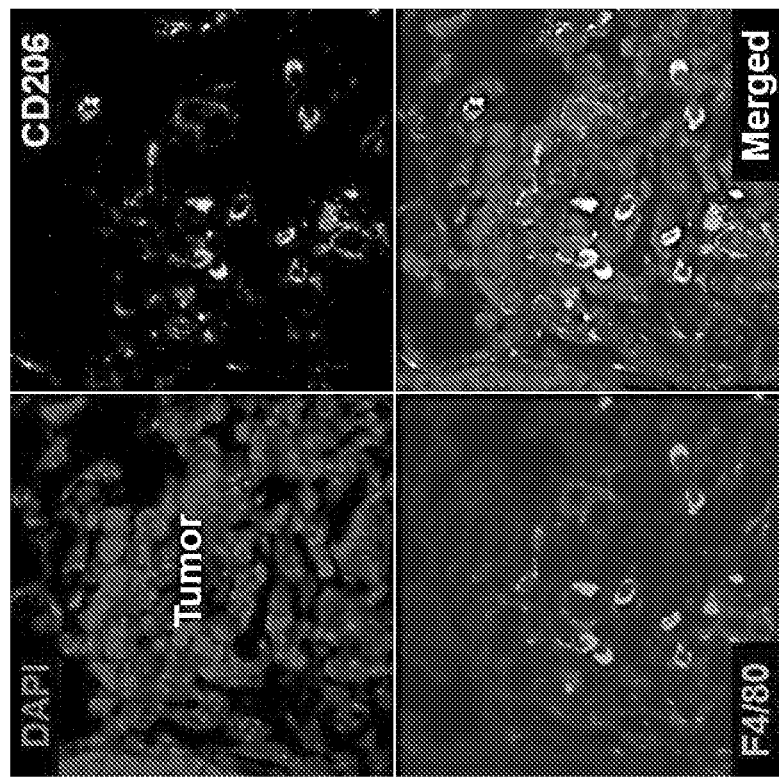
Figures 14A, 14B:
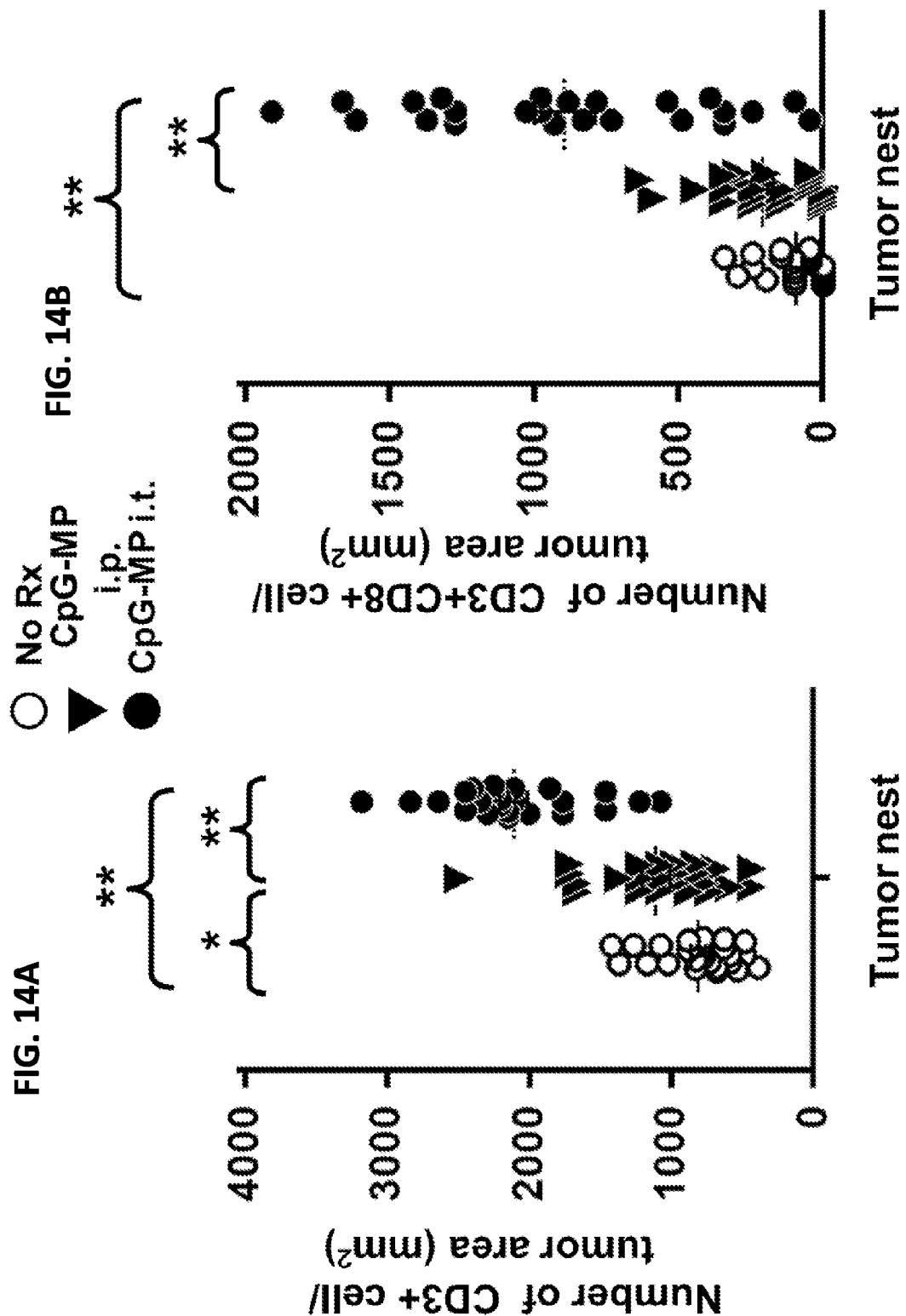
FIGS. 14A-14B. Effect of CpG-NP (aggregates provided microprticles "MP") on T cells accumulation in tumor nest. LLC were implanted and mice treated with CpG-NP as described in FIG. 1. Lungs were collected on day 20. The total number of T cells (CD3$^+$) and CD8$^+$ T cells (CD3$^+$ CD8$^+$) per $mm^2$ of tumor nest was quantified in 20 tumor nodules from each of 3 untreated (○), CpG-NP i.p. treated (▼), or CpG-NP i.t. treated (•) mice. *, p<0.05, **, p<0.01.

Based on histology showing that CpG-NP co-localized with tumor macrophages, the effect of CpG-NP treatment on that cell population was examined. CpG-NP treatment led to a modest increase in the number of macrophages per mm$^2$ of tumor ($\approx$40%, p<0.05, FIG. 8A). In untreated mice, the M1: M2 ratio of tumor infiltrating macrophages was approximately 1:1. That ratio shifted dramatically after CpG-NP treatment such that the relative frequency of M2 macrophages fell by $\approx$4-fold (FIG. 8B and FIG. 13).

Studies of patients and animals with lung cancer have demonstrated that systemic treatment with CpG ODN is of limited benefit (Sorrentino et al., J Immunol 2010; 185: 4641-4650, Sorrentino et al., Am J Respir Crit Care Med 2011; 183:1369-1379, Hirsh et al., J Clin Oncol 2011; 29:2667-2674, Manegold et al., Ann Oncol 2012; 23:72-77, Belani et al., Cancer Biol Ther 2013; 14:557-563). The study assessed whether instilling CpG ODN directly into the lungs of mice with LLC tumors would increase efficacy. The LLC model shares important features of primary human lung cancer including the peribronchial localization of tumors nodules and the presence of Ti-BALT (Dieu-Nosjean et al., J Clin Oncol 2008; 26:4410-4417, Wang et al., Ann Thorac Surg 1997; 64:216-219, Savai et al., Am J Pathol 2005; 167:937-946, Savai et al., Neoplasia 2009; 11:48-56).

Initial experiments examined the effect of delivering free ODN to mice with peribronchial tumors. Consistent with previous findings, systemic delivery had little effect on survival (Sorrentino et al., J Immunol 2010; 185:4641-4650). Outcomes improved when the ODN was delivered intratracheally, but the effect remained modest (FIG. 1). Biodistribution studies showed that free ODN i) localized to the mucosa and submucosal regions of the bronchus rather than reaching tumor-associated immune cells and ii) was rapidly cleared from the lungs (FIGS. 3C and 3D).

To improve the uptake and persistence of ODN in the tumor microenvironment, CpG were adsorbed onto biodegradable polyketal nanoparticles (FIG. 11). This strategy significantly differed from earlier efforts wherein ODN were mixed with 25-30 nm NP (Ballester et al., Vaccine 2011; 29:6959-6966, Nembrini et al., PNAS 2011; 108:E989-E997). The ODN was adsorbed onto NP and freeze dried to form aggregates of optimize size for delivery throughout the bronchial tree (Langer R. Nature 1998; 392(Suppl 6679): 5-10, Labiris et al. Br J Clin Pharmacol 2003; 56:588-99). CpG ODN adsorbed onto NP retained their sequence specific ability to activate TLR9-expressing cells and were well tolerated (FIG. 2 and data not shown). CpG-NP persisted for up to 6 days once instilled into the lungs where they accumulated in tumor-associated macrophage and DC (FIGS. 3A, 3B and 11). Systemic administration of CpG-NP was less effective, consistent with the finding that such particles are primarily trapped and removed from the circulation in the liver (Davis et al., *Nat Rev Drug Discov* 2008; 7:771-782).

Preliminary studies identified a dose of 50 μg of CpG ODN delivered weekly for one month as providing optimal protection in the LLC challenge model. Lowering the dose of ODN to 10 μg reduced long term survival from >80% to <40% (HR: 0.33; 95% CI, 0.11-1.03; p=0.05 vs No Rx) while increasing the dose to 100 μg was associated with evidence of toxicity (pulmonary inflammation and weight loss). The immunity induced by CpG ODN therapy was persistent, in that no tumors arose when survivors were re-challenged with LLC.

Figure 8:
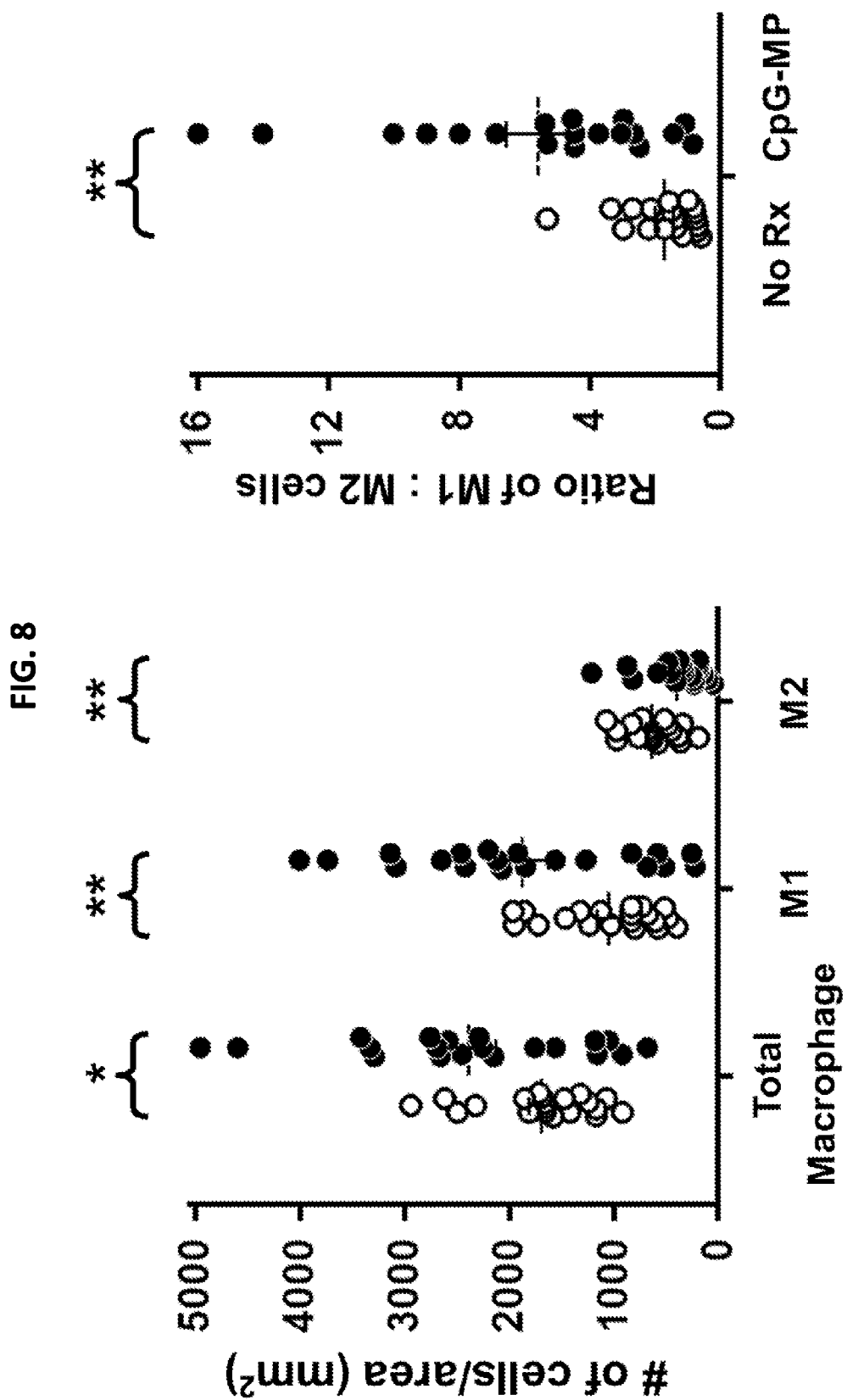
FIG. 8. Effect of CpG-NP (aggregates provided microprticles "MP") on tumor infiltrating macrophages. LLC were implanted and mice treated with CpG-NP as described in FIG. 1. Lungs were collected on day 20. The total number of macrophages (F4/80$^+$), M2 macrophages (F4/80$^+$, CD206$^+$) and M1 macrophages (F4/80+CD206$^-$) per $mm^2$ of tumor was quantified in 20 tumors from each of 3 untreated (○) or CpG-NP treated (●) mice. *, p<0.05, **, p<0.01 vs No Rx.

Recent reports found that increased numbers of Foxp3+ regulatory T cells were a negative prognostic indicator for lung cancer patients (Peterson et al., Cancer 2006; 107: 2866-2872, Shimizu et al., *J Thorac Oncol* 2010; 5:585-590, Suzuki et al., *J Clin Oncol* 2013; 31:490-498). Areas of a tumor adjacent to Ti-BALT were found to contain significantly more $T_{reg}$ and significantly fewer apoptotic cells than other areas (FIGS. 6B, 6C and 6D). There was a significant inverse relationship between Foxp3 and TUNEL+ cell frequency in serial sections (r=−0.47, p=0.008). Another translational study found that increased numbers of M-1 like macrophages correlated with prolonged survival in patients with NSCLC whereas shorter survival was observed when M-2 macrophages were dominant (Zeni et al., *Eur Respir J* 2007; 30:627-32, Ohri et al., *Eur Respir J* 2009; 33:118-26, Ohtaki et al., *J Thorac Oncol* 2010; 5:1507-15). M2 macrophages support tumor growth by suppressing the activity of tumoricidal CTL and NK cells while M1 macrophages support an inflammatory milieu that aids in tumor rejection (Sica et al., *Eur J Cancer* 2006; 42:717-27). The current findings show that local administration of CpG ODN shifted the tumor milieu in favor of M1 macrophages (FIG. 8).

CpG ODN delivered systemically or locally promote the development of tumoricidal T and NK cells (Baines et al. *Clin Cancer Res* 2003; 9:2693-2700, Heckelsmiller et al., *J Immunol* 2002; 169:3892-9, Nierkens et al., *PLoS One* 2009; 4:e8368). The present results suggest that local administration of CpG ODN using polyketal nanoparticles has additional benefits that include decreasing the number of immunosuppressive $T_{reg}$ while increasing the number of M1 macrophages in the tumor microenvironment. This combination of activities culminates in enhanced apoptosis of tumor cells. Of particular importance, local delivery of CpG-NP significantly improved the survival of mice bearing LLC tumors. 80% of these mice survived indefinitely (with some animals remaining under observation for >1 yr). These findings demonstrate that CpG-NP can be used to deliver immunostimulatory ODN directly to pulmonary tumors for treatment.

Example 6

Polyketal Particles Including a CpG ODN and an Imidazoquinoline Compound

The combination of a CpG plus a TRL 7/8 agonist is particularly effective in the treatment of lung cancer. For example, co-delivery of agonists targeting TLR7/8 (3M-052) and 9 (CpG ODN) into the tumor site eliminated the large established tumor (size over 500 mm(3)) (Zhao et al., *J Immunother Cancer* 2014; 2:12). Hence in some examples, the particles disclosed herein will be used for intratracheal delivery of particles incorporating TLR7/8 agonist (such as 3M-052) and CpG ODN to the lung cancer, to improve survival in subjects having lung cancer. The intratracheal administration achieves targeted delivery to the lung, for example to an alveolus or a terminal bronchus, that is believed to improve clinical response to treatment.

Example 7

Preparation of Nanoparticle Carrier

The polyketal particles are used as a carrier for the delivery of the active agents described herein, such as the CpG, imidazoquinoline, or both. The active agent can be loaded to the nanoparticle carrier, for example by adsorption to the surface of the nanoparticle or encapsulation within the nanoparticle. Methods for adsorption to the nanoparticle are disclosed in Example L The encapsulation of nucleic acids can be accomplished by the ion pairing technique. The hydrophobic ion pairing technique has been reported in the literature for the extraction of water soluble biotherapeutics (such as DNA and proteins). The basic procedure involves the pairing of a polar lipid or surfactant molecule with a (charged) DNA, RNA, or protein molecule, with an equimolar ratio of opposite charges. This pairing cancels the charges and produces a complex with a hydrophobic character. The resulting hydrophobic complex can be co-dissolved with the polyketal in an organic solvent, or a mixture of solvents, enabling particles to be fabricated by the oil-in-water single emulsion method.

For oligonucleotides, such as 20-base single-stranded (ss)DNA, a water-dichloromethane (DCM)-methanol procedure can be used with the surfactant 1,2-dioleoyl-3-trimethylammoniumpropane (DOTAP). The oligonucleotides are each ion paired with 1,2-dioleoyl-3-trimethylammoniumpropane (DOTAP). This method was adapted from a reported procedure for ion pairing plasmid DNA for encapsulation in microparticles (Patel et al., J. Pharm. Sci. 93:2573-2584, 2004). In a typical procedure, a solution of DNA or RNA (0.8 mg) in 1 mL TE buffer is combined with a solution of DOTAP (1.9 mg) in 1 mL dichloromethane (DCM) and 2.1 mL of methanol. This mixture creates a Bligh & Dyer monophase, which is allowed to stand for 5 minutes. Next, 1 mL DCM and 1 mL water is added to bring about phase separation, and the two-phase mixture is vortexed for 1 minute. The mixture is then centrifuged at 1200 g for 5 minutes at 20° C.

Example 8

Effect of CpG-NP on Tumor Infiltrating Immune Cells

The additional effects of the local administration of CpG ODN using polyketal nanoparticles on tumor infiltrating immune cells were investigated. Experiments were performed as disclosed in Example 1. Freeze drying produced microparticles of the nanoparticles.

Figure 15:
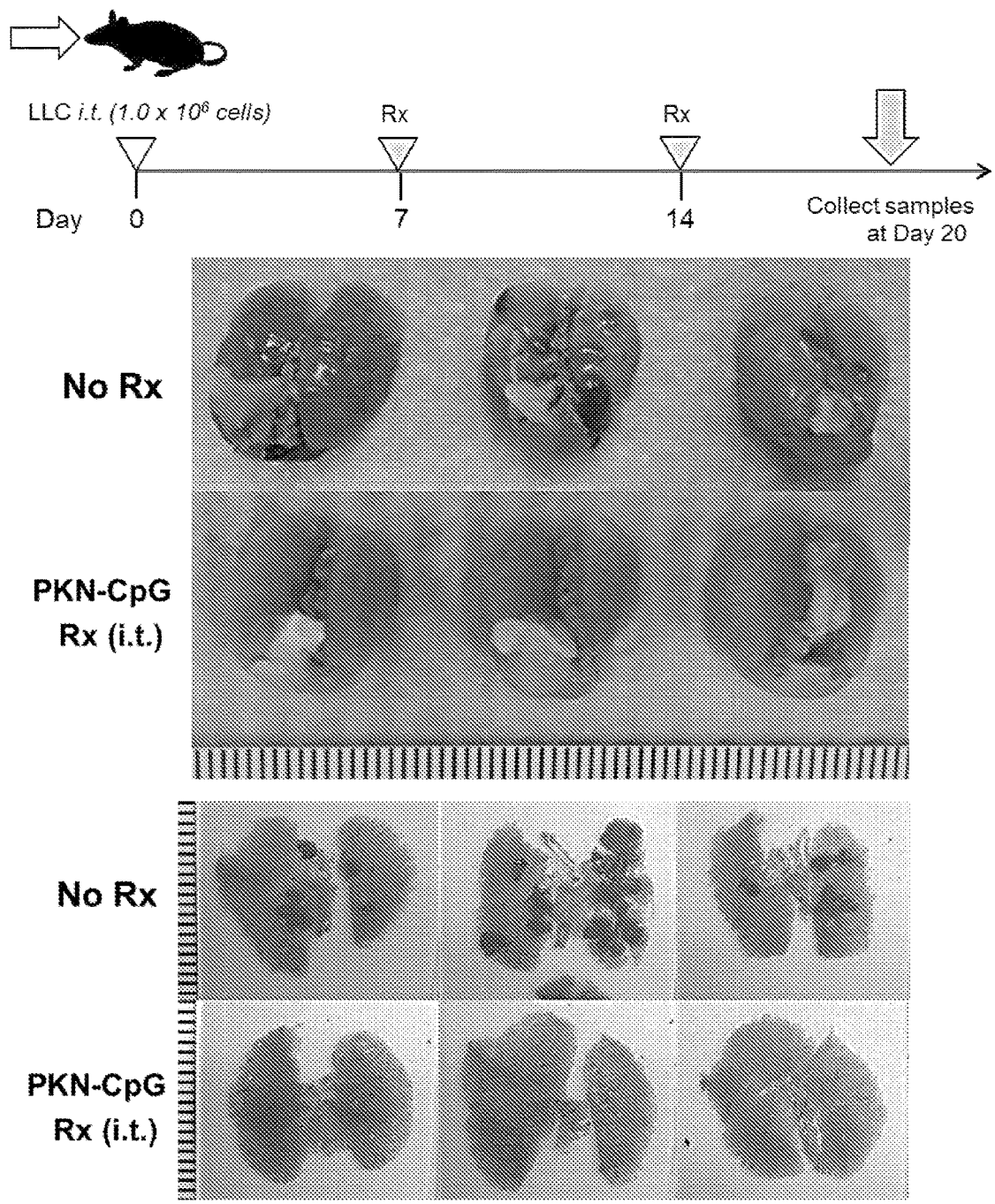
FIG. 15. Schematic diagram (top) showing the model system for primary lung cancer using intratracheal (i.t.) administration. CpG-NP were administered on days 7 and 14. Lungs were removed and processed for histological analysis. Exemplary images (bottom) of whole lungs and sections through those lungs showing the effect of treating tumor bearing mice with CpG microparticles.

Briefly, the tumor challenge studies were performed by instilling $10^6$ LLC1 cells in 50 ul of saline via orotracheal intubation to anesthetized C57BL/6 mice (5-6 weeks) as previously described (Savai R. *Am J Pathol* 2005; 167:937 and *Neoplasia* 2009; 11:48). One week later, intratracheal administration of ODN-NP was initiated and followed weekly basis. Instillation was achieved via orotracheal intubation using a 20 gauge 1" catheter (TERUMO, Somerset, N.J.) under anesthesia. At day 20, lung samples were collected, inflated, and fixed by instilling 1 mL of 10% neutral-buffered formalin or periodate lysine paraformaldehyde (PLP) fixative (Wako Chemicals USA, Inc. Richmond, Va.) at 20 cm $H_2O$. Tumor area was evaluated in mid-line sections (FIG. 15).

Figure 17B:
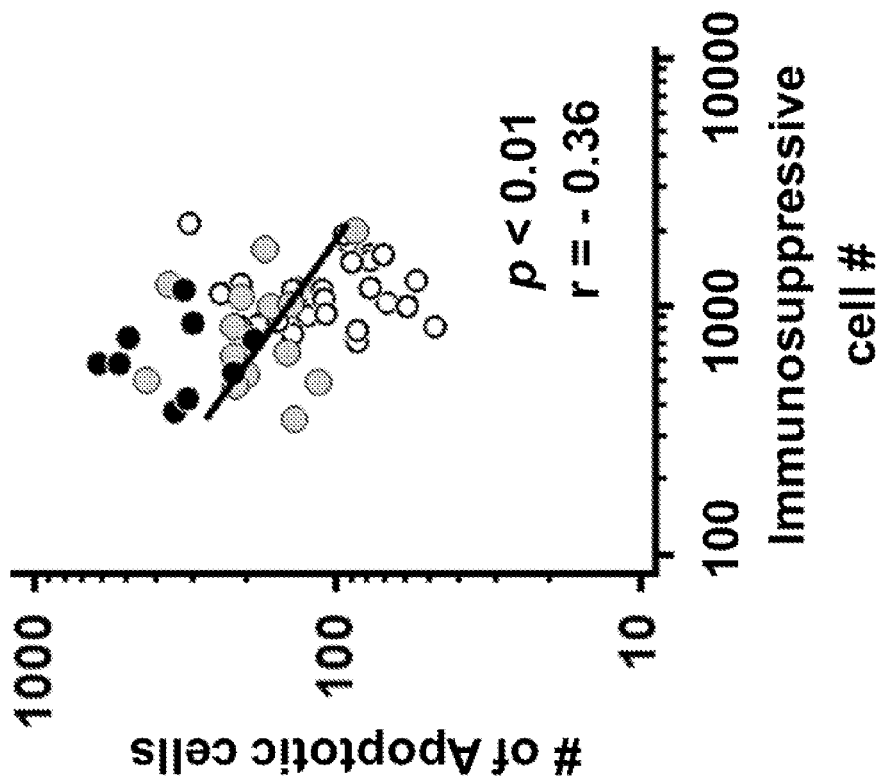
FIGS. 17A-17B. Correlation between cancer cell apoptosis and tumor infiltration by CTL vs immunosuppressive cells. LLC were implanted and mice treated as described in FIG. 6. Lungs were collected on day 20. The number of apoptotic (TUNEL$^+$) tumor cells is plotted against the number of CD3+ CD8+ CTL (FIG. 17A) and immunosuppressive cells (M2 macrophages plus Tregs) per $mm^2$ of tumor (FIG. 17B). Data were derived by analyzing serial sections from a total of 15-39 tumors in 3 mice per group (One way Anova).
Figure 17A:
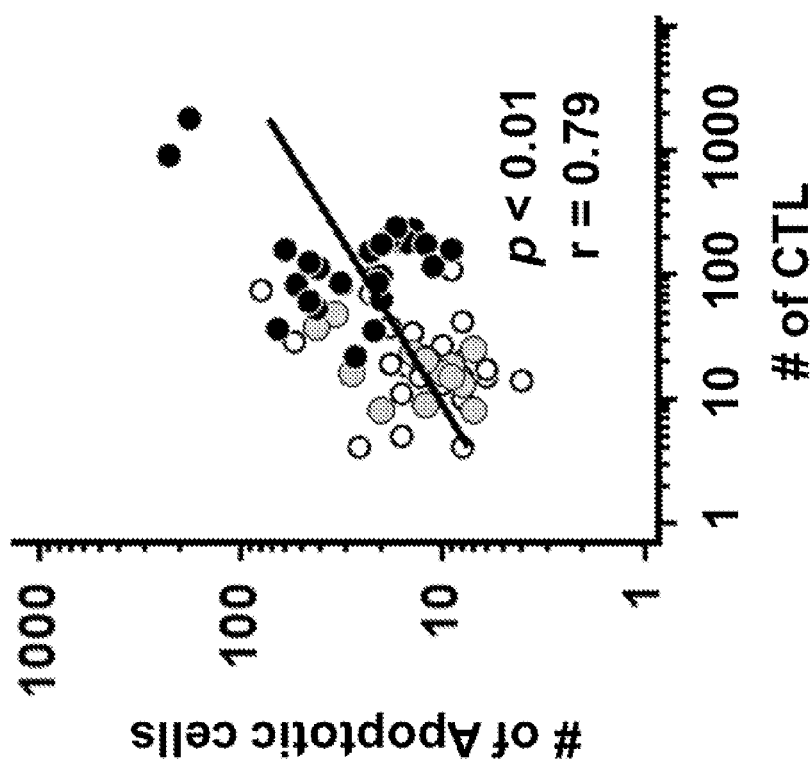

Treatment decreased tumor volume (FIGS. 16 and 17A) and increased the number of apoptotic cells (FIG. 17B). This treatment increased the number of CD8+ cells (FIG. 17C) and increased the number of immunosuppressive $T_{reg}$ (Foxp3$^+$) cells (FIG. 17D) plus M2 macrophages (F4/80$^+$, CD206$^+$) and altered the ratio of M1 (F4/80+CD206$^-$):M2 macrophages per mm$^2$ of tumor (FIG. 17E).

The correlation between cancer cell apoptosis and tumor infiltration by cytotoxic T lymphocytes (CTL) and immunosuppressive cells is shown in FIG. 17. There was a positive correlation between the number of apoptotic cells and the number of cytotoxic T lymphocytes. There was a negative correlation between the number of apoptotic cells and the number of immunosuppressive $T_{reg}$ (Foxp3$^+$) cells.

Example 9

Treatment of Tumors in the Periphery of the Lung

The intra-tracheal delivery route disclosed above generated peribronchial tumors that initially start growing from within the airway, similar to non-small cell primary lung cancer. An intravenous route of delivery generates tumors that develop primarily in the periphery of the lung without being associated with an airway, and thus mimics tumor metastasis.

Figure 18:
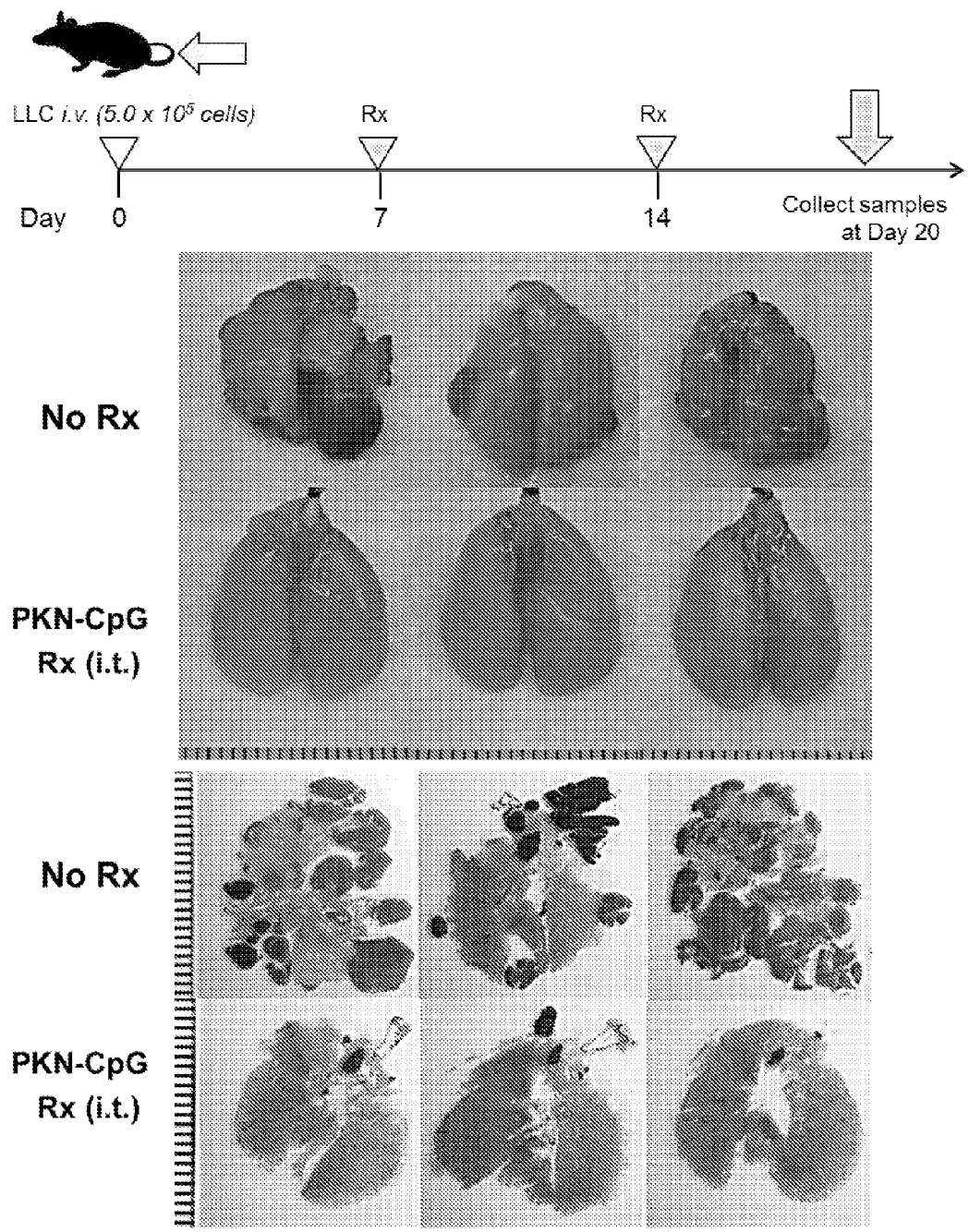
FIG. 18. Schematic diagram showing the model system for metastatic lung cancer using intravenous (i.v.) administration. CPG-NP were administered on days 7 and 14. Lungs were removed and processed for histological analysis. Exemplary images are shown.
Figure 19:
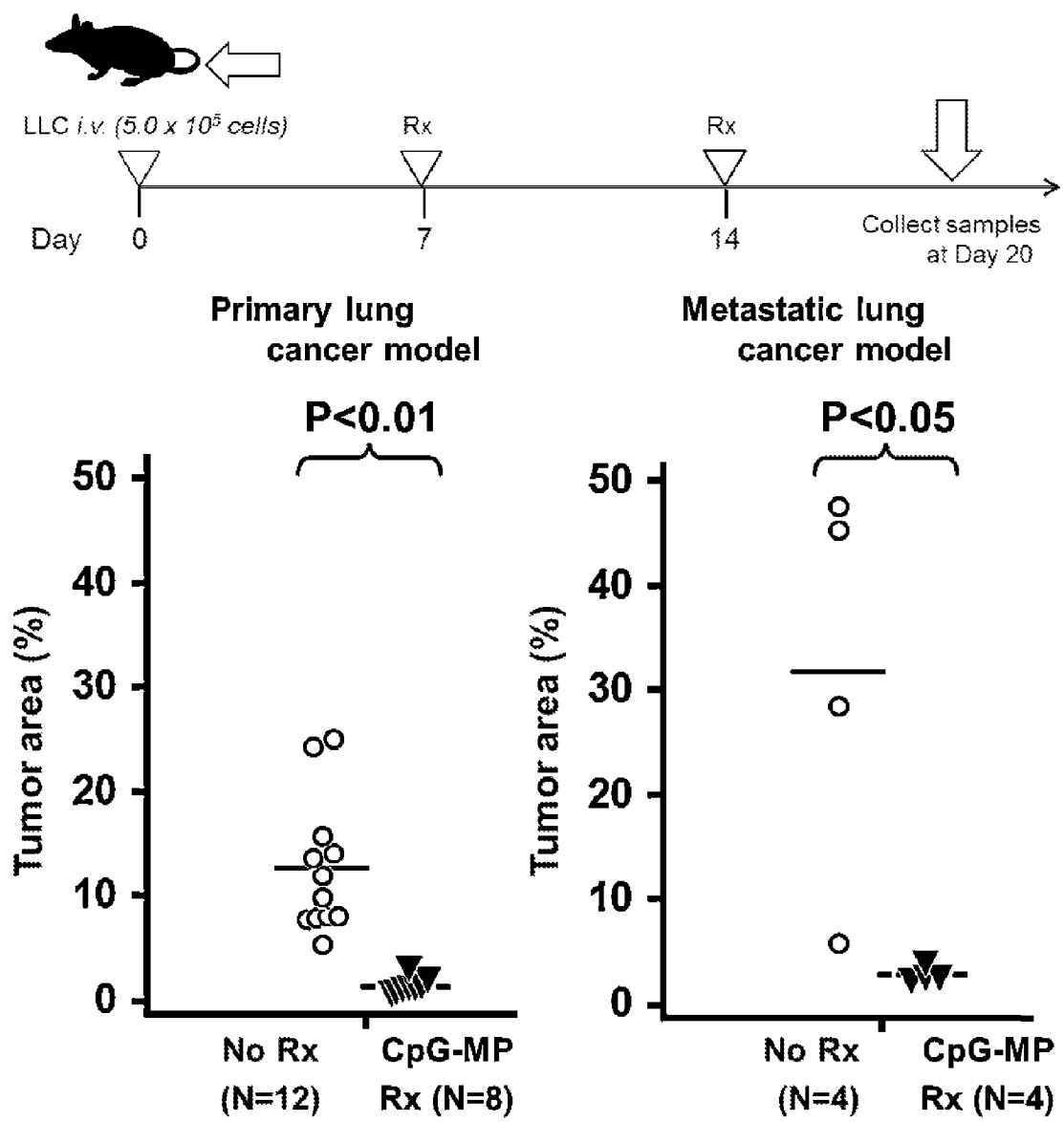
FIG. 19. Graphs showing the effect of CpG-NP on tumor area in the metastatic lung cancer model. Combined results from two experiments are shown. The CpG-NP aggregated during freeze-drying, and were provided in microprticles "MP."

Tumor challenge studies for metastatic lung cancer model were performed by injecting 5×10$^5$ LLC1 cells in 100 ul of saline via tail vein in C57BL/6 mice (6 weeks old) as previously described (Zhang Q. *J Biol Chem* 2006; 281: 18145 and Sorrentino R. *J Immunol* 2010; 185:4641), see FIG. 18. One week later, intratracheal administration of ODN-NP was initiated and followed weekly basis. Instillation was achieved via orotracheal intubation using a 20 gauge 1" catheter (TERUMO, Somerset, N.J.) under anesthesia. At day 20, lung samples were collected, inflated, and fixed by instilling 1 mL of 10% neutral-buffered formalin or periodate lysine paraformaldehyde (PLP) fixative (Wako Chemicals USA, Inc. Richmond, Va.) at 20 cm $H_2O$. Tumor area was evaluated in mid-line sections. The results are shown in FIG. 19. Treatment with ODN-NP significantly reduced tumor area.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of treating a subject with a lung cancer, comprising locally administering to the subject a therapeutically effective amount of a polyketal delivery particle comprising a CpG oligodeoxynucleotide, wherein the CpG oligodeoxynucleotide is a K-type CpG oligodeoxynucleotide or a D-type CpG oligodeoxynucleotide, and wherein the K-type CpG oligodeoxynucleotide has a nucleic acid sequence set forth as:

(SEQ ID NO: 2)
5' $N_1N_2N_3$D-CpG-W$N_4N_5N_6$ 3' wherein the central CpG motif is unmethylated, D is T, G or A, W is A or T, and $N_1$, $N_2$, $N_3$, $N_4$, $N_5$, and $N_6$ are any nucleotide, wherein the CpG oligodeoxynucleotide is 10 to 30 nucleotides in length; and wherein the D-type CpG oligodeoxynucleotide has a sequence (SEQ ID NO: 1)
5' $X_1X_2X_3$ Pu$_1$ Py$_2$ CpG Pu$_3$ Py$_4$ $X_4X_5X_6$(W)$_M$ (G)$_N$-3' wherein the central CpG motif is unmethylated, Pu is a purine nucleotide, Py is a pyrimidine nucleotide, X and W are any nucleotide, M is any integer from 0 to 10, and N is any integer from 4 to 10, and wherein the CpG oligodeoxynucleotide is 18 to 50 nucleotides in length, and the delivery particle is a nanoparticle or a microparticle, thereby treating the lung cancer in the subject.

2. The method of claim 1, wherein the CpG oligodeoxynucleotide is conjugated to the particle, or adsorbed on the surface of the particle.

3. The method of claim 1, wherein the CpG oligodeoxynucleotide is modified to prevent degradation.

4. The method of claim 3, wherein the CpG oligodeoxynucleotide comprises a phosphothioate bond.

5. The method of claim 1, wherein the CpG oligodeoxynucleotide is at most 30 nucleotides in length.

6. The method of claim 1, wherein the CpG oligodeoxynucleotide is the K-type CpG oligodeoxynucleotide.

7. The method of claim 6, wherein the K-type CpG oligodeoxynucleotide comprises the nucleic acid sequence of one of SEQ ID NOs: 3-34.

8. The method of claim 1, wherein the CpG oligodeoxynucleotide is the D-type CpG oligodeoxynucleotide.

9. The method of claim 8, wherein the D-type CpG oligodeoxynucleotide comprises the nucleic acid sequence of one of SEQ ID NOs: 37-63.

10. The method of claim 1, wherein the polyketal delivery particle further comprises an imidazoquinoline compound.

11. The method of claim 10, wherein the imidazoquinoline compound is a lipophilic imidazoquinoline compound.

12. The method of claim 11, wherein the lipophilic imidazoquinoline compound is 3M-052.

13. The method of claim 1, wherein the lung cancer is non-small cell lung cancer.

14. The method of claim 1, wherein the lung cancer is a small cell lung cancer.

15. The method of claim 1, wherein treating the lung cancer comprises reducing tumor volume and/or decreasing metastasis.

16. The method of claim 1, wherein the subject is a non-smoker.

17. The method of claim 1, wherein the polyketal particle is a nanoparticle about 200 nm to about 400 nm in diameter.

18. The method of claim 1, comprising administering to the subject a microparticle comprising the polyketal nanoparticle.

19. The method of claim 1, comprising administering to the subject a microparticle consisting of the polyketal nanoparticle.

20. The method of claim 18, wherein the microparticle is about 1 μm to about 5 μm in diameter.

21. The method of claim 18, wherein the polyketal nanoparticle comprises poly (1,4-phenylene-acetonedimethylene ketal) (PPADK), poly (cyclohexane-1,4-diyl acetone dimethylene ketal) (PCADK), PK1, PK2, PK3, PK4, PK5 or PK6.

22. The method of claim 1, wherein:
a) the subject is administered the K-type CpG oligodeoxynucleotide, and wherein the K-type CpG oligodexoynucleotide comprises the nucleic acid sequence of SEQ ID NO: 33,
b) the lung cancer is non-small cell lung cancer;
c) the polyketal nanoparticle comprises poly (1,4-phenylene-acetonedimethylene ketal) (PPADK); and
d) the method comprises administering to the subject a microparticle consisting of the polyketal nanoparticle, wherein the microparticle is about 1 μm to about 5 μm in diameter.

23. The method of claim 22, wherein the polyketal delivery particle is administered by pulmonary inhalation or intra-tracheal delivery.

* * * * *

SEQUENCE LISTING

```
<160> NUMBER OF SEQ ID NOS: 63

<210> SEQ ID NO 1
<211> LENGTH: 32
<212> TYPE: DNA
<213> ORGANISM: Artificial Sequence
<220> FEATURE:
<223> OTHER INFORMATION: Consensus oligodeoxynucleotide
<220> FEATURE:
<221> NAME/KEY: misc_feature
<222> LOCATION: (1)..(3)
<223> OTHER INFORMATION: n is any nucleotide
<220> FEATURE:
<221> NAME/KEY: misc_feature
<222> LOCATION: (4)..(4)
<223> OTHER INFORMATION: n is A or G
<220> FEATURE:
<221> NAME/KEY: misc_feature
<222> LOCATION: (5)..(5)
<223> OTHER INFORMATION: n is C or T
<220> FEATURE:
<221> NAME/KEY: misc_feature
<222> LOCATION: (8)..(8)
<223> OTHER INFORMATION: n is A or G
<220> FEATURE:
<221> NAME/KEY: misc_feature
<222> LOCATION: (9)..(9)
<223> OTHER INFORMATION: n is C or T
<220> FEATURE:
<221> NAME/KEY: misc_feature
<222> LOCATION: (10)..(12)
<223> OTHER INFORMATION: n is any nucleotide
<220> FEATURE:
<221> NAME/KEY: misc_feature
<222> LOCATION: (13)..(22)
<223> OTHER INFORMATION: n is any nucleotide or no nucleotide
<220> FEATURE:
<221> NAME/KEY: misc_feature
<222> LOCATION: (27)..(32)
<223> OTHER INFORMATION: n is G or no nucleotide

<400> SEQUENCE: 1
```

-continued nnnnncgnnn nnnnnnnnnn nngggnnnnn nn                              32

<210> SEQ ID NO 2
<211> LENGTH: 10
<212> TYPE: DNA
<213> ORGANISM: Artificial Sequence
<220> FEATURE:
<223> OTHER INFORMATION: consensus oligodeoxynucleotide
<220> FEATURE:
<221> NAME/KEY: misc_feature
<222> LOCATION: (1)..(3)
<223> OTHER INFORMATION: N is any nucleotide
<220> FEATURE:
<221> NAME/KEY: misc_feature
<222> LOCATION: (4)..(4)
<223> OTHER INFORMATION: N is T, G or A
<220> FEATURE:
<221> NAME/KEY: misc_feature
<222> LOCATION: (7)..(7)
<223> OTHER INFORMATION: N is A or T
<220> FEATURE:
<221> NAME/KEY: misc_feature
<222> LOCATION: (8)..(10)
<223> OTHER INFORMATION: N is any nucleotide

<400> SEQUENCE: 2 nnnncgnnnn                                                       10

<210> SEQ ID NO 3
<211> LENGTH: 20
<212> TYPE: DNA
<213> ORGANISM: Artificial Sequence
<220> FEATURE:
<223> OTHER INFORMATION: immunostimulatory oligodeoxynucleotide

<400> SEQUENCE: 3
ataatcgacg ttcaagcaag                                            20

<210> SEQ ID NO 4
<211> LENGTH: 13
<212> TYPE: DNA
<213> ORGANISM: Artificial Sequence
<220> FEATURE:
<223> OTHER INFORMATION: immunostimulatory oligodeoxynucleotide

<400> SEQUENCE: 4
ctcgagcgtt ctc                                                   13

<210> SEQ ID NO 5
<211> LENGTH: 14
<212> TYPE: DNA
<213> ORGANISM: Artificial Sequence
<220> FEATURE:
<223> OTHER INFORMATION: Immunostimulatory oligodeoxynucleotide

<400> SEQUENCE: 5
tctcgagcgt tctc                                                  14

<210> SEQ ID NO 6
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 6
actctggagc gttctc                                                16

```
<210> SEQ ID NO 7
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 7
tgcagcgttc tc                                                              12

<210> SEQ ID NO 8
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 8
tcgaggcttc tc                                                              12

<210> SEQ ID NO 9
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 9
gtcggcgttg ac                                                              12

<210> SEQ ID NO 10
<211> LENGTH: 19
<212> TYPE: DNA
<213> ORGANISM: Artificial Sequence
<220> FEATURE:
<223> OTHER INFORMATION: immunostimulatory oligodeoxynucleotide

<400> SEQUENCE: 10
tcgactctcg agcgttctc                                                       19

<210> SEQ ID NO 11
<211> LENGTH: 20
<212> TYPE: DNA
<213> ORGANISM: Artificial Sequence
<220> FEATURE:
<223> OTHER INFORMATION: immunostimulatory oligodeoxynucleotide

<400> SEQUENCE: 11
atcgactctc gagcgttctc                                                      20

<210> SEQ ID NO 12
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 12
tcgagcgttc tc                                                              12

<210> SEQ ID NO 13
<211> LENGTH: 12
<212> TYPE: DNA
<213> ORGANISM: Artificial Sequence
<220> FEATURE:
<223> OTHER INFORMATION: immunostimulatory oligodeoxynucleotide
```

```
<400> SEQUENCE: 13
gtcggcgtcg ac                                                    12

<210> SEQ ID NO 14
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 14
gtcgacgttg ac                                                    12

<210> SEQ ID NO 15
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 15
actctcgagg gttctc                                                16

<210> SEQ ID NO 16
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 16
actctcgagc gttctc                                                16

<210> SEQ ID NO 17
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 17
gtcgtcgatg ac                                                    12

<210> SEQ ID NO 18
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 18
gtcgacgctg ac                                                    12

<210> SEQ ID NO 19
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 19
gtcgacgtcg ac                                                    12

<210> SEQ ID NO 20
```

```
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 20
gtcatcgatg ca                                                         12

<210> SEQ ID NO 21
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 21
gtcagcgtcg ac                                                         12

<210> SEQ ID NO 22
<211> LENGTH: 11
<212> TYPE: DNA
<213> ORGANISM: Artificial Sequence
<220> FEATURE:
<223> OTHER INFORMATION: immunostimulatory oligodeoxynucleotide

<400> SEQUENCE: 22
tcgagcgttc t                                                          11

<210> SEQ ID NO 23
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 23
actctggagc gttctc                                                     16

<210> SEQ ID NO 24
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 24
actctcgagg gttctc                                                     16

<210> SEQ ID NO 25
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 25
actctcgagc gttcta                                                     16

<210> SEQ ID NO 26
<211> LENGTH: 16
<212> TYPE: DNA
<213> ORGANISM: Artificial Sequence
<220> FEATURE:
<223> OTHER INFORMATION: immunostimulatory oligodeoxynucleotide

<400> SEQUENCE: 26
```

```
catctcgagc gttctc                                                    16
```

<210> SEQ ID NO 27
<211> LENGTH: 14
<212> TYPE: DNA
<213> ORGANISM: Artificial Sequence
<220> FEATURE:
<223> OTHER INFORMATION: immunostimulatory oligodeoxynucleotide

<400> SEQUENCE: 27

```
actctttcgt tctc                                                      14
```

<210> SEQ ID NO 28
<211> LENGTH: 11
<212> TYPE: DNA
<213> ORGANISM: Artificial Sequence
<220> FEATURE:
<223> OTHER INFORMATION: immunostimulatory oligodeoxynucleotide

<400> SEQUENCE: 28

```
tcgagcgttc t                                                         11
```

<210> SEQ ID NO 29
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 29

```
tcgttcgttc tc                                                        12
```

<210> SEQ ID NO 30
<211> LENGTH: 15
<212> TYPE: DNA
<213> ORGANISM: Artificial Sequence
<220> FEATURE:
<223> OTHER INFORMATION: immunostimulatory oligodeoxynucleotide

<400> SEQUENCE: 30

```
gctagacgtt agcgt                                                     15
```

<210> SEQ ID NO 31
<211> LENGTH: 12
<212> TYPE: DNA
<213> ORGANISM: Artificial Sequence
<220> FEATURE:
<223> OTHER INFORMATION: immunostimulatory oligodeoxynucleotide

<400> SEQUENCE: 31

```
tcgaggcttc tc                                                        12
```

<210> SEQ ID NO 32
<211> LENGTH: 21
<212> TYPE: DNA
<213> ORGANISM: Artificial Sequence
<220> FEATURE:
<223> OTHER INFORMATION: immunostimulatory oligodeoxynucletodie

<400> SEQUENCE: 32

```
tcgtcgtttt tcggtcgttt t                                              21
```

<210> SEQ ID NO 33
<211> LENGTH: 24
<212> TYPE: DNA

<213> ORGANISM: Artificial Sequence
<220> FEATURE:
<223> OTHER INFORMATION: immunostimulatory oligodeoxynucleotide

<400> SEQUENCE: 33
tcgtcgtttt gtcgttttgt cgtt                                          24

<210> SEQ ID NO 34
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 34
tccatgacgt tcctgacgtt                                               20

<210> SEQ ID NO 35
<211> LENGTH: 15
<212> TYPE: DNA
<213> ORGANISM: Artificial Sequence
<220> FEATURE:
<223> OTHER INFORMATION: Control oligodeoxynucleotide

<400> SEQUENCE: 35
tagagcttag cttgc                                                    15

<210> SEQ ID NO 36
<211> LENGTH: 20
<212> TYPE: DNA
<213> ORGANISM: Artificial Sequence
<220> FEATURE:
<223> OTHER INFORMATION: Control oligodeoxynucleotide

<400> SEQUENCE: 36
tccatgagct tcctgagtct                                               20

<210> SEQ ID NO 37
<211> LENGTH: 12
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(3)
<223> OTHER INFORMATION: n is any nucleotide
<220> FEATURE:
<221> NAME/KEY: misc_feature
<222> LOCATION: (10)..(12)
<223> OTHER INFORMATION: n is any nucleotide

<400> SEQUENCE: 37
nnnaccggtn nn                                                       12

<210> SEQ ID NO 38
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(3)
<223> OTHER INFORMATION: n is any nucleotide
<220> FEATURE:
<221> NAME/KEY: misc_feature
<222> LOCATION: (10)..(12)
<223> OTHER INFORMATION: n is any nucleotide

<400> SEQUENCE: 38
nntgcatcga tgcagggggg                                              20

<210> SEQ ID NO 39
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 39
ggtgcatcga tacagggggg                                              20

<210> SEQ ID NO 40
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 40
ggtgcgtcga tgcagggggg                                              20

<210> SEQ ID NO 41
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 41
ggtgcatcga tgcagggggg                                              20

<210> SEQ ID NO 42
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 42
ggtgcaccgg tgcagggggg                                              20

<210> SEQ ID NO 43
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 43
ggtgtgtcga tgcagggggg                                              20

<210> SEQ ID NO 44
<211> LENGTH: 18
<212> TYPE: DNA
<213> ORGANISM: Artificial Sequence
<220> FEATURE:
<223> OTHER INFORMATION: Immunostimultory Oligodeoxynucleotide

<400> SEQUENCE: 44
tgcatcgatg cagggggg                                                18

<210> SEQ ID NO 45

```
<211> LENGTH: 34
<212> TYPE: DNA
<213> ORGANISM: Artificial Sequence
<220> FEATURE:
<223> OTHER INFORMATION: Immunostimultory Oligodeoxynucleotide
<220> FEATURE:
<221> NAME/KEY: misc_feature
<222> LOCATION: (3)..(5)
<223> OTHER INFORMATION: N is any nucleotide
<220> FEATURE:
<221> NAME/KEY: misc_feature
<222> LOCATION: (6)..(6)
<223> OTHER INFORMATION: N is A or G
<220> FEATURE:
<221> NAME/KEY: misc_feature
<222> LOCATION: (7)..(7)
<223> OTHER INFORMATION: N is C or T
<220> FEATURE:
<221> NAME/KEY: misc_feature
<222> LOCATION: (10)..(10)
<223> OTHER INFORMATION: N is A or G
<220> FEATURE:
<221> NAME/KEY: misc_feature
<222> LOCATION: (11)..(11)
<223> OTHER INFORMATION: N is C or T
<220> FEATURE:
<221> NAME/KEY: misc_feature
<222> LOCATION: (12)..(14)
<223> OTHER INFORMATION: N is any nucleotide
<220> FEATURE:
<221> NAME/KEY: misc_feature
<222> LOCATION: (15)..(24)
<223> OTHER INFORMATION: N is any nucleotide or not present
<220> FEATURE:
<221> NAME/KEY: misc_feature
<222> LOCATION: (29)..(34)
<223> OTHER INFORMATION: N is G or not present

<400> SEQUENCE: 45
ggnnnnncgn nnnnnnnnnn nnnnggggnn nnnn                                 34

<210> SEQ ID NO 46
<211> LENGTH: 20
<212> TYPE: DNA
<213> ORGANISM: Artificial Sequence
<220> FEATURE:
<223> OTHER INFORMATION: Immunostimulatory Oligodeoxynucleotide

<400> SEQUENCE: 46
ggtgcatcgt tgcaggggggg                                                20

<210> SEQ ID NO 47
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 47
ggtgcgtcga cgcaggggggg                                                20

<210> SEQ ID NO 48
<211> LENGTH: 20
<212> TYPE: DNA
<213> ORGANISM: Artificial Sequence
<220> FEATURE:
<223> OTHER INFORMATION: Immunostimultory oligodeoxynucleotide

<400> SEQUENCE: 48
ggtcgatcga tgcacggggg                                                 20
```

```
<210> SEQ ID NO 49
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 49
ggtgcatcga tgcagggggg                                          20

<210> SEQ ID NO 50
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 50
ggtgcatcga cgcagggggg                                          20

<210> SEQ ID NO 51
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 51
ggtgcatcga taggcggggg                                          20

<210> SEQ ID NO 52
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 52
ggtgcaccga tgcagggggg                                          20

<210> SEQ ID NO 53
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 53
cctgcatcga tgcagggggg                                          20

<210> SEQ ID NO 54
<211> LENGTH: 20
<212> TYPE: DNA
<213> ORGANISM: Artificial Sequence
<220> FEATURE:
<223> OTHER INFORMATION: Immunostimulatory oligodeoxynucleotide

<400> SEQUENCE: 54
ggtatatcga tataggggggg                                         20

<210> SEQ ID NO 55
<211> LENGTH: 20
<212> TYPE: DNA
<213> ORGANISM: Artificial Sequence
<220> FEATURE:
<223> OTHER INFORMATION: Immunostimulatory oligodeoxynucleotide
```

-continued

```
<400> SEQUENCE: 55
ggtggatcga tccaggggg                                          20

<210> SEQ ID NO 56
<211> LENGTH: 20
<212> TYPE: DNA
<213> ORGANISM: Artificial Sequence
<220> FEATURE:
<223> OTHER INFORMATION: immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 56
nntgcatcga tgcaggggg                                          20

<210> SEQ ID NO 57
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 57
nntgcaccgg tgcaggggg                                          20

<210> SEQ ID NO 58
<211> LENGTH: 20
<212> TYPE: DNA
<213> ORGANISM: Artificial Sequence
<220> FEATURE:
<223> OTHER INFORMATION: Immunostimulatory oligdeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 58
nntgcgtcga cgcaggggg                                          20

<210> SEQ ID NO 59
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 59
nntgcgtcga tgcaggggg                                          20

<210> SEQ ID NO 60
<211> LENGTH: 20
<212> TYPE: DNA
<213> ORGANISM: Artificial Sequence
<220> FEATURE:
<223> OTHER INFORMATION: Immunostimultory oligodeoxynucleotide
<220> FEATURE:
<221> NAME/KEY: misc_feature
<222> LOCATION: (1)..(2)
<223> OTHER INFORMATION: N is any nucleotide or no nucleotide
```

```
<400> SEQUENCE: 60
nntgcgccgg cgcagggggg                                               20

<210> SEQ ID NO 61
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 61
nntgcgccga tgcagggggg                                               20

<210> SEQ ID NO 62
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 62
nntgcatcga cgcagggggg                                               20

<210> SEQ ID NO 63
<211> LENGTH: 20
<212> TYPE: DNA
<213> ORGANISM: Artificial Sequence
<220> FEATURE:
<223> OTHER INFORMATION: Immunostimulatory oligodeoxynucleotide
<220> FEATURE:
<221> NAME/KEY: misc_feature
<222> LOCATION: (1)..(2)
<223> OTHER INFORMATION: N is any nucleotide or no nucleotide

<400> SEQUENCE: 63
nntgcgtcgg tgcagggggg                                               20
```